US009554964B1

(12) United States Patent  (10) Patent No.: US 9,554,964 B1
Johnson et al.  (45) Date of Patent: Jan. 31, 2017

(54) SUSPENSION AND BODY ATTACHMENT SYSTEM AND DIFFERENTIAL PRESSURE SUIT FOR BODY WEIGHT SUPPORT DEVICES

(71) Applicant: Lite Run, Inc., Minneapolis, MN (US)

(72) Inventors: Douglas E. Johnson, Minneapolis, MN (US); John A. Hauck, Shoreview, MN (US); Odd Osland, Apple Valley, MN (US); Mark T. Johnson, Mounds View, MN (US)

(73) Assignee: Lite Run, Inc., Minneapolis, MN (US)

( * ) Notice: Subject to any disclaimer, the term of this patent is extended or adjusted under 35 U.S.C. 154(b) by 1041 days.

(21) Appl. No.: 13/573,692

(22) Filed: Oct. 3, 2012

Related U.S. Application Data

(63) Continuation-in-part of application No. 12/456,196, filed on Jun. 12, 2009, now Pat. No. 8,663,133, which
(Continued)

(51) Int. Cl.
*A61H 3/04* (2006.01)
*A61H 3/00* (2006.01)
(Continued)

(52) U.S. Cl.
CPC ............ *A61H 9/0078* (2013.01); *A61H 3/008* (2013.01); *A61H 3/04* (2013.01); *A41D 13/0007* (2013.01);
(Continued)

(58) Field of Classification Search
CPC ............ A61H 3/00; A61H 3/008; A61H 3/04; A61H 2003/007; A61H 9/0078; A41D 13/0007; A41D 13/0025; A41D 31/02; A41D 2400/32; A41D 2600/10; A63B 2208/053; A63B 2208/056
See application file for complete search history.

(56) References Cited

U.S. PATENT DOCUMENTS 1,629,108 A    5/1927  Lake
2,507,704 A *  5/1950  Frommer ................. A41C 3/00
                                             450/92
(Continued)

FOREIGN PATENT DOCUMENTS

WO    WO2009151630    12/2009

*Primary Examiner* — Valerie L Woodward
(74) *Attorney, Agent, or Firm* — DeWitt Ross & Stevens S.C.

(57) ABSTRACT

The present invention provides a differential pressure body suit with external support against body suit migration. In its preferred embodiment, such body suit may comprise a close-fitting, multi-layered suit sealed against a mammal's skin to contain the differential pressure, or a looser-fitting suit that bends at the mammal's joints with minimal force. External support means include either fixed or movable mechanical supports attached to the body suit, extraordinary air pressure levels for making the body suit rigid, or exo-skeletons attached to the body suit, or a counter-force suspension cable adjustment system. A cyclic control system can turn the differential pressure condition within the body suit on and off on a selective basis to accommodate the movement of the legs of the mammal. This differential pressure body suit provides a portable and convenient system for, e.g., rehabilitating a skeletal joint injury or training the mammal for injury prevention or athletic performance or fat burning. The pressurization reduces the weight of the body to greater or lesser extents, and offloads the weight to the ground through the external support means.

84 Claims, 61 Drawing Sheets

Related U.S. Application Data is a continuation-in-part of application No. 12/319,463, filed on Jan. 7, 2009, now abandoned.

(60) Provisional application No. 61/626,749, filed on Oct. 3, 2011, provisional application No. 61/010,034, filed on Jan. 7, 2008, provisional application No. 61/131,919, filed on Jun. 13, 2008.

(51) Int. Cl.
    *A61H 9/00* (2006.01)
    *A41D 13/002* (2006.01)
    *A41D 13/00* (2006.01)

(52) U.S. Cl.
    CPC ..... *A41D 13/0025* (2013.01); *A61H 2003/007* (2013.01); *A63B 2208/053* (2013.01); *A63B 2208/056* (2013.01)

(56) References Cited

U.S. PATENT DOCUMENTS

| | | | |
|---|---|---|---|
| 2,762,047 A | 9/1952 | Flagg et al. | |
| 2,675,856 A * | 4/1954 | Abdallah | A61H 3/008 182/3 |
| 2,825,327 A | 3/1958 | Tunnicliffe | |
| 3,355,230 A | 11/1967 | Trexler | |
| 3,589,366 A | 6/1971 | Feather | |
| 3,744,491 A | 7/1973 | Fischer | |
| 3,778,052 A * | 12/1973 | Andow | A61H 3/008 135/67 |
| 3,823,711 A | 7/1974 | Hatton | |
| 3,823,712 A | 7/1974 | Morel | |
| 4,003,371 A | 1/1977 | Fischer | |
| 4,039,039 A | 8/1977 | Gottfried | |
| 4,151,612 A | 5/1979 | Vykukal | |
| 4,211,223 A | 7/1980 | LoPiano | |
| 4,230,114 A | 10/1980 | Feather | |
| 4,257,407 A | 3/1981 | Macchi | |
| 4,343,302 A | 8/1982 | Dillon | |
| 4,421,109 A | 12/1983 | Thornton | |
| 4,455,685 A * | 6/1984 | Steffler | B64D 10/00 2/2.11 |
| 4,509,513 A * | 4/1985 | Lasley | A61G 10/026 128/202.12 |
| 4,577,622 A | 3/1986 | Jennings | |
| 4,691,695 A | 9/1987 | Birk et al. | |
| 4,844,452 A * | 7/1989 | Tomosky | A47D 13/043 297/274 |
| 4,959,047 A | 9/1990 | Tripp, Jr. | |
| 5,029,579 A | 7/1991 | Trammell | |
| 5,133,339 A * | 7/1992 | Whalen | A61H 9/005 128/202.12 |
| 5,176,597 A | 1/1993 | Bryne | |
| 5,273,502 A | 12/1993 | Kelsey et al. | |
| 5,356,361 A * | 10/1994 | Watenpaugh | A63B 21/00181 482/111 |
| 5,372,561 A * | 12/1994 | Lynch | A63B 69/0064 482/54 |
| 5,478,310 A | 12/1995 | Dyson-Cantwell et al. | |
| 5,503,143 A | 4/1996 | Marion et al. | |
| 5,512,029 A * | 4/1996 | Barnard | A63B 21/4009 482/124 |
| 5,537,686 A | 7/1996 | Krutz, Jr. et al. | |
| 5,704,881 A | 1/1998 | Dudley | |
| 5,865,722 A | 2/1999 | Heng | |
| 5,873,768 A * | 2/1999 | Fleischman-Ament | A41C 3/0057 2/73 |
| 5,997,465 A | 12/1999 | Savage et al. | |
| 6,027,464 A * | 2/2000 | Dahlquist | A61H 1/0229 601/148 |
| 6,045,519 A | 4/2000 | Smith, Sr. | |
| 6,093,024 A * | 7/2000 | Sokolowski | A47D 13/107 297/274 |
| 6,273,844 B1 * | 8/2001 | Kelsey | A63B 69/0064 482/54 |
| 6,302,828 B1 | 10/2001 | Martin et al. | |
| 6,460,195 B2 | 10/2002 | Wang | |
| 6,589,194 B1 | 7/2003 | Calderon et al. | |
| 6,757,916 B2 | 7/2004 | Mah et al. | |
| 6,821,233 B1 * | 11/2004 | Colombo | A61F 5/0102 482/54 |
| 7,341,543 B2 * | 3/2008 | Dandy | A63B 22/20 280/271 |
| 7,363,931 B2 | 4/2008 | Weaver | |
| 7,591,795 B2 | 9/2009 | Whalen et al. | |
| 2002/0025889 A1 * | 2/2002 | Egger | A61H 1/0214 482/57 |
| 2002/0116741 A1 | 8/2002 | Young | |
| 2003/0032904 A1 * | 2/2003 | Egger | A61H 36/00 601/151 |
| 2003/0216672 A1 | 11/2003 | Rastegar et al. | |
| 2004/0063550 A1 | 4/2004 | Harris | |
| 2005/0070405 A1 | 3/2005 | Egger | |
| 2005/0101448 A1 * | 5/2005 | He | A61H 1/0237 482/54 |
| 2006/0049611 A1 | 3/2006 | Stevens | |
| 2006/0135889 A1 * | 6/2006 | Egli | A61H 9/005 601/11 |
| 2006/0156517 A1 * | 7/2006 | Hammerslag | A43B 5/16 24/68 SK |
| 2006/0189899 A1 | 8/2006 | Flaherty et al. | |
| 2007/0157651 A1 | 7/2007 | Naaman | |
| 2007/0179421 A1 | 8/2007 | Farrow | |
| 2007/0181121 A1 * | 8/2007 | Whalen | A61G 10/023 128/202.12 |
| 2010/0000547 A1 | 1/2010 | Johnson et al. | |

* cited by examiner

SUSPENSION AND BODY ATTACHMENT SYSTEM AND DIFFERENTIAL PRESSURE SUIT FOR BODY WEIGHT SUPPORT DEVICES

CROSS-REFERENCE TO RELATED APPLICATION

This application claims the benefit of the U.S. provisional application No. 61/626,749 entitled "Suspension and Body Attachment System and Differential Pressure Suit for Body Support Devices" filed on Oct. 3, 2011, and is a continuation-in part of U.S. Ser. No. 12/456,196 filed on Jun. 12, 2009, which is a continuation-in-part of U.S. Ser. No. 12/319,463 filed on Jan. 7, 2009, which claims the benefit of U.S. provisional application No. 61/010,034 filed on Jan. 7, 2008, and 61/131,919 filed on Jun. 13, 2008, all of which are hereby incorporated by reference.

FIELD OF THE INVENTION

This invention relates generally to the motion and physical health of the mammalian body, and more specifically to portable systems for assisting humans or other animals to medically rehabilitate or train specific body parts through the application to such body parts of differential pressure.

BACKGROUND OF THE INVENTION

Vertebrate animals feature a flexible, bony skeletal framework that provides the body shape, protects vital organs, and enables the body to move. The human skeleton comprises approximately 206 separate bones. These bones meet at joints, the majority of which are freely movable. The skeleton also contains cartilage for elasticity, and muscular ligaments consisting of strong strips of fibrous connective tissue for holding the bones together at their joints.

The femur, fibula, tibia, and metatarsal bones of the legs and feet support the body and therefore bear its weight. Muscles associated with the ilium, pubis, ischium, patella, tarsal, and phalanges bones provide the necessary bending of the hips, knees, ankles, and toes that are essential for humans to walk, run, climb, and engage in other locomotion activities.

Likewise, the humerus, ulna and radius bones and metacarpal and phalanges bones form the arms and hands, respectively. Muscles associated with the clavicle, scapula, and carpals enable the arm to bend or flex at the shoulder or elbow, and the hand to flex at the wrist and fingers, which is useful for lifting, carrying, and manipulating objects.

Over time, body bones or joints can become damaged. Bones fracture; ligaments tear; cartilage deteriorates. Such damage may result from the aging process, manifested by arthritis, osteoporosis, and slips and falls. But injuries are also caused by sports activities. For example, recreational and competitive running is enjoyed by some 37 million Americans with 25% of them suffering from running injuries annually. Meanwhile, 57 million Americans bicycle for recreational or transportation purposes. In addition to bodily injuries caused by falls, prolonged bicycling can result in groin discomfort or numbness. This medical injury is caused by the horn of the bicycle saddle creating pressure points that can occlude the arteries and veins that supply blood flow to the genitals. Within the 1999-2004 time period, 21 publications within multiple medical specialties (e.g., sexual medicine, urology, neurology, cardiology, biomedical engineering, sports medicine and emergency medicine) established a clear relationship between bicycle riding and erectile dysfunction ("ED").

A number of different approaches have been taken within the industry and the medical community for preventing or treating these injuries. Exoskeletons entail external support systems made from strong materials like metal or plastic composite fibers shaped for supporting proper posture of the human body. Honda Motor Co. has employed "walking assist devices" for its automotive factory workers to support bodyweight for reducing the load on assembly line workers' legs while they walk, move up and down stairs, and engage a semi-crouching position throughout a work shift. The U.S. military has experimented with exoskeletons for its soldiers to enable them to carry heavy equipment packs and weapons. However, the body must be connected to the exoskeleton at the limbs and other parts by means of straps and other mechanical attachment devices. The exoskeleton's motor must be regulated by various sensors and controls, and driven by hydraulics, pneumatics, springs, or other motorized mechanical systems. These can be cumbersome and expensive systems that do not necessarily reduce the stress on the body caused by gravity.

Athletes and older people suffering from joint injuries have rehabilitated in pools and water tanks. The buoyant property of the water provides an upwardly-directed force to the body that lightens the load otherwise directed to the joints. However, these types of systems are not portable, since the person is confined to the pool or water tank. Moreover, pools or water tanks may be unavailable or expensive to install.

Another approach is provided by a harness system exemplified by U.S. Pat. No. 6,302,828 issued to Martin et al. Consisting of an overhead frame to which is connected a raiseable body harness, such a system supports a portion of a person's body weight as he, e.g., walks or runs on a treadmill in order to diminish downward forces on the body joints. But the straps and attachment devices create localized pressure points and stresses on the body, and restrict the range of motion of the body and its limbs. Such a mechanical weight off-loading system may also lack portability.

The National Aeronautics and Space Administration ("NASA") has developed a system that utilizes differential air pressure to provide a uniform "lift" to the body to assist the exercise process. See U.S. Pat. No. 5,133,339 issued to Whalen et al. The differential pressure is applied to the lower half of the person's body that is sealed within a fixed chamber to create a force that partially counteracts the gravitational force on the body. A treadmill contained within the sealed chamber allows the person to exercise. However, this Whalen system requires a large, immobile pressure chamber containing a treadmill. Such a system is expensive and requires cumbersome entry and exit by the person. It will not enable the person any other means of exercise besides the treadmill.

Pressurized bodysuits have also been used within the industry for several different applications. For example, U.S. Published Application 2002/0116741 filed by Young discloses a bodysuit with integral supports and internal air bladders that are filled with pressurized air. This air pressure exerts force against the muscles of a person wearing the suit to tone them during daily activities. U.S. Pat. No. 6,460,195 issued to Wang illustrates exercise shorts with buckled belts, air bags, and a vibrator that directs pulses of pressurized air to the body to work off fat and lift the hips. U.S. Pat. No. 3,589,366 issued to Feather teaches exercise pants from which air is evacuated, so that the pants cling to the body of an exerciser to cause sweating, thereby leading to weight loss.

The U.S. military has also employed pressurized suits of various designs for protecting fighter pilots from debilitating external G-forces. Due to rapid changes in speed and direction, the fighter pilot's body undergoes very high accelerations. This normally forces the pilot's oxygen-laden blood away from the portion of the circulatory system between the heart, lungs and brain, pooling instead toward the blood vessels of the lower extremities. As a result, the pilot can lose situational awareness and spatial orientation. A pilot's bodysuit pressurized against the blood vessels of the legs can force the oxygen-laden blood back to the head and torso of the pilot. See U.S. Pat. No. 2,762,047 issued to Flagg et al.; U.S. Pat. No. 5,537,686 issued to Krutz, Jr. et al.; and U.S. Pat. No. 6,757,916 issued to Mah et al. U.S. Pat. No. 5,997,465 issued to Savage et al. discloses a pants bodysuit made from metal or polymer "memory material" that is heated by electrical current to form around the body, and then cooled to apply pressure for treating this G-forces phenomenon.

Pressurized bodysuits have been used previously for other purposes, such as splinting leg fractures, stopping bleeding from wounds, treating shock, and supporting the posture of partially paralyzed patients. See, e.g., U.S. Pat. No. 3,823,711 issued to Hatton; U.S. Pat. No. 3,823,712 issued to Morel; U.S. Pat. No. 4,039,039 issued to Gottfried; and U.S. Pat. No. 5,478,310 issue to Dyson-Cartwell et al. Bodysuits can also have air between the suit and the body evacuated by vacuum to draw the suit into close contact with the body. See U.S. Pat. No. 4,230,114 issued to Feather; U.S. Pat. No. 4,421,109 issued to Thornton; and U.S. Pat. No. 4,959,047 issued to Tripp, Jr. See also U.S. Published Application 2006/0135889 filed by Egli.

Such pressurized body suits have not previously been used to rehabilitate skeletal joint injuries or minimize conditions that cause erectile dysfunction. Moreover, they have typically been used only in stationary situations like a sitting pilot due to the problem of air pressure forcing the body suit off the lower torso. In some applications like weight-loss patients, suspender straps have been required to overcome this downwards migration of the bodysuit pants.

Thus, a pressurized bodysuit that can be used to apply localized differential pressure to a lower or upper body part for injury rehabilitation or minimization, coupled with an external support or pressure condition control system would be beneficial, particularly due to its portable nature. Such a pressurized body suit system could be worn by a patient, athlete, or other person within a variety of settings to perform a variety of different functions.

Ambulatory assist devices such as walkers, rollators, are used to assist elderly or physically-impaired people undergoing rehabilitation, or people suffering from gait and balance problems due to strokes, Parkinson's and other neurological disorders. These devices are used to provide balance and some measure of body weight support often by the person using their arms and hands. Use of these devices requires the disabled person raise himself from a sitting position to a standing position in order to use the device to ambulate. However, physically impaired people often lack the strength and or balance in order to raise themselves from a sitting to a standing position without assistance. This prevents people from independently using ambulatory assist devices. Also providing personnel for assistance entails additional costs for rehabilitation institutions or in providing home care. Walkers that incorporate a means for assisting a seated person to stand are commercially available or otherwise known in the art. One example is U.S. Pat. No. 7,363,931 which provides lifting arms to assist in standing. One commercially available device is "The New Lift Walker" available from newliftwalker.com. It incorporates a harness and arm supports and a pneumatic lift device to assist in raising a person from a seated to a standing position. These devices generally lack having a body weight support capability. Instead the person is able to provide some body weight support using their arms and hands as supports. Some mobility assist devices utilize a harness to provide body weight support. However harness systems have the drawbacks we have described earlier. There is a need for improved mobility assist devices that provide both improved means of body weight support and a means for assisting a person to raise himself from a seated to a standing position. The wheeled support aid with lift mechanism may utilize electric or pneumatic power sources or both.

Training of gait and balance with body weight support (BWS) is a promising rehabilitation technique. The current body weight support method utilizes an overhead harness support mechanism for which commercial systems are available. One harness system is exemplified by U.S. Pat. No. 6,302,828 issued to Martin et al. Consisting of an overhead frame to which is connected a raiseable body harness, such a system supports a portion of a person's body weight as he, e.g., walks or rims on a treadmill in order to diminish downward forces on the body joints. Harnesses for body weight support attach upper torso and the pulling force on the body is directly upwards. This restricts the natural position of the body during running and walking to a forward leaning position. Because harness systems pull the upper body directly upwards from the chest they are can provide too much stability for balance training. Another issue with the harness based body weight support is that the harness supporting the subject decreases the need for natural associated postural adjustments (APAs) that are required for independent gait. The main site for an active control of balance during gait is the step-to step mediolateral placement of the foot. When supported by a harness during BWS training any mediolateral movement is restricted by a medially directed reaction force component that will help stabilize the body in the frontal plane and decrease or even eliminate the need for APAs making gait and balance training less effective. Further the straps and attachment devices create localized pressure points and stresses on the body, and restrict the range of motion of the body and its limbs. In particular the straps around the thighs and groin interfere with the back and forth rotation of the legs.

An new alternative to a harness based body weight support is a close fitting differential pressure suit is described in this application and in U.S. Patent Application [US 2010/0000547, PCT/US2009/003535, EP 09762926.5]. A differential pressure body suit with external support against body suit migration is provided by the invention. In its preferred embodiment, such body suit may comprise a close-fitting, multi-layered suit sealed against a person's skin to contain the differential pressure, or a looser-fitting space suit that bends at the joints with minimal force. External support means include either fixed or movable mechanical supports attached to the body suit, extraordinary air pressure levels for making the body suit rigid, or exoskeletons attached to the body suit. This differential pressure body suit provides a portable and convenient system for rehabilitating a skeletal joint injury or training for injury prevention or athletic performance. The pressurization reduces the weight of the body to greater or lesser extents, and offloads the weight to the ground through the external support means. The body suit is flexible and has joints that can flex with minimal force even under pressure.

In either harness based approaches or partial pressure differential pressure suit means are required for attaching the harness, pressure suit or other attaching means to the mechanism that provides the counter-force body weight support. Harness systems use ropes straps and or cables to attach the harness system to the overhead counter-weight system. A natural walking or running gait consists of body movements or rotations about various axes of the body. It is important that the connecting system not unduly restrict these movements. There is a need for body weight support systems that do not restrict natural body movements.

SUMMARY OF THE INVENTION

The present invention provides a differential pressure body suit with external support against body suit migration. The invention provides body weight support in a way that does not restrict one's natural body movements that occur while walking or running. Specifically the invention is an improved system for a body weight support device for connecting a person's body to the weight off-loading components of the device (referred here to a constant force adjustment mechanism) so as not to restrict natural body movements. In its preferred embodiment, such body suit may comprise a close-fitting, multi-layered suit sealed against a mammal's skin to contain the differential pressure, or a looser-fitting suit that bends at the mammal's joints with minimal force. External support means include either fixed or movable mechanical supports attached to the body suit, extraordinary air pressure levels for making the body suit rigid, or exoskeletons attached to the body suit. A cyclic control system can turn the differential pressure condition within the body suit on and off on a selective basis to accommodate the movement of the legs of the mammal. This differential pressure body suit provides a portable and convenient system for rehabilitating a skeletal joint injury or training the mammal for injury prevention, athletic performance, or fat reduction, or assisting the mobility of the physically disabled. The pressurization reduces the weight of the body to greater or lesser extents, and offloads the weight to the ground through the external support means. The body suit is flexible and has joints that can flex with minimal force even under pressure.

The invention can also be used to assist the mobility for, e.g., the elderly or disabled people, who have common problems such as degenerative hips or knees by reducing the stress on their joints. Furthermore, the alternating pressure/depressurization cycle can provide medical benefits via the body suit similar to massage, or by enhancing venous return of blood to the heart for, e.g., people suffering from varicose veins or other vascular disorders. The system can also facilitate proper posture, and avoid bed sores caused by prolonged horizontal contact by the body with the bed. This is not a purely mechanical system for supporting bodily motion, such as an exoskeleton. This invention is useful not only for humans, but also for other animals like dogs, cats, and horses.

BRIEF DESCRIPTION OF THE DRAWINGS in the accompanying drawings.

DETAILED DESCRIPTION OF THE PREFERRED EMBODIMENT

Figure 1:
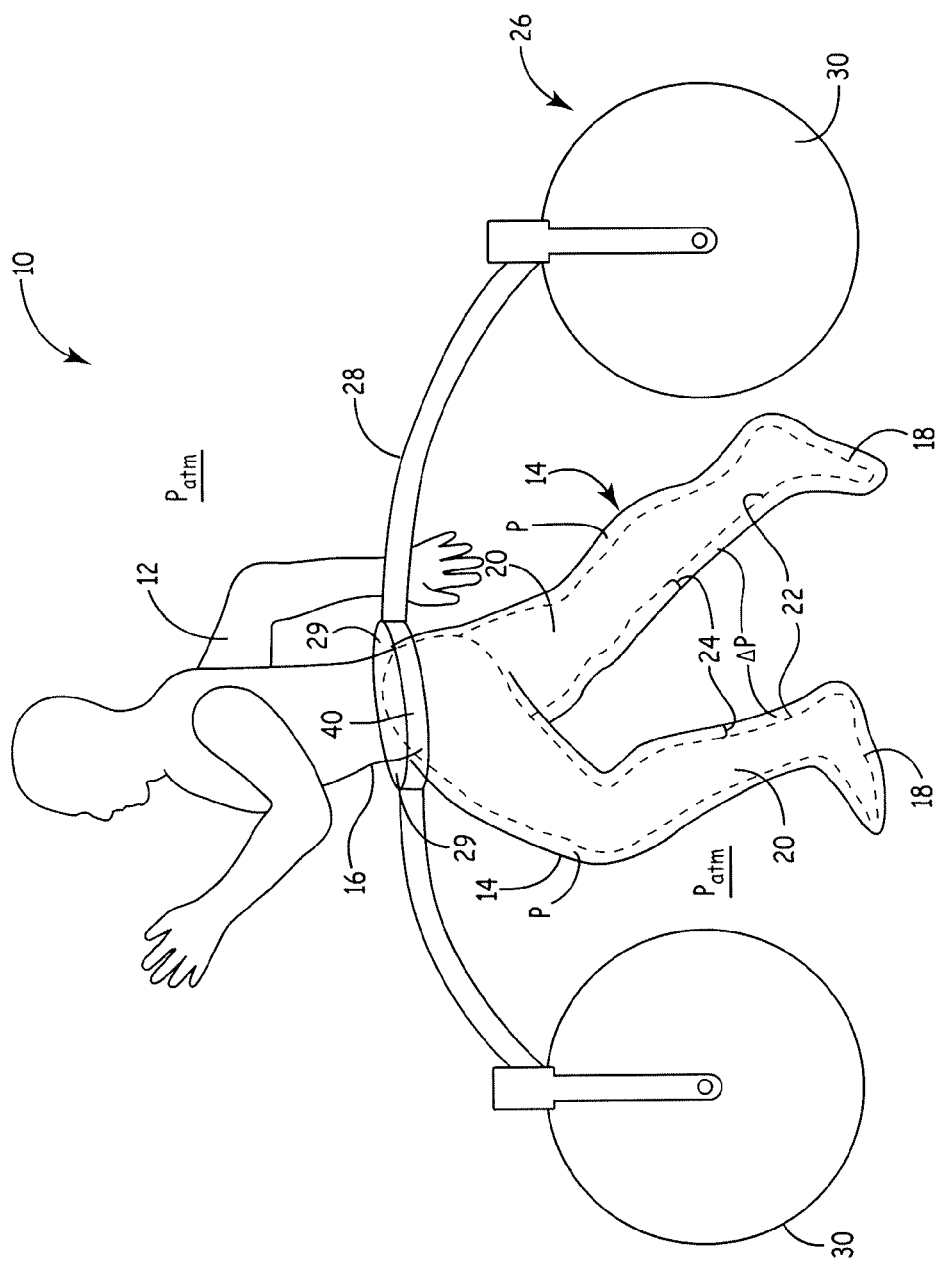
FIG. 1 is a perspective view of the assisted motion system of the present invention.

A differential pressure body suit with external support against body suit migration is provided by the invention. In its preferred embodiment, such body suit may comprise a close-fitting, multi-layered suit sealed against a mammal's skin to contain the differential pressure, or a looser-fitting space suit that bends at the mammal's joints with minimal force. External support means include either fixed or movable mechanical supports attached to the body suit, extraordinary air pressure levels for making the body suit rigid, or exoskeletons attached to the body suit. A cyclic control system can turn the differential pressure condition within the body suit on and off on a selective basis to accommodate the movement of the legs of the mammal. This differential pressure body suit provides a portable and convenient system for rehabilitating a skeletal joint injury or training the mammal for injury prevention, athletic performance, or fat reduction, or assisting the mobility of the physically disabled. The pressurization reduces the weight of the body to greater or lesser extents, and offloads the weight to the ground through the external support means. The body suit is flexible and has joints that can flex with minimal force even under pressure. The invention can also be used to assist the mobility for, e.g., the elderly or disabled people, who have common problems such as degenerative hips or knees by reducing the stress on their joints. Furthermore, the alternating pressure/depressurization cycle can provide medical benefits via the body suit similar to massage, or by enhancing venous return of blood to the heart for, e.g., people suffering from varicose veins or other vascular disorders. This is not a purely mechanical system for supporting bodily motion, such as an exoskeleton.

For purposes of the present invention, "differential pressure" means the difference in pressure conditions across opposite sides of the body suit, such as a positive pressure or negative (vacuum) pressure condition contained inside the suit, and an atmospheric pressure condition on the outside of the suit. For example, if atmospheric pressure is equal to 14.7 lbs/in$^2$ ("psi"), and the internal pressurized condition of the body suit is 15.7 psi, then the differential pressure applied by the body suit to the mammal wearing the body suit is 1.0 psi. Such differential pressure can also be represented as $\Delta P$ within this application.

As used within this application, "positive pressure" means any pressure level in excess of atmospheric pressure.

For purposes of this application, "negative pressure" means any pressure level less than atmospheric pressure. A vacuum is an example of such a negative pressure. Partial vacuums are also covered by this invention.

In the context of the present invention, "body portion" means any part of the body to which the differential pressure condition is applied by the body suit. Examples include, without limitation, feet, legs, knees, hips, shoulders, arms, elbows, torso, and the back.

As used within this application, "body suit" means a single or multi-layered, close-fitting or loose-fitting suit capable of containing a positive or vacuum pressure condition that covers a predetermined body portion. Examples include, without limitation, trunks, shorts, full-length pants, such pants that cover the feet, shirts, and chest or arm segments. The suit is provided with a means for creating the positive or negative (vacuum) pressure condition within the suit. Such a means may be a port connected to an air pressure control system.

In the context of the present invention, "pressure-tight" means with respect to the body suit that the material forming such body suit is capable of containing a positive or negative pressure condition without substantial diminishment over a time period that is relevant to the usage of the body suit. Thus, pressure tightness does not require an absolute absence of any loss of pressure or vacuum, nor does it require maintenance of the positive pressure or vacuum condition within the suit for a time period greater than the time interval during which the suit is worn for an exercise or therapeutic treatment session, or beyond which such positive pressure or vacuum condition can reasonably be replenished within such exercise or therapeutic session.

For purposes of the present invention, "mammal" means any of a class of higher vertebrates comprising humans and all other animals that nourish their young with milk secreted by mammary glands, and have the skin usually more or less covered with hair. Such animals include, without limitation, horses, dogs, and cats.

A human runner will be used as an exemplary mammal for purposes of describing the assisted motion system of the present invention. It is important to appreciate, however, that any other type of mammal for any other kind of exercise, life activity, or rehabilitative activity is covered by this application, as well.

The assisted motion system 10 of the present invention is shown in FIG. 1. Unlike prior art static systems that require a runner to use a stationary treadmill, this system is portable, thereby enabling the runner 12 to enjoy exercising outdoors on the road or a trail. In this embodiment, the runner wears a differential pressurized pant suit 14 that extends downwardly from the runner's waist 16 and covers the feet 18. The runner's legs 20 are depicted inside the differential pressurized suit 14 in broken lines 22.

The differential pressurized suit 14 is constructed of air-tight material, and affords easy movement by the body and limbs of runner 12 while running. The suit 14 is sealed against the body at the waist 16. When air pressure condition P above atmospheric pressure $P_{atm}$ is added to the volumetric region 24 defined between the runner's legs 20 and the suit 14, a differential pressure condition $\Delta P$ is created in which the runner's lower body portion contained within the suit 14 experiences a higher pressure condition than the runner's upper body 26, which only experiences $P_{atm}$. Due to this pressure differential $\Delta P$, an upwards force is exerted on the runner 12 by the higher air pressure contained inside the suit 14, thereby acting to diminish the weight of the runner's body. Runner 12 thereby experiences a reduced weight on his feet, knees, legs, and lower body when he runs in this differential pressurized suit 14, compared with if he ran without the suit.

Figure 2:
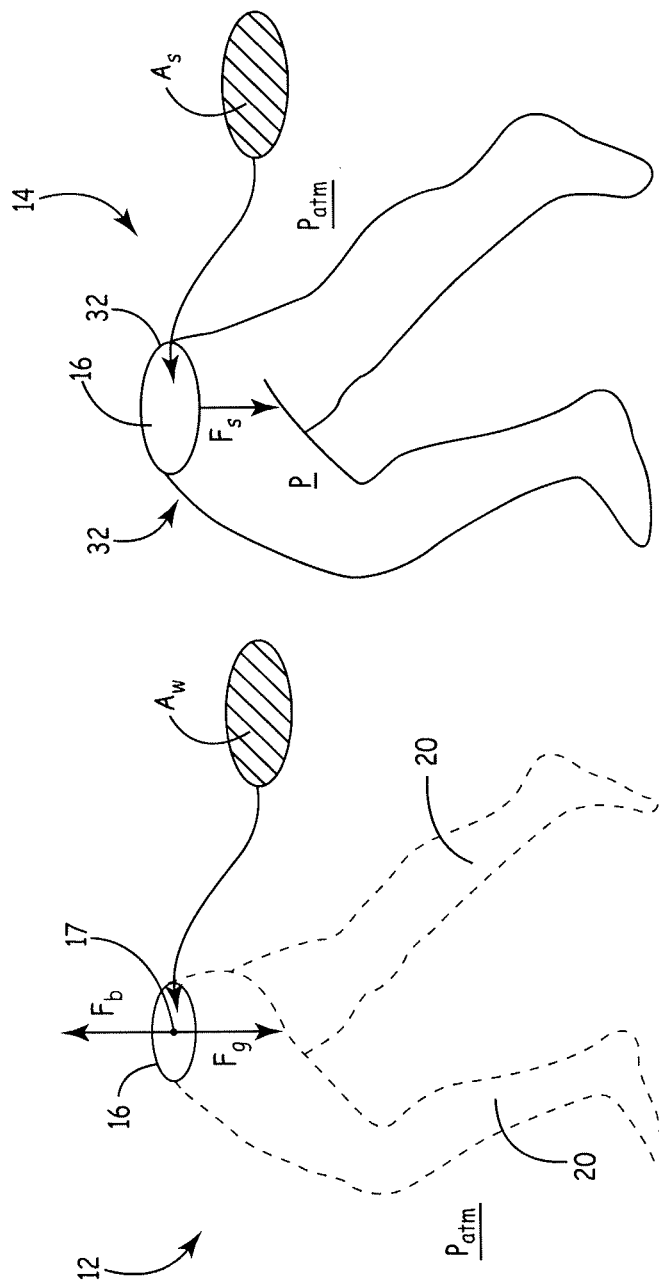
FIG. 2a is a schematic view of the legs and feet of a human and the forces applied thereto.
FIG. 2b is a schematic view of a body suit of the present invention and the forces applied thereto.

FIG. 2 illustrates the various vector forces on the runner's body. The runner 12 and the differential pressurized suit 14 are depicted separately in FIGS. 2a and 2b, respectively, for ease of understanding. The force from gravity exerted on the runner's body mass is shown as $F_g$. In use, the suit 14 is sealed to the runner's body at the waist 16, and pressurized to pressure P to create the differential pressure condition $\Delta P$ between the upper and lower bodies. The cross-sectional area of the body at waist 16 is depicted as area $A_w$. The positive pressure P is directed against the body and legs 20.

The differential pressure condition $\Delta P$ results in an upwards-directed resultant force $F_b$ on the body located at the centroid 17 of cross-sectional area $A_w$. This total upwards force $F_b$ is:

$$F_b = \Delta P \times A_w$$

This constitutes the amount of weight that is effectively reduced from the lower body 20 of runner 12. For example, a runner experiencing a pressure differential $\Delta P$ on the lower body of 0.5 psi having a cross-sectional waist area of $A_w$ of 100 square inches would experience a 50 lb reduction in weight due to the differential pressurized suit 14.

FIG. 2b illustrates the various vector forces on the suit 14. The cross-sectional area of the suit at waist 16 is depicted as $A_s$. In the case of a closely-fitting body suit, $A_s$ should approximate $A_w$. The positive pressure differential $\Delta P$ also results in a downwards directed force $F_s$ on the suit 14. The amount of this downwards force $F_s$ is:

$$F_s = \Delta P \times A_s.$$

This constitutes the amount of force that pushes the suit down the body. For example, a suit pressurized to a pressure differential $\Delta P$ of 0.5 psi having a cross-sectional waist area As of 100 square inches is subject to a 50 lb downwards force. This force $F_s$ would ordinarily cause suit 14 to work its way downwardly along legs 20. Therefore, an important part of the invention is the inclusion of external support 26 to prevent the downward migration of the suit. In the case of the embodiment depicted in FIG. 1, external support 26 constitutes a frame 28 that is operatively connected to wheels 30. The suit is attached to the frame 28 at attachment points 29. When the differential pressurized suit 14 is connected to frame 28, the downward force $F_s$ exerted on the suit 14 is matched by the upwards reaction force exerted by the supporting structure at the attachment points 32.

In this manner, the supported differential pressurized suit 14 is able to diminish the weight of the runner's body without contacting the body. Through the application of differential pressure $\Delta P$, an amount of weight $\Delta W$ of the body equal to:

$$\Delta W = W - (\Delta P \times A_w)$$

is transferred from the muscle-skeletal structure of the runner's lower body 20 to the frame 28 of the supporting structure 26, and through the frame 28 and wheels 30 to the ground. Moreover, the support structure prevents force $F_s$ from pulling the differential pressurized suit 14 off runner 12. Furthermore, because the wheel-based support structure 36 and differential pressurized suit 14 are completely portable in nature, runner 12 can go anywhere with the motion-assisted system 10, instead of being confined to a stationary or pressure chambers as with prior art systems.

When the runner's body is in contact with the ground via feet 18, various amounts of weight can be effectively removed from the body, depending upon the level of positive pressure P introduced to the body suit. For example, for a 180 lb runner having a cross-sectional area $A_w$ of 100 square inches, a differential pressure $\Delta P$ of 1 psi would reduce his weight by 100 lbs. The runner's lower body would therefore only need to support a weight of 80 lbs. A 0.5 psi pressure differential $\Delta P$ would take off 50 lbs of weight. A 0.25 psi pressure differential would take off 25 lbs of weight.

Figure 3:
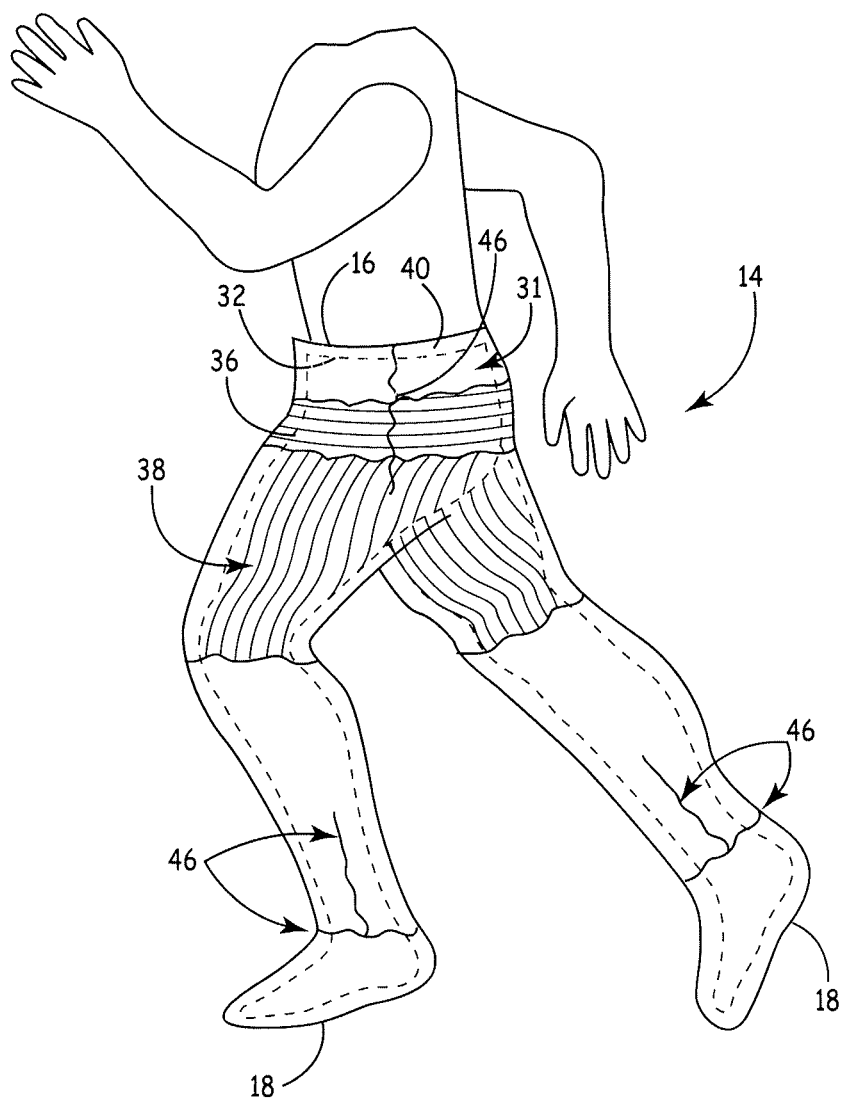
FIG. 3 is a cut-away view of the body suit.
Figure 4:
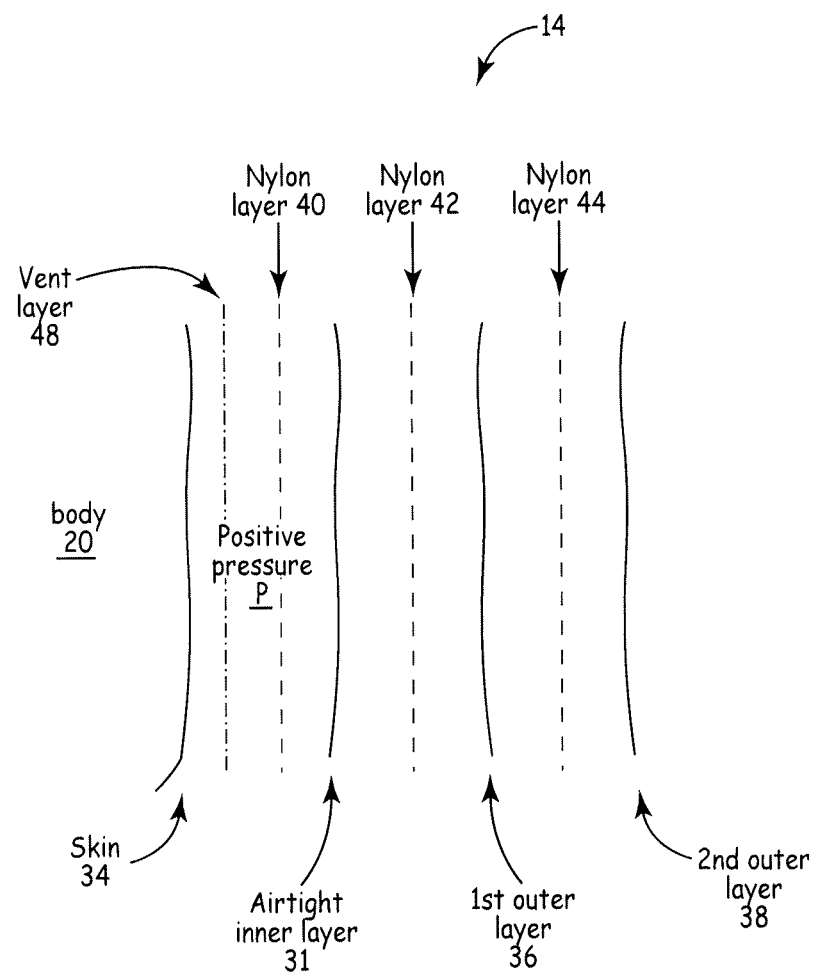
FIG. 4 is a schematic view of the construction of the body suit.

The preferred construction of differential pressurized suit 14 is shown in greater detail in FIGS. 3-4. Close fitting suits provide the advantage of greater mobility for runner 12. Suit 14 is constructed from at least three layers of material. FIG. 3 shows a cut-away view of the suit illustrating its different layers.

An air-tight inner layer 31 featuring an airtight seal 32 at the waist 16 of the runner's body 20 maintains the positive pressure P condition inside the suit against the runner's body skin 34. The fabric for this air-tight layer which is closest to the body may be formed from any pressure-tight material that is also sufficiently flexible to afford mobility by the runner. Examples include, without limitation, latex rubber, neoprene, and air-tight elastic fabrics like latex-coated Lycra. This fabric should be sufficiently thin and elastic to provide comfort without restriction. Preferably, suit 14 is about 0.002-0.040 inch thick, more preferably about 0.005-0.015 inch thick, still more preferably about 0.010 inch thick. The elasticity of the material can be expressed by spring rate, which is the force necessary to double a one-inch-thick strip of fabric. Preferably, this spring rate should be about 0.2-2.0 lbs, more preferably about 0.5-1.5 lbs, still more preferably about 1.0 lb.

Two outer layers 36 and 38 of the differential pressurized suit 14 composition prevent the suit from expanding due to the force applied by positive pressure P, while maintaining the shape of the suit to fit closely to the body. This close fit provides for ease of mobility of the body and its limbs 20. It also prevents the legs of the suit from contacting each other during the running motion. Moreover, this close fit of the suit reduces the volume of pressurized air or other suitable gas in contact with the body joints in order to facilitate bending of the legs.

The fabric for these first and second outer layers 36 and 38 should be composed of mesh, netting, or other suitable fabric. Suitable mesh material is available from Apex Mills Corporation of Inwood, N.Y. This mesh or netting is constructed to mostly be non-extending along one axis, and elastic or extensible along a second axis perpendicular to the first axis. Exemplary mesh materials include, without limitation, nylon-Lycra that can be knit or braided, or a monofilament like nylon or Dacron.

The first outer layer 36 serves to prevent the suit 14 from expanding circumferentially. The circumferential direction of expansion is perpendicular to the longitudinal axis of the legs and body fabric. The fabric is oriented so that its non-extending axis follows this direction. The fabric can be more specifically oriented so that its non-extending axis follows lines on the body in which the skin does not stretch or extend during bending or other movement. These lines are known within the industry as "lines-of-non-extension." Lines of non-extension run both parallel and perpendicular to the longitudinal axis of the legs and body. This first layer of fabric preferably would follow the perpendicular lines of non-extension.

The second outer layer 38 serves to prevent the suit 14 from expanding longitudinally under pressure. This fabric layer is oriented, so that its axis of non-extension generally follows lines that are generally parallel to the longitudinal axis of the legs and body. Preferably, the fabric can be more specifically oriented in this direction to follow longitudinal lines on the body in which the skin does not stretch or extend during bending or other movement. Where appropriate in sections of the body which do not flex, such as the thigh area or lower calves, cloth, mesh, or net material that is non-extendible along both axes may be used. This second outer fabric layer 38 which is mostly non-extensible in the vertical direction of an upright body effectively carries the vertical downward load on the suit resulting from the positive pressure differential.

Differential pressurized suit 14 may also feature additional layers of nylon 40 between the body 20 and the air-tight inner layer 30, and 42 and 44 between the inner 30 and first outer layer 36, and two outer layers 36 and 38, respectively, in order to enable the suit and layers to slip relative to one another on the body to improve the runner's mobility. Air-tight zippers 46 positioned along the suit 14 near its waist 16 and feet 18 portions allow for easy entry and removal of the suit. Such air-tight zippers are available from YKK (U.S.A.) Inc. of Marietta, Ga. Moreover, the suit 14 may feature an inner vent layer 48 that provides airflow and moisture control. In other embodiments these layers can be separately combined into a single layer that provides the same basic functioning as for the separate layers described above.

Figure 5:
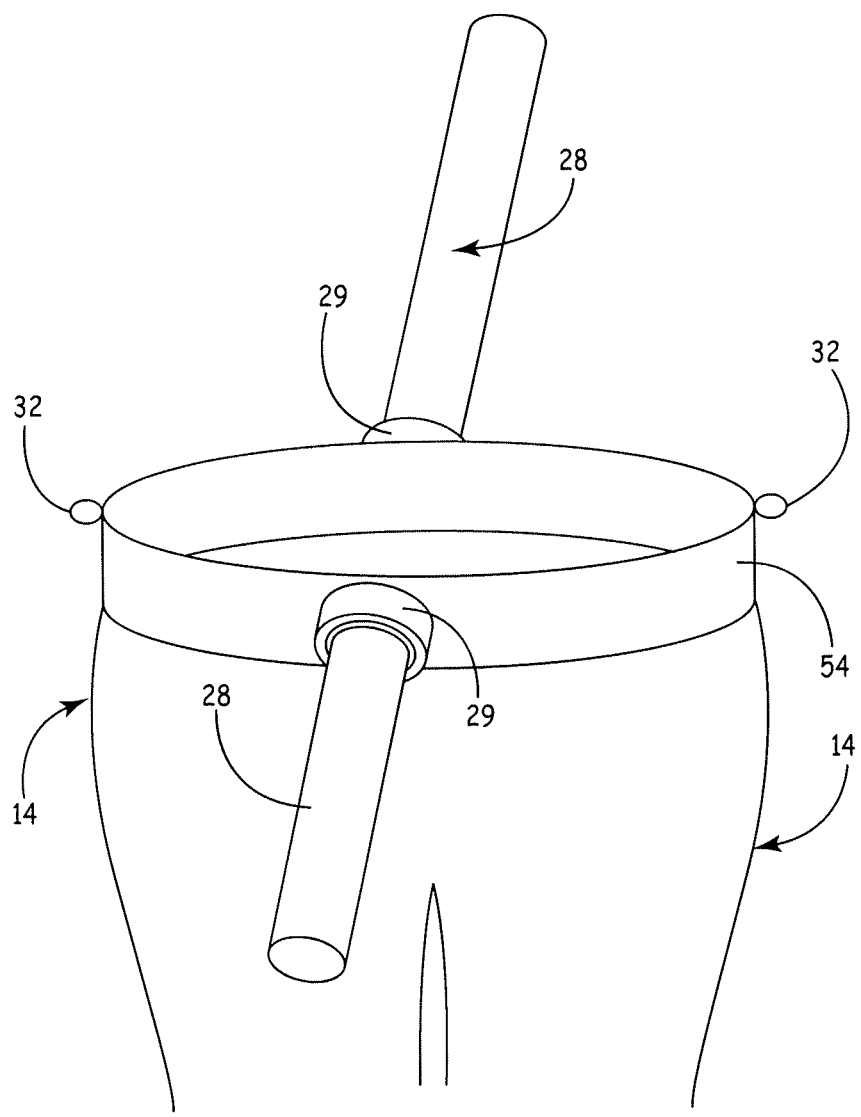
FIG. 5 is a partial view of the body suit connected to a portion of the external support frame.

As shown in FIG. 5, a band 54 serves to attach the suit 14 to the supporting structure 28. This band is attached to the supporting structure with a fitting 29, such as a threaded collar receiving threaded ends extending from support structure 28. The band should conform to the generally elliptical shape of waist cross-section $A_w$ that surrounds the suit 14 at the waist 16. This band serves an additional purpose of containing the outward pressure force in order to enhance the radial inward force as the suit is filled with pressure. This assures that the suit will conform closely to the body at the waist 16.

The band 54 may be made from any suitable material that is strong enough to contain this outwardly-directed force, including metal, plastic, or composites. It may be made moldable to the general shape of the runner's waist, using a thermoset plastic material. The band 54 may alternatively be formed from a strong, flexible fabric, such as nylon. The suit 14 may be attached and detached from the bend 54, using a Velcro fastening system. Other mechanical fastening systems such as straps, snaps, or hooks engaging eyelets may also be utilized. Alternatively, the band can constitute an integral part of the suit. The bend may be in two pieces hinged and fitted with a locking clasp to allow for easy entry.

In the embodiments of the differential pressurized suit 14 shown in FIGS. 1-3, the suit covers the entire lower less and feet, so that the entire lower body below the waist is airtight. A seal 40 is connected to the waist of suit 14 with an airtight connection, so that air pressure cannot escape between the suit and the seal. While the weal 40 may be positioned at the waist area, it may also be located lower, below the hips, or somewhere in between.

Figure 6:
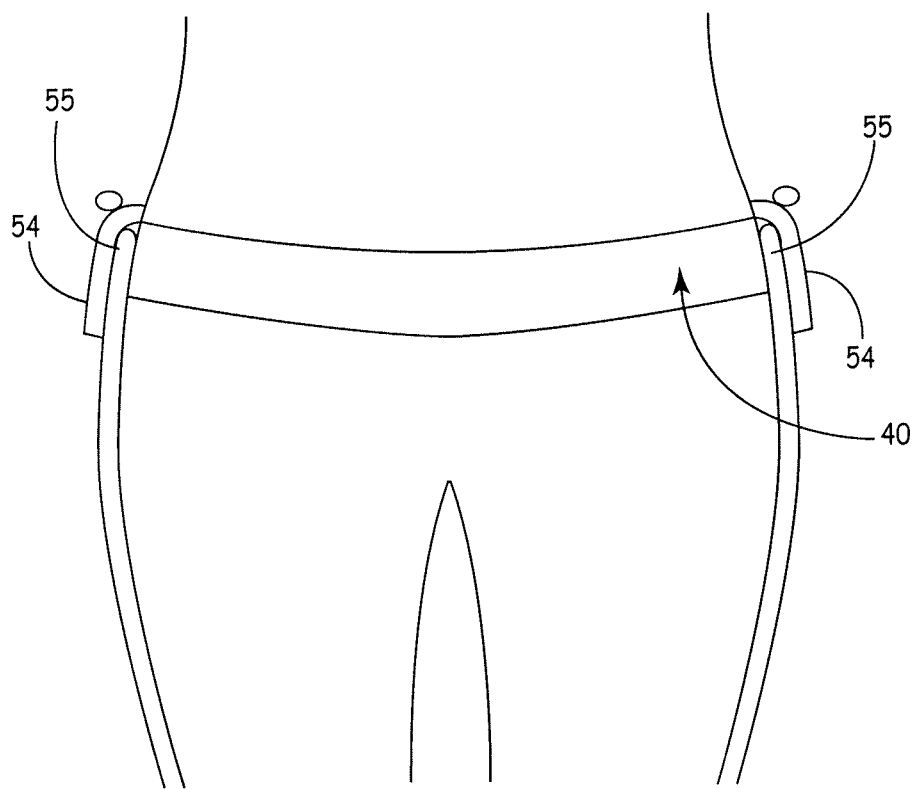
FIG. 6 is a partial front view of a waist seal attached to the interior of the body suit.

The seal 40 constitutes an airtight band of material that fits tightly over the body. As shown more clearly in FIG. 6, it is attached to the suit 14 at 55. This seal 40 is preferably constructed of elastic neoprene, or any other airtight material, such as rubber, latex, or a rubber-coated Lycra. Suitable latex rubber sheeting is available from Rubber Cal of Santa Ana, Calif. The seal should be sufficiently wide across the waist area of the suit to provide for a sufficient airtight closure. The circumference of the seal 40 should be less than the unstretched circumference of the body part that is circumscribed by the seal, so that when the seal 40 is secured around the body part (in this case, the waist area), a positive pressure is applied by the seal to the underlying skin. Combined with the air at pressure P that is introduced into the suit 14 within the volume between the suit's airtight inner layer 30 and the runner's body skin, the suit 14 and associated seal 40 maintain a relatively airtight seal in order to confine the volume of air pressure P inside the suit. The seal 40 is sufficiently airtight that it provides enough sealing force to maintain the air pressure inside the suit using the air control system.

Figure 7:
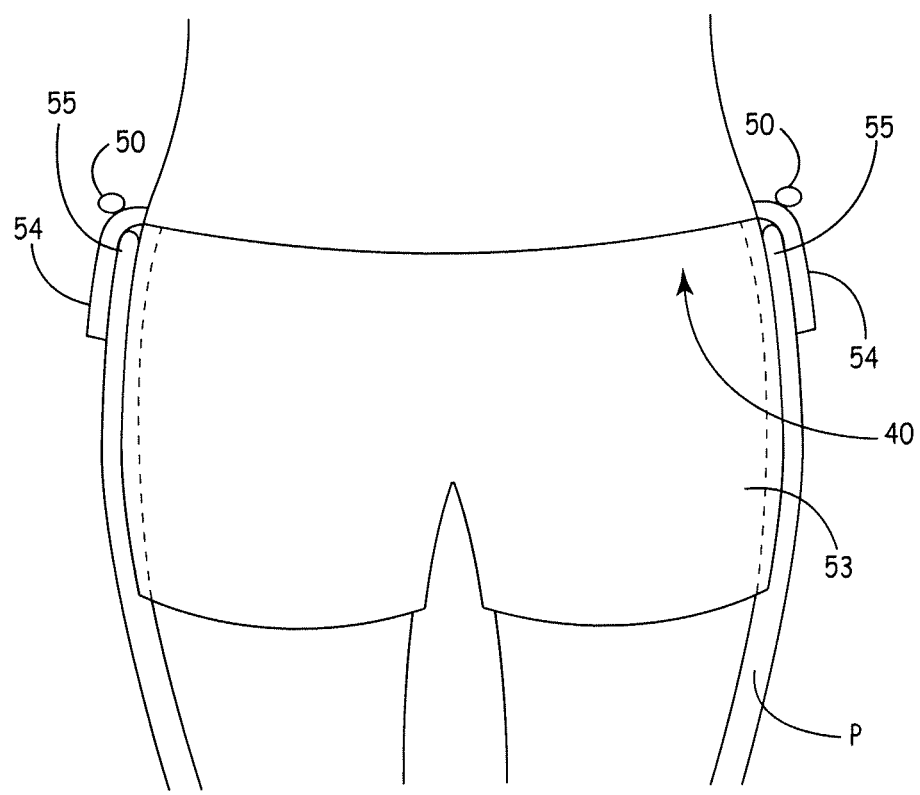
FIG. 7 is a cut-away front view of an alternative airtight shorts embodiment of a waist seal for the body suit.

FIG. 7 shows another embodiment of a waist seal for suit 14. In another embodiment of the differential pressurized suit 14 of the present invention, the waist seal can comprise an airtight pair of shorts 53 that are connected to the interior of the suit. Such shorts can be tight-fitting, airproof neoprene compression shorts that provide a tight fit against the body. These shorts can be connected to the suit at the waist by means of an airproof zipper. The shorts can also consist of a tight-fitting, breathable fabric that has a band of airproof latex or rubber coating at the top or bottom portion to provide the airproof seal against the body.

Figure 8:
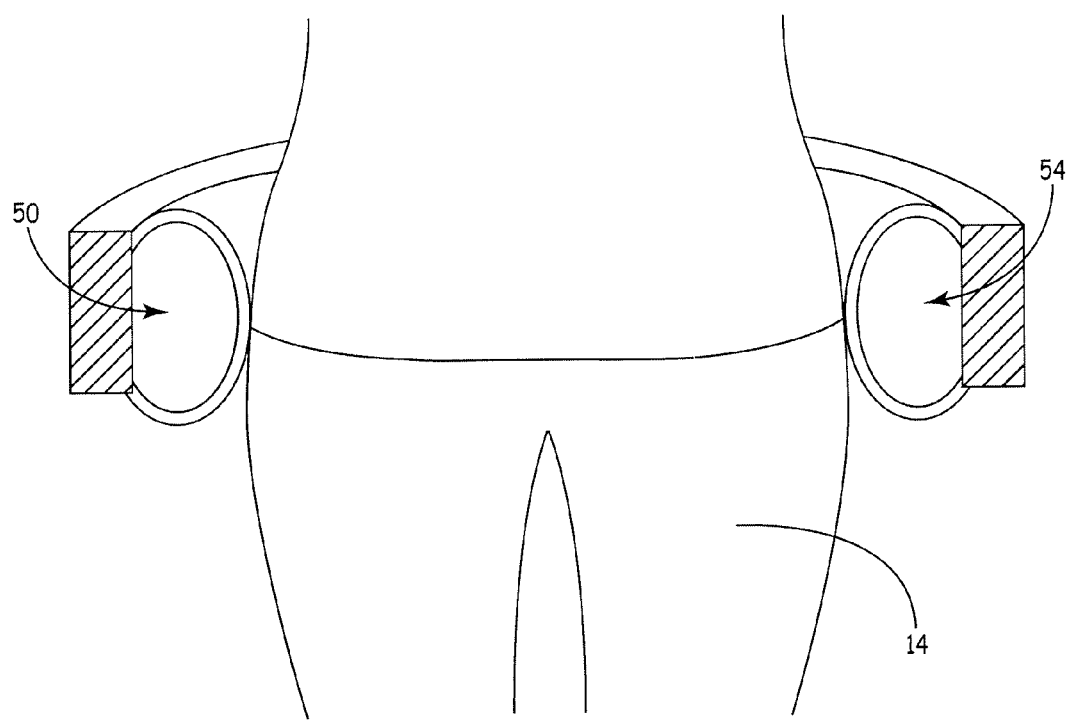
FIG. 8 is a cut-away front view of an inflatable air tube seal for the body suit.

In yet another alternative embodiment, the seal can consist of an inflatable air tube seal 50, as shown in FIG. 8. This inflatable tube seal circumscribes the waist, and is attached via an airtight connection to the exterior of the suit. When inflated with air, the tube seal 50 expands and applies an inwardly directed force to the waist to compress it against the skin to confine the air pressure P condition inside the suit.

Figure 9:
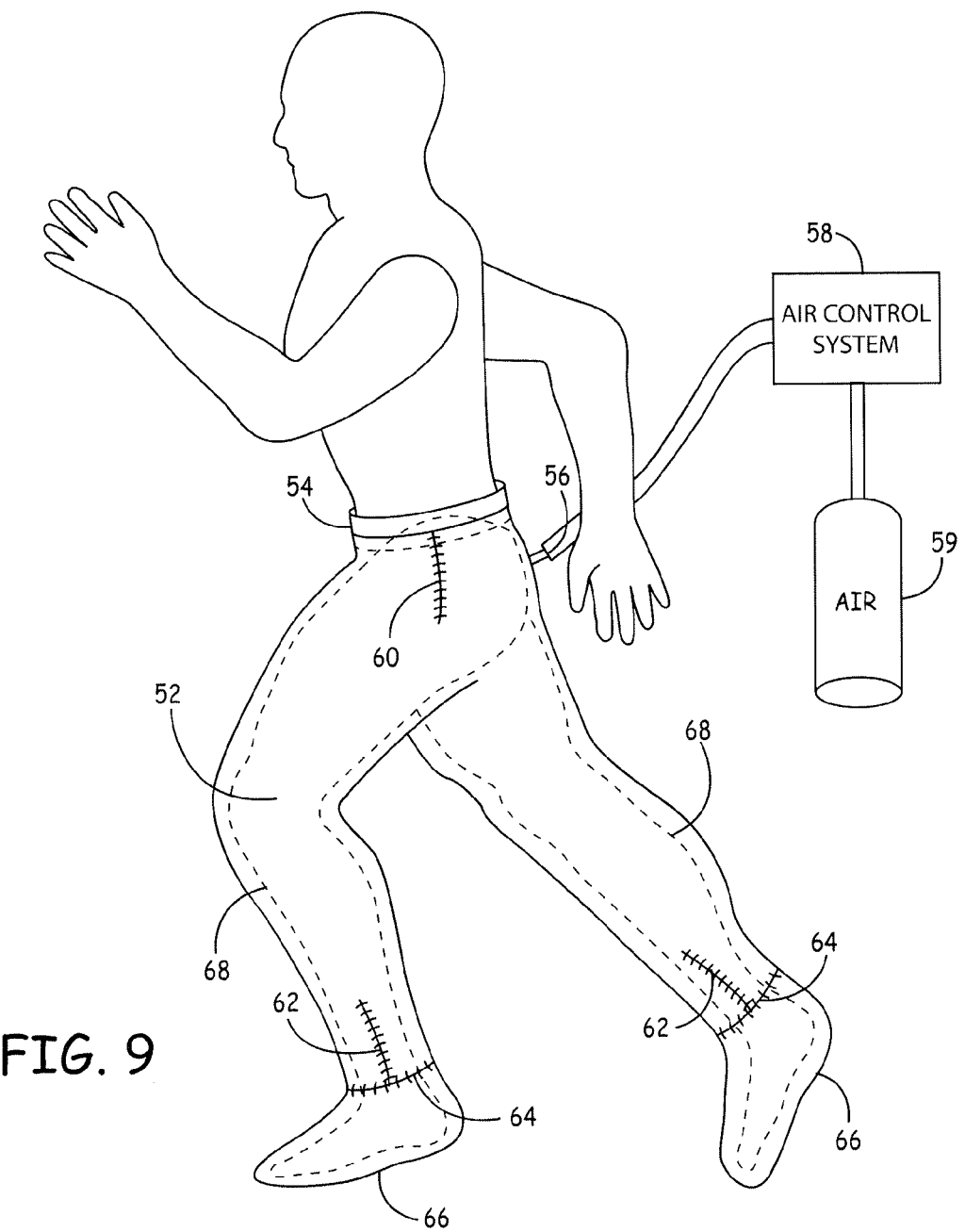
FIG. 9 is a perspective view of a human wearing a full-length pants body suit of the present invention.

As shown in FIG. 9, when suit 14 is pressurized, it maintains a shape close to the body, while affording mobility of the body and limbs. A port 56 is provided in the suit to allow for pressurizing and depressurizing the suit. An air control system 58 connected to an associated pressurized air source 59 maintains the positive pressure condition P inside the suit. The air control system 58 may also control the humidity and temperature levels existing inside the suit. The suit may be statically pressurized once, and then worn by the person without the control system 58. When operating in this manner, the seal 40 maintains the pressure condition for the duration of the time period that the suit is worn. The suit may be worn for time periods ranging between minutes for brief exercises to days for medical rehabilitation.

While this application discusses the use of pressurized air to fill the suit, other pressurized gases may be employed. Other examples of such pressurized gases include nitrogen, carbon dioxide, and argon. Such gases must be non-toxic and not harmful to body skin, or else an inner layer must be worn between the gas and the skin to protect the skin and body.

The differential pressurized suit 52 shown in FIG. 9 comprises a full-length pair of pants which also completely cover the feet. Airtight zippers 60 assist entry into the waist region of the pants. Airtight zippers 62 do the same for ankle regions. Finally, airtight zippers 64 allow the foot portion 66 of the suit 52 to be attached to the pants portion 68 after the feet are inserted through the pant legs.

Figure 10:
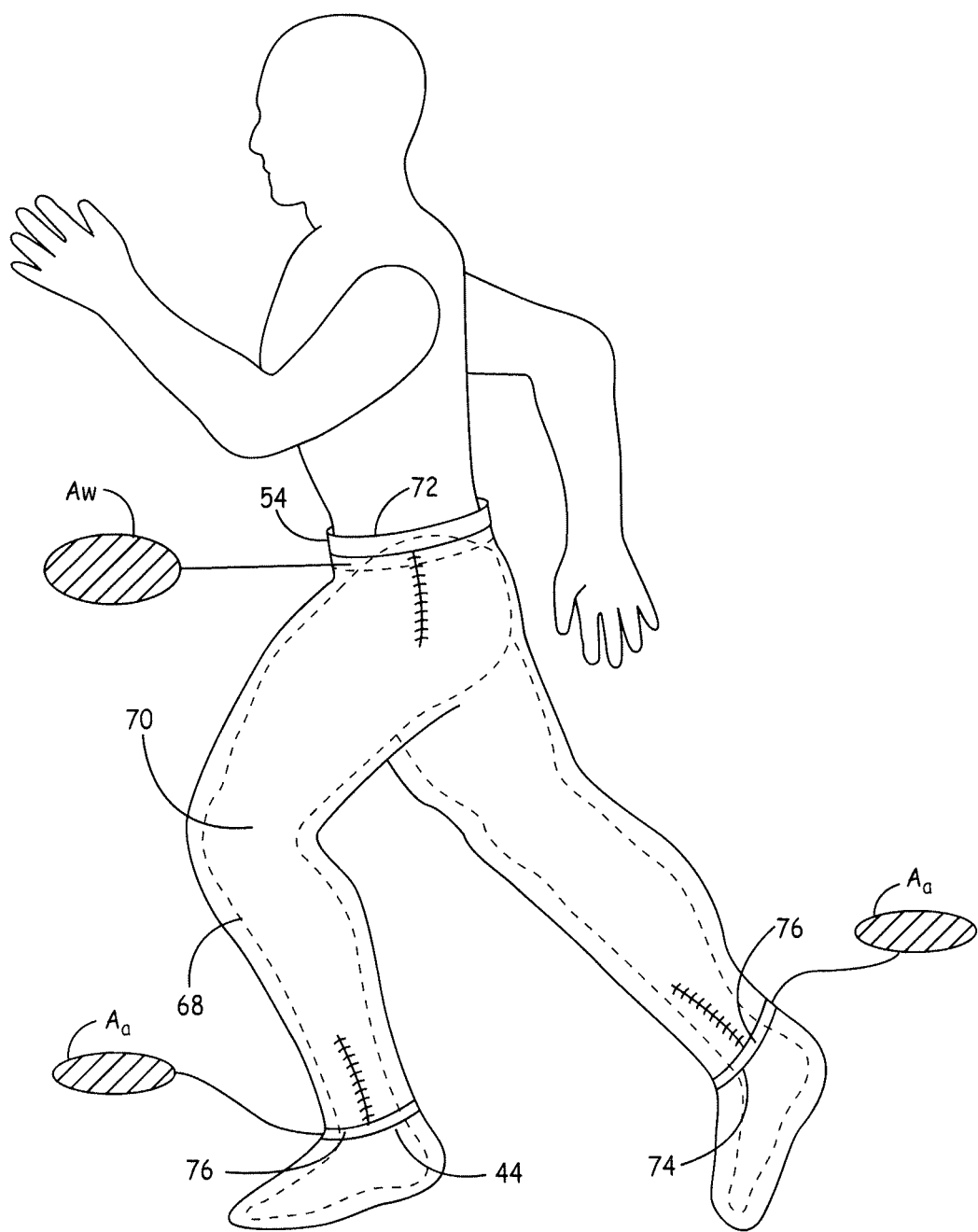
FIG. 10 is a perspective view of a human wearing a pants body suit only extending to the ankles.
Figure 11:
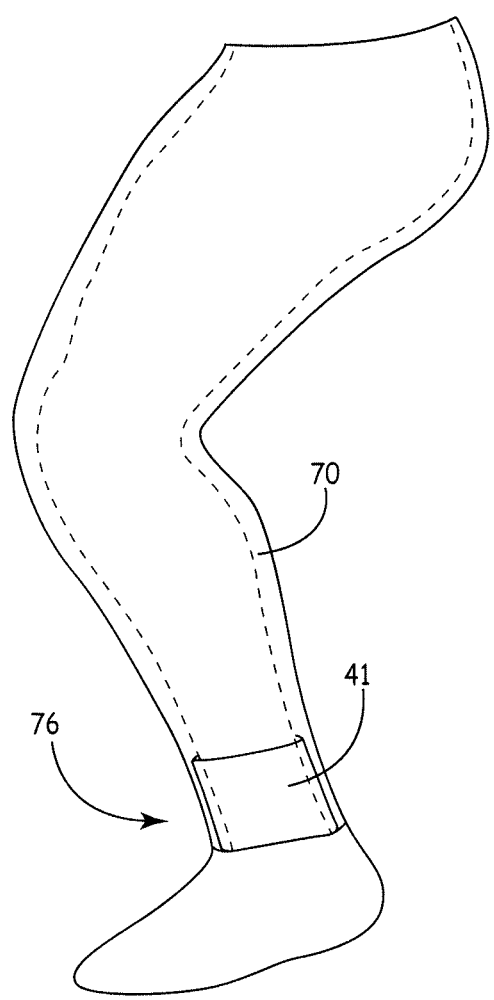
FIG. 11 is a cut-away view of a sleeve seal for the body suit of FIG. 10.

Still another embodiment of a differential pressurize suit 70 is depicted in FIG. 10. In this particular embodiment, the suit extends from the waist 72 to the ankles 74 without covering the feet, and is sealed at the ankle. The waist seal is as described above, and may include a rigid band 54 surrounding an air bladder. The ankle seals 76 are shown in greater detail in FIG. 11, and comprise a sleeve seal 41 connected inside the suit leg 70 that is constructed of elastic neoprene, or another airtight elastic material, such as rubber, latex, or a rubber-coated Lycra. The sleeve seal 41 can be a tight-fitting, airproof neoprene compression sleeve that provides a tight fit over the ankle and lower calf. The sleeve seal 41 should be long enough to provide for a sufficiently airtight closure between the seal and the body skin. The unstretched circumference of the ankle sleeve seal 41 should be less than the circumference of the ankle and lower calf, so that when the sleeve seal 41 is secured around the ankle, a positive pressure is applied by the seal to the underlying skin by the elastic tension of the seals. In this manner, when the suit is pressurized with air to pressure condition P, the pressurized air is substantially contained within the suit 70.

By having suit 70 end at the ankles, motion by the foot will not be impaired by the foot portion of the suit. The suit 70 may also be put on more easily. Moreover, the wearer may wear normal-sized shoes.

The net upward force provided by pressurized air contained within suit 70 may be calculated as:

$$F_b = \Delta P(A_w - 2A_A)$$

where $\Delta P$ is the difference in pressure level P inside the suit and atmospheric pressure $P_{atm}$ outside the suit. $A_w$ is the cross-sectional area of the waist. $A_a$ is the cross-sectional area of each ankle.

Figure 12:
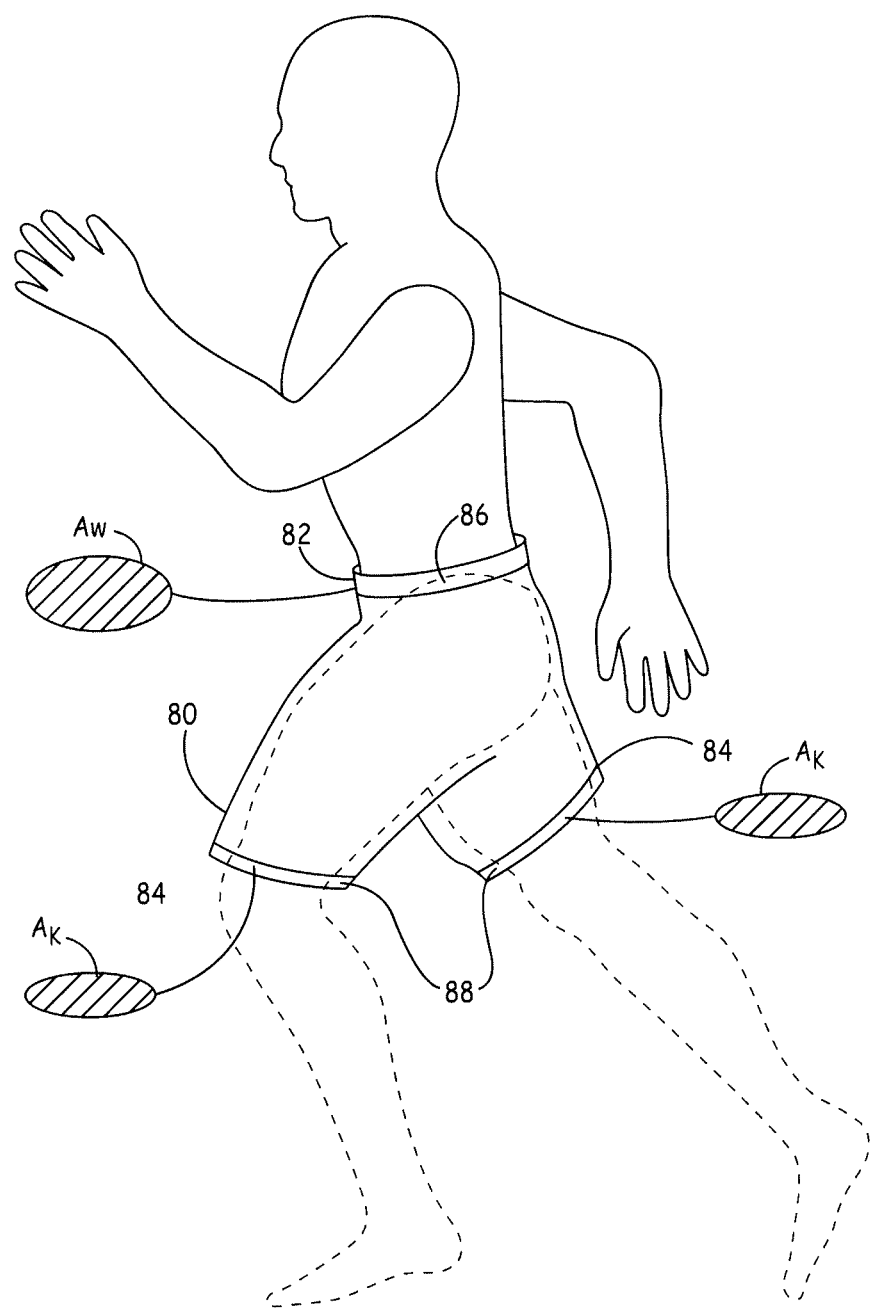
FIG. 12 is a perspective view of a human wearing a pants body suit only extending to just above the knees.
Figure 13:
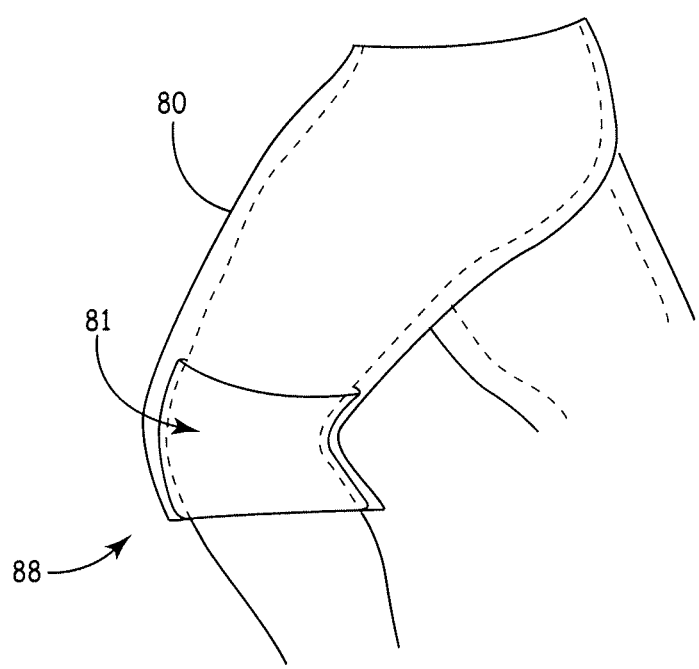
FIG. 13 is a cut-away view of a sleeve seal for the body suit of FIG. 12.

Another embodiment of differential pressurized suit 80 is shown in FIG. 12. In this embodiment, suit 80 extends to just above the knee. It is sealed at the waist 82 and at the knees 84. The waist seal 86 is as describe above. The knee seals 88 are shown in greater detail in FIG. 13. The sleeve seal 81 is an airtight sleeve connected to the interior of the suit 80 that fits tightly over the lower thigh. The sleeve seal should be long enough to provide for a sufficiently airtight closure. The circumference of the knee sleeve seal 81 should be less than the unstretched circumference of the lower thigh, so that when the seal 81 is secured around the knee, a positive pressure is applied by the seal to the underlying skin. This sleeve seal 81 is preferably constructed of elastic neoprene, or any other air-tight material, such as rubber, latex, or rubber-coated Lycra. An advantage provided by this suit 80 is that the runner's knee and lower leg are free to move without any restriction posed by suit 80. This suit 80 is also easier to put on and take off.

The net upwards force supplied to the runner's body when suit 80 is filled with pressurized air is:

$$F_b = \Delta P(A_w - 2A_k)$$

$\Delta P$ is the difference in pressure between pressure condition P contained inside the suit 80 and atmospheric pressure $P_{atm}$ existing outside the suit 80. $A_W$ is the cross-sectional area of the waist. $A_K$ is the cross-sectional area of the spot on each leg just above the knee where seals 88 engage the leg.

Figure 14:
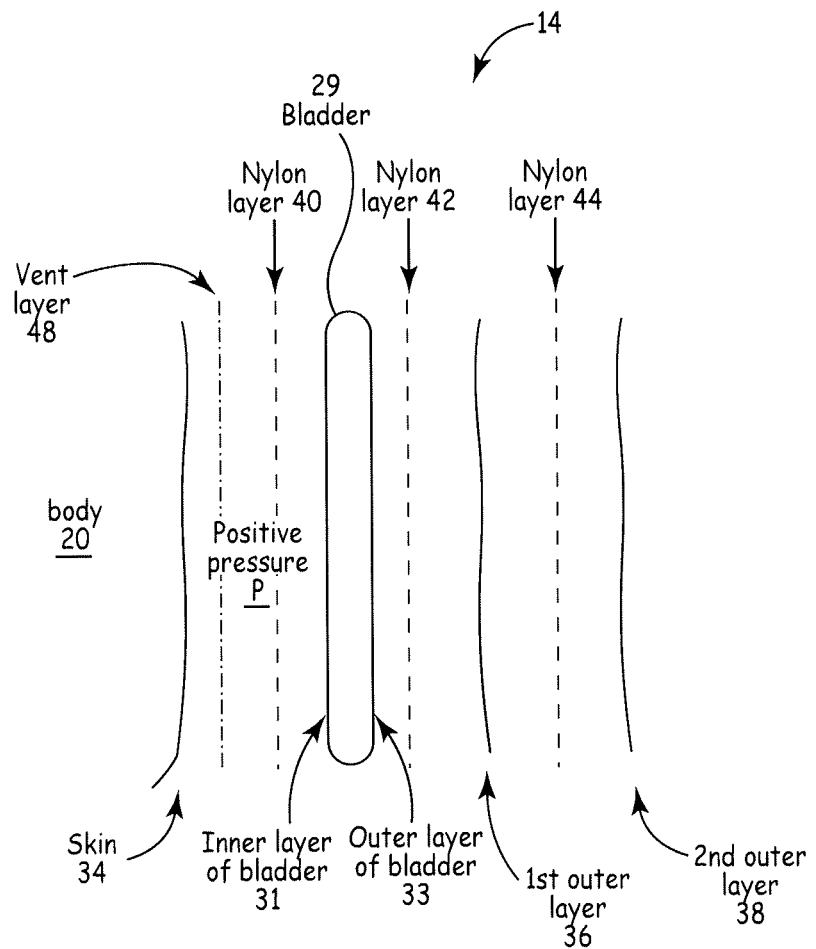
FIG. 14 is a schematic view of the body suit construction further comprising an airtight bladder sealing means.
Figure 15:
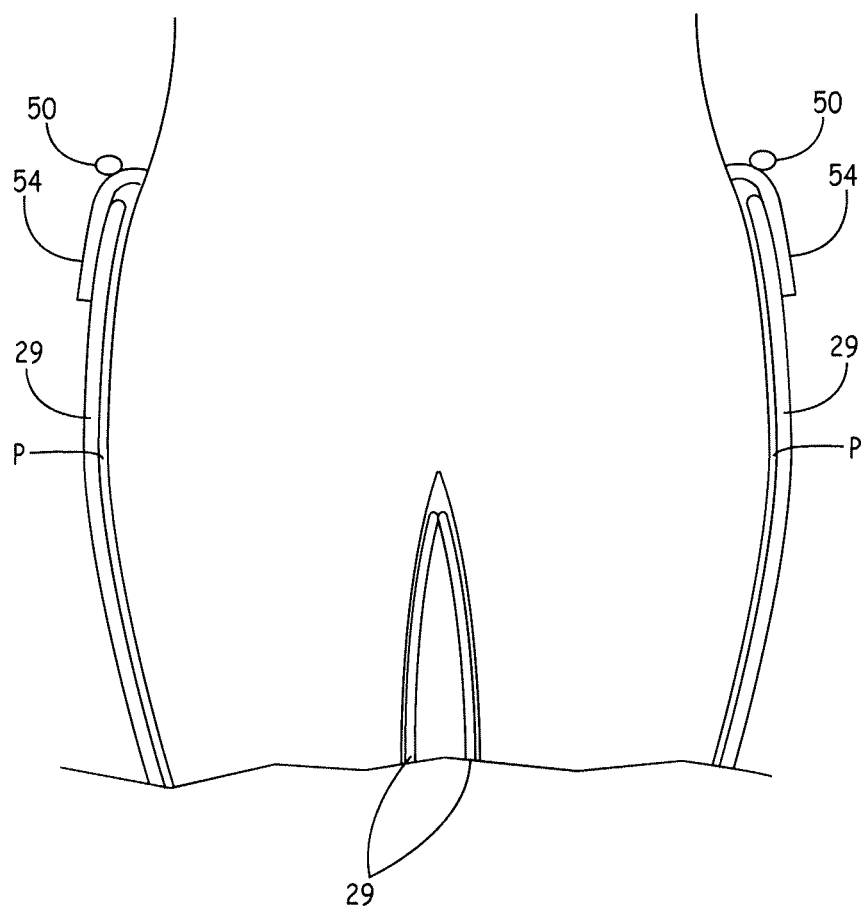
FIG. 15 is a front partial view of the air bladder construction of FIG. 14.
Figure 16:
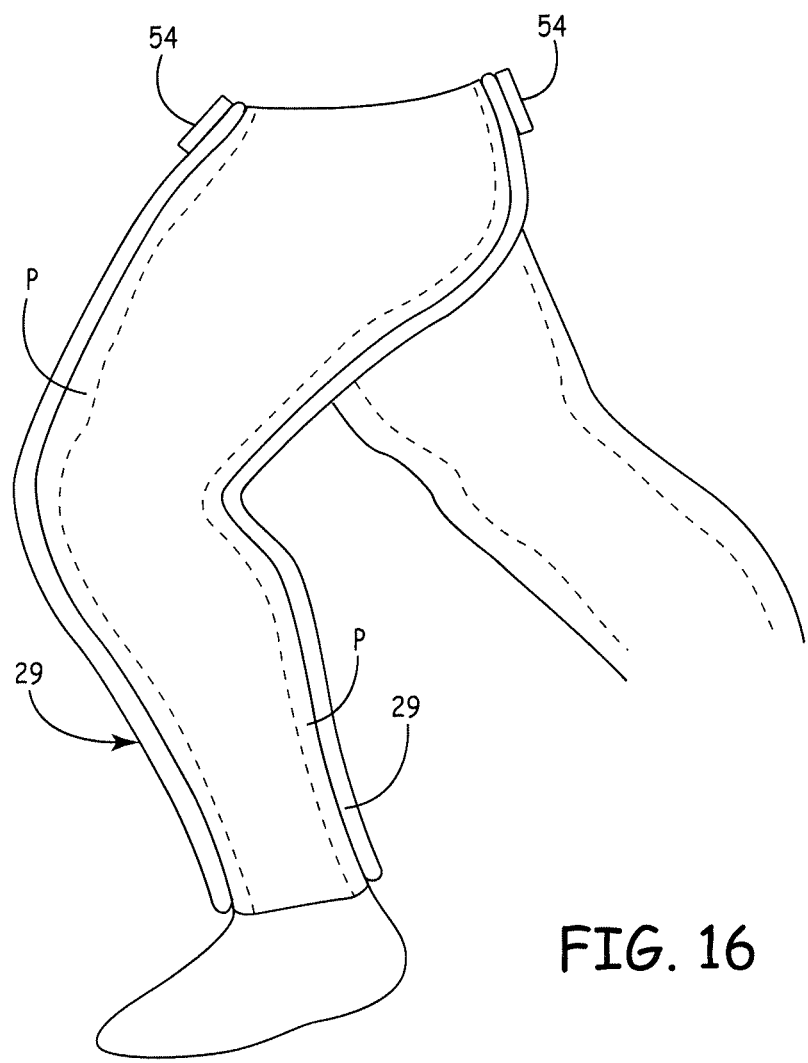
FIG. 16 is a side partial view of the air bladder construction of FIG. 14.

In another embodiment shown in FIG. 14, the pressurized air is contained within the body suit by means of an air-tight bladder 29 illustrated in an expanded view of the layers of the suit. The bladder consists of an airproof inner layer 31 and outer layer 33. The two layers are joined at the top and bottom of the suit to form an air-tight bladder. This bladder is essentially two identical air-proof layers, nested one inside the other, and sealed together at the top waist area and bottom of each leg of the suit. When pressurized, the inner layer presses against the skin and the outer layer presses against the outer constraining layers 36 and 38. A frontal view of the bladder 29 is shown in FIG. 15. A side view of the bladder is shown in FIG. 16. The bladder 29 contains air at pressure condition P. The bladder may be used for the various embodiments of the pressure suits described herein, including a bladder that extends from the waist to around the foot, a bladder that extends from the waist to the ankle, and a bladder that extends from the waist to above the knee.

Figure 17:
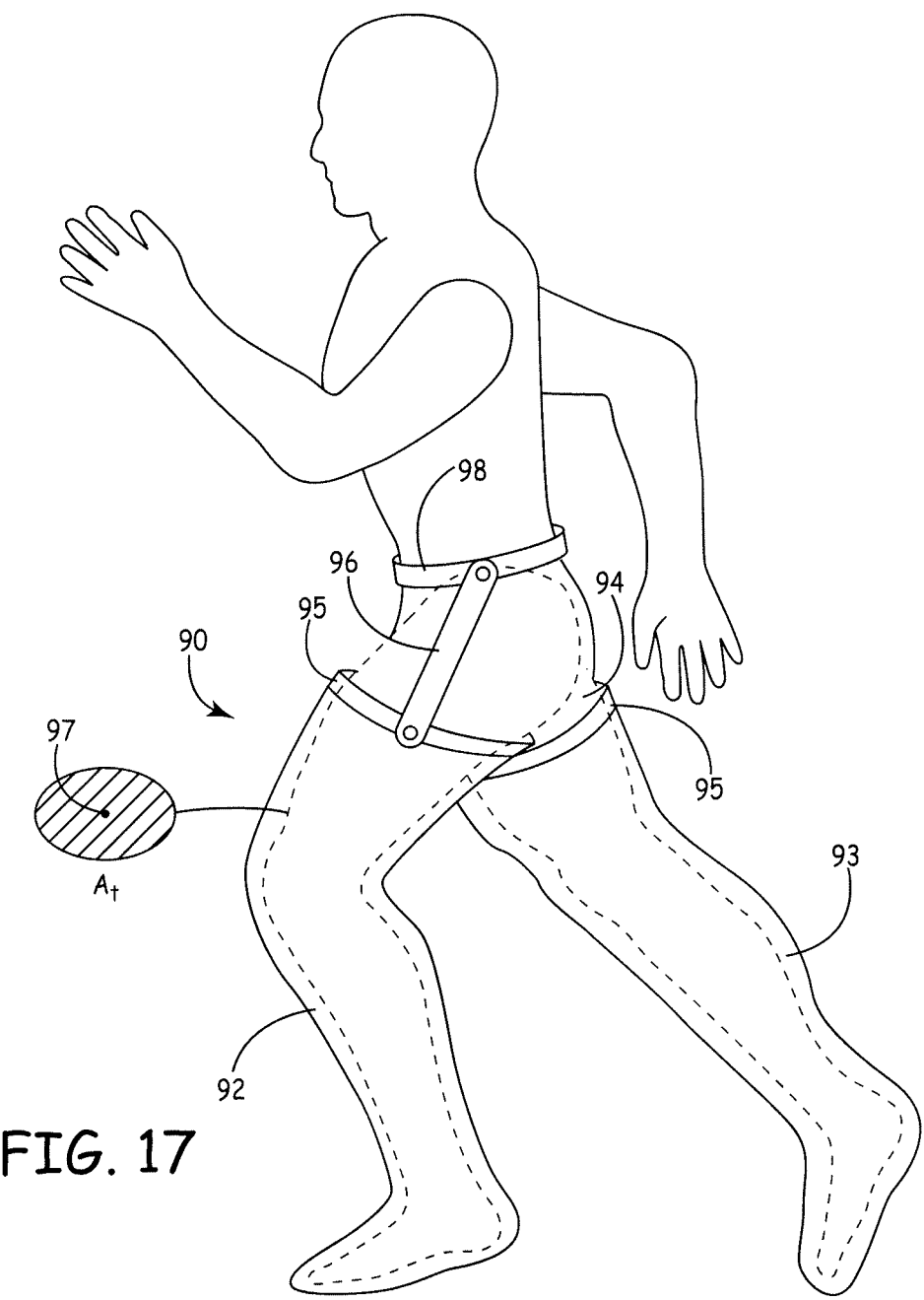
FIG. 17 is a perspective view of an alternative embodiment of the body suit comprising separate pressurized leg units.

Yet another embodiment is shown in FIG. 17 of differential pressurized suit 90. This embodiment consists of an independent suit 92 and 93 for each leg, having leg openings 94 near the upper thigh. The upper thigh seals 95 can extend diagonally from the upper thigh at the groin on the inner side of the leg to the hip on the outer side of the leg. $A_t$ is the cross-sectional area of the spot on each leg at the upper thigh where seals 95 engage the leg.

Each leg suit 92, 93 covers the entire lower leg and foot, so that the entire leg below the thigh seal 95 is airtight. The leg suits are attached by means of straps 96 to a rigid band 98 that is provided near the waist. This band may alternatively constitute a strong, flexible fabric. The band 98 is then attached to a supporting structure (not shown). Alternatively, the leg suits may be attached directly to the support frame by means of straps 96. The positive pressure differential $\Delta P$ contained in the leg suits 92, 93 results in an upwards-directed resultant force $F_b$ applied to the body located at the centroid 97 of the cross-sectional area $A_t$. The total amount of this upwards force $F_b$ on the body from both leg suits is:

$$F_b = 2\Delta P \times A_t$$

where $\Delta P$ is the difference in pressure between the positive pressure P condition inside the suit and atmospheric pressure $P_{atm}$ outside the suit. $A_w$ is the cross-sectional area of the waist region. $A_t$ is the cross-sectional area of each upper thigh region.

The various configurations of suits described above provide high to lower amounts of upwards force $F_b$ on the body, depending upon the location of the seals. The complete lower body coverage suit 14 of FIG. 1 provides the greatest upper lift to the body, because:

$$F_b = \Delta P \times A_w.$$

The waist-to-ankle suit 70 of FIG. 10 provides the next largest amount of lift, because:

$$F_b = \Delta P(A_w - 2A_a).$$

Next in decreasing progression is the waist-to-just-above-the-knee suit 80 of FIG. 12, because:

$$F_b = \Delta P(A_w - 2A_k).$$

For most humans, their body anatomy is such that $A_a < A_k$. The independent leg suits 92, 93 also provide for a higher to lower amount of upwards force on the body. The leg suit with a top seal at the upper thigh of FIG. 17 provides the highest amount:

$$F_b = 2\Delta P \times A_t.$$

A leg suit with a top seal at the upper thigh and a bottom seal at the ankle (not shown) provides the next highest amount:

$$F_b = 2\Delta P \times (A_t - A_a).$$

A leg suit with a top seal at the upper thigh and a bottom seal at the spot above the knee (not shown) provides the lowest amount:

$$F_b = 2\Delta P \times (A_t - A_k).$$

Figure 18:
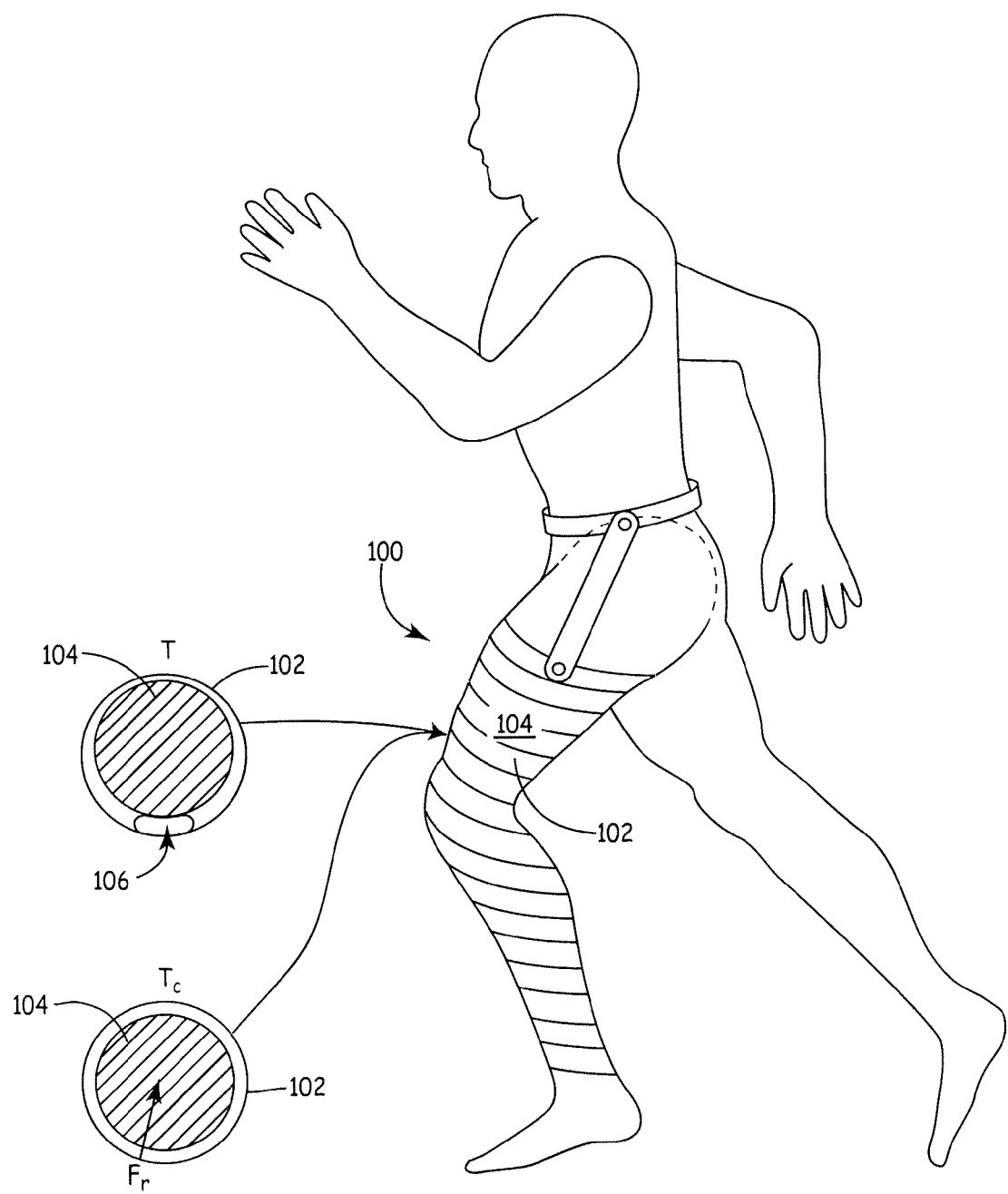
FIG. 18 is a partial perspective view of an alternative embodiment of the body suit comprising a circumferential tension system.

While pressurized gases like air have been discussed as the pressurizing medium for the differential pressurized suit 14 of this invention, positive pressure applied against a body and its limbs can be created by other means. For example a fabric or elastic material 102 circumferentially kept under tension around a leg 104 can be employed, as depicted in FIG. 18. The material 102 exerts a tension $T_c$ that creates an inwardly-directed radial force $F_r$ on the body that is normal to the surface of the leg. The effect of this force within this circumferential tension system 100 is similar to the effect of positive pressure developed by air pressure—i.e., a net upwards force is created on the body.

Various means can be utilized to develop this tension. For example, an elastic material can provide this circumferential tension. In such example, the "suit" is constructed by a multitude of windings of an elastic material that is perpendicular in direction to the axis of the leg 104, and non-extensional in the longitudinal direction of the leg. The suit is sized to be smaller than the body, so that a tension is developed when the suit is put on. Alternatively, the suit can be placed under tension through the use of zippers, or by cinching up the suit via lacing, tied in a knot after it is put on. Suits of this circumferential tension embodiment 100 may be similar in degree of coverage, as discussed above—e.g., waist-to-above-the-knee, waist-to-ankle, waist-to-around-foot; upper thigh/hip-to-above-knee; upper thigh/hip-to-above-ankle; upper thigh/hip-to-around-foot.

An air bladder 106 positioned under a portion of the wrap 102 against the leg 104 may be utilized to create further tension inside the suit 100. This air bladder should have a small width, and extend longitudinally along the body under the wrap 102. When the bladder 106 is inflated with a gas like pressurized air, the wrap 102 is placed under tension. Advantageously, only a small amount of air is required to create the positive pressure on the body, because the wrap 102, itself, also contributes positive pressure via the tension. At the same time, the wrap material can allow for breathability and the transfer of moisture away from the body.

Shaped memory alloys like nickel titanium or shaped polymers may likewise be used to provide the tension in a circumferentially-tensioned pressure suit. An electric current can be applied to cause the material to change in shape to conform to the underlying body's shape, and create circumferential tension. Shaped memory alloys or polymers can be woven into fabric that the suit is constructed of.

Figure 19:
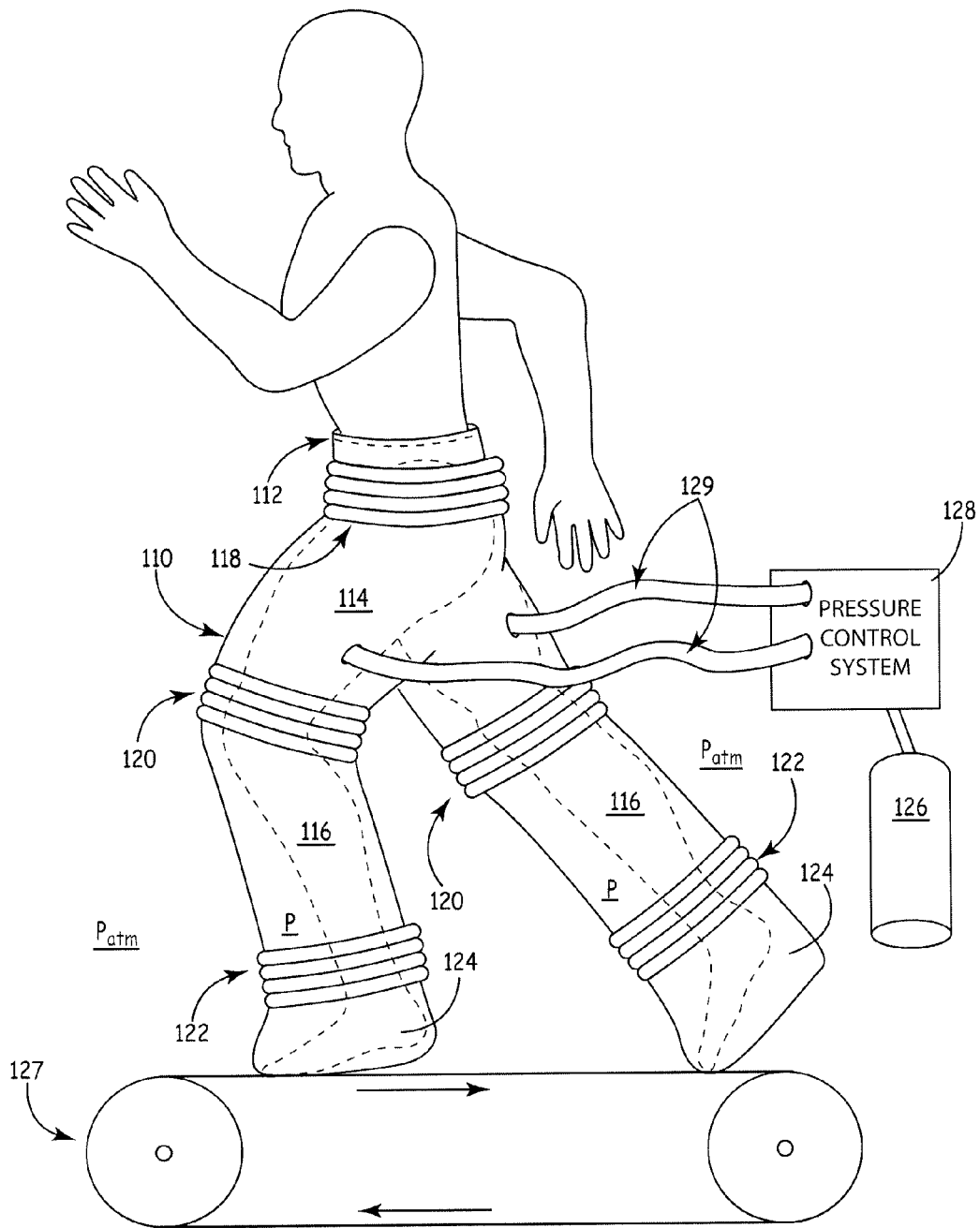
FIG. 19 is a perspective view of an alternative embodiment of the body suit comprising a loose-fitting body suit.

While close fitting differential pressure suits 14 and circumferentially-tensioned suits 100 have been described for use with the assisted motion system 10 of the present invention, a looser-fitting suit 110 may also be employed, as shown in FIG. 19. The legs of the suit 110 may extend downwardly to just above the knee, above the ankle, or cover the entire foot, as described above. Seals 112 can be provided around the waist and at the bottom edges of the suit if the suit does not extend around the feet. Exemplary locations include: upper seals 112 at the waist or upper-thigh-to-hip; lower seals at above the knee or above the ankle.

Mobility of the body 114 and lower legs 116 is provided by constant volume joints positioned at the waist 118, knee 120, and ankles 122, respectively, of the suit 110. The equation for work where volume is changed under a constant pressure is:

$$W = P \times \Delta V$$

where W is work, P is the constant pressure, and $\Delta V$ is the change in volume. Clearly, holding the volume constant in a joint, such that $\Delta V = 0$ over the course of joint flexure is one way to nullify the need to expand work just to flex the suit joint.

A constant-volume joint allows the cross-sectional area of the joint of the suit to maintain a constant volume of pressurized air P during bending of the body, so that the work, and thus the force, required to bend the joint is minimized. In the preferred embodiment of loose-fitting differential pressure suit 110, the constant volume joints consist of baffles and tensioning straps along the sides of the joint to prevent the baffles from extending. Other types of constant-volume joints known in the prior art, such as "Space Suit Mobility Joints described in U.S. Pat. No. 4,151,612, and which is hereby incorporated by reference in its entirety, may also be utilized. The suit shown in FIG. 19 has constant volume joints positioned at the waist-through-the-hip section and at the knee. A constant volume joint at the knee 120 allows the leg to bend and move at the knee with the motion of walking or running without the need for undue force. An airproof boot 124 is worn and the constant volume joint 122 is utilized to allow for mobility.

Pressurized gas 126, such as air, is injected into the suit 110 by means of control system 128 and hoses 129. A person wearing the suit 110 may exercise on a treadmill 127, but portable pressurized gas systems are also possible.

A rubberized nylon can be utilized to construct a single-layer suit. This can be sewn into the appropriate shape using a standard sewing machine. Thigh seals can be made from a commercially-purchased neoprene compression sleeve. Compression sleeves are available from Advanced Brace of Irving, Tex. Neoprene compression shorts are available from the same supplier. The compression sleeve can be sewn interior to the pant around the thigh opening, and made airtight with seam sealer in the form of Seam Lock sold by REI, Inc. of Sumner, Wash. to make the seam airtight. A shorts-type waist seal can be constructed by sewing the waist area to the outer rubberized nylon suit, and sealing the seams to make it airtight. Alternatively, a compression sleeve may be connected to the rubberized nylon exterior suit, by placing each over an appropriate diameter steel band, and then clamping together the two layers of material with another outer ring. A standard air intake fitting can be installed in the pants to provide a port for pressurizing the suit.

Another important aspect of the assisted motion system 10 of FIG. 1 is the external support structure 26 that is necessary for preventing the downwardly directed force $F_s$ on the suit created by the positive pressure differential $\Delta P$, from forcing the suit down and off the runner's body. In the case of FIG. 1, the embodiment of external support structure 26 constitutes a frame 28 and wheels 30 for providing complete mobility to runner 12. Such support structures should be designed for the specific range of body motions that the person wearing the suit plans to carry out.

Figure 20:
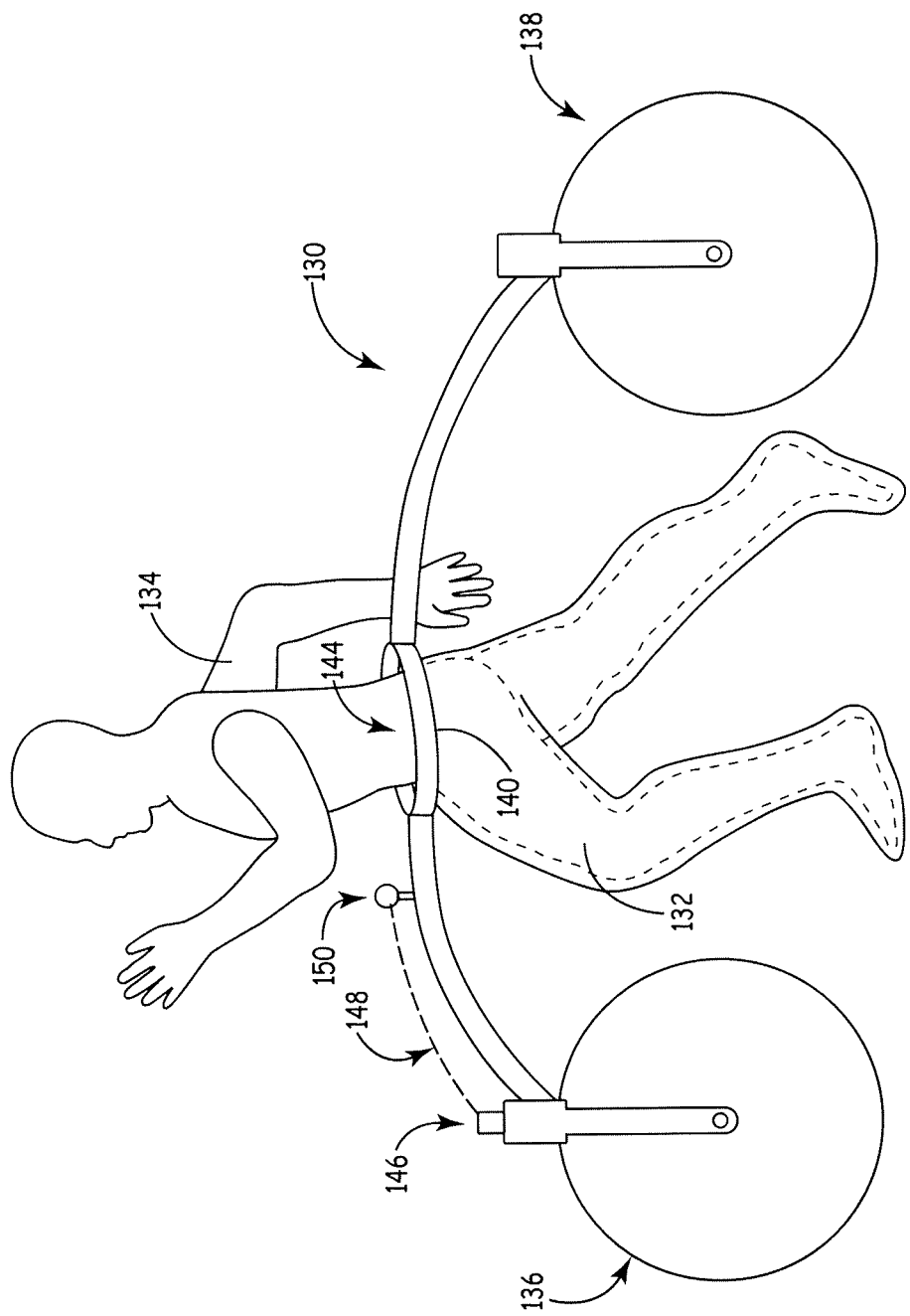
FIG. 20 is a perspective view of an external wheeled frame support structure for the body suit.

Shown in greater detail in FIG. 20 is a wheeled frame structure 130 for supporting a differential pressurized suit 132 worn by a person 134 who is running. As the runner wears this suit 132 supported by the wheeled frame 130 during his running routine, he experiences less weight on his feet, knees, legs, and lower body, because a portion of his body weight has been offloaded by the upwards force $F_b$ on the body created by the positive pressure differential $\Delta P$ of the pressurized suit 132. The downward force $F_s$ on the suit also caused by the positive pressure differential $\Delta P$ is transmitted to the support structure 130, and from the support structure to the ground.

The frame 130 shown in FIG. 20 has a construction similar to a bicycle: a wheel in the front 136 and one in the back 138. The runner 134 is positioned midway between the wheels, and the space between the wheels is sufficient to avoid contact with the runner's legs. The rotational momentum of the wheels stabilizes the frame during motion, as with a bicycle. The frame 130 wraps around the runner 134 at the waist/hip level 140. Note the absence of a seat, pedals, sprocket and chain that are normal to a bicycle. The frame 130 is designed so that the nner 134 can swing his arms and hands when running.

The pressurized suit 132, as described in other embodiments of this invention, will create a force along the vertical axis of pushing the body up, with the reaction force being that of pushing the suit down. The latter is countered in this embodiment by offloading this downward reaction force to the 'bike' frame 130, thereby effectively delivering part of the runner's weight to the bike frame and thus to the ground through the wheels.

A mechanism 144 allows for both rotational and angular pivoting of the runner's torso during the motion of running. In this embodiment, the mechanism simply consists of a flexible pleated material 140 surrounding the region about the waist of the pressure suit, which may bend and twist with the movement of the runner's torso. Other mechanical mechanisms for this purpose may also be utilized.

The running support frame 130 has a mechanism 146 for steering the bike. In one embodiment of the steering mechanism, the movable front wheel 136 is steered in a similar fashion to a bicycle, except instead of long handlebars, cables 148 and a small steering wheel 150 are used employing well-known mechanical methods to implement steering. In a second embodiment of the steering mechanism, a handlebar is brought back in reach of one or both arms of the runner. The only difference in this embodiment and a standard bicycle steering mechanism is that a centering spring holds the bike true, or non-turning until the runner applies force to the steering handle bar. This allows periods of running without active steering. A third steering embodiment uses a stepper motor in the steering column powered by an embedded rechargeable battery. The steering is controlled by the motor via a wireless handheld glove actuator that provides motion commands to the motor using well-known wireless and motion control methods. This permits the runner to freely swing his arms in a natural nnning motion, and still retain full-time steering control. A fourth steering embodiment positions the hub of the wheel backwards or forwards of the vertical axis of steering to provide automatic steering.

The running support frame 130 may also have standard bicycle brakes which are operated by a hand lever using well-known means, or by the handheld remote control method that may actuate electric powered brakes.

An optional constant force extension mechanism may be used that provides a constant upwards force on the pressure suit allowing it to move vertically with the vertical motion of the runner's body. The constant force of the mechanism is adjustable so that the upwards force on the mechanism is equal to the downwards force of the suit under pressure. The suit can thus float vertically up and down with the motion of the runner's torso, while maintaining an essentially constant upward force on the suit. A range of motion of 0-7 inches is provided to accommodate various runners, with 3 to 4 inches being a typical vertical displacement in running motion.

Different frames sizes may be provided to fit different sized runners. The vertical position of the rotational and angular pivoting mechanisms and the constant force may be adjustable to accommodate different body heights.

Figure 21:
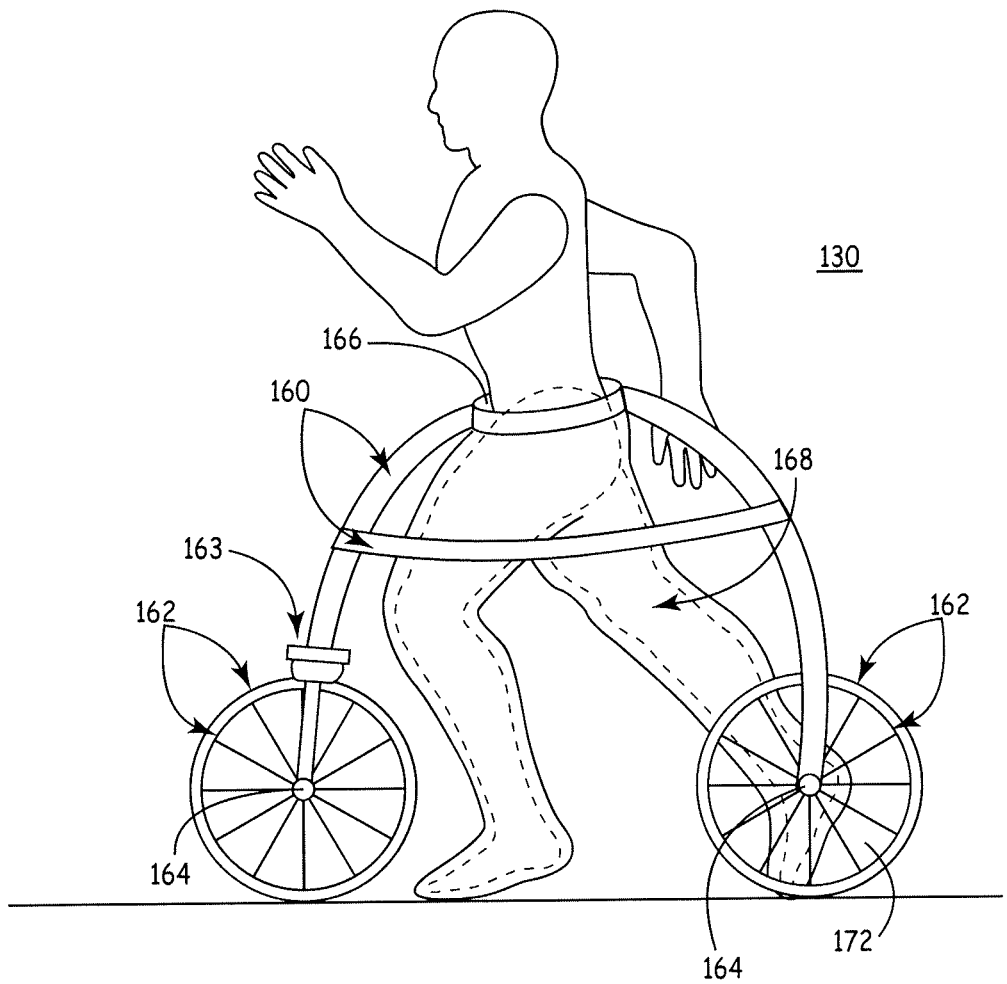
FIG. 21 is a perspective view of an external cart-like support structure for the body suit.

An alternative embodiment to the foregoing bicycle-like running support structure 130 is a cart-like structure with four wheels, arranged as pairs of wheels lateral to the left and right sides of the runner, as shown in FIG. 21. In this embodiment, the frame 160 is connected to each wheel 162 lateral to the runner, leaving a clear path to the front and back of the runner. The front wheels operate independently and are implemented as turnable castors 163 to accommodate steering. The rear wheels also rotate independently, but are fixed on their vertical axis. The axle shafts 164 provide a rigid connection to the interface member 166 for the pressure suit 168. In a manner identical to the bicycle-like embodiment, a portion of the runner's weight is off-loaded via the pressure suit 168, and transmitted to the frame, axle shafts 164, and ultimately the ground 172. Steering is accomplished passively in that the cart simply follows direction changes engendered by the runner's change in direction, which translates twist through the frame to the front wheel castor mechanisms in a manner similar to steering a shopping cart.

Yet another embodiment may be that of a tricycle, where a pair of wheels front-left and front-right of the runner are connected to the frame as in the four-wheeled cart, and a third free wheel and a single free turning rear wheel confers stability to the system. Finally, it should be realized that any number of wheels may be used without departing from the scope of this invention.

Figure 22:
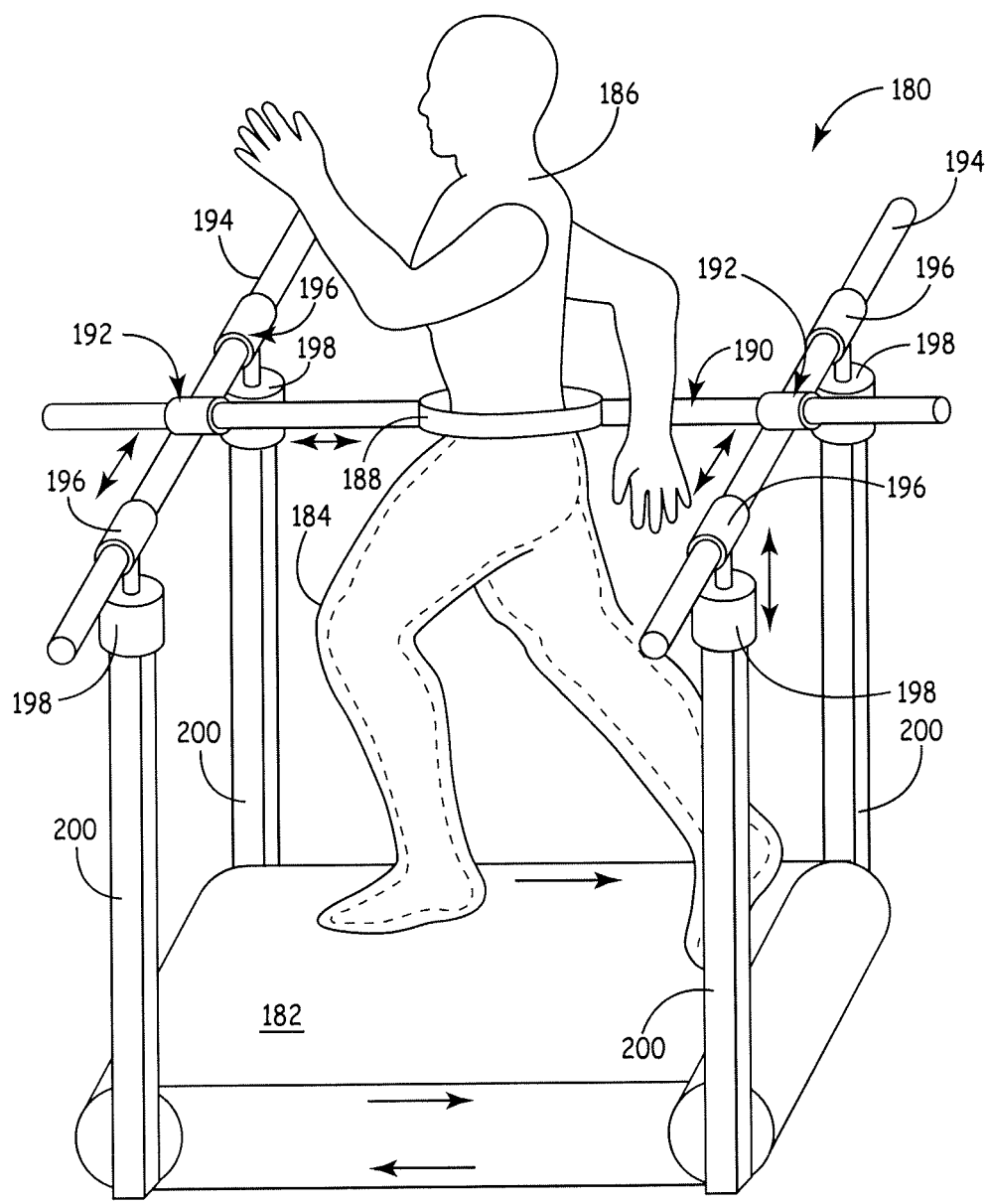
FIG. 22 is a perspective view of a stationary support frame structure for the body suit.
Figure 23:
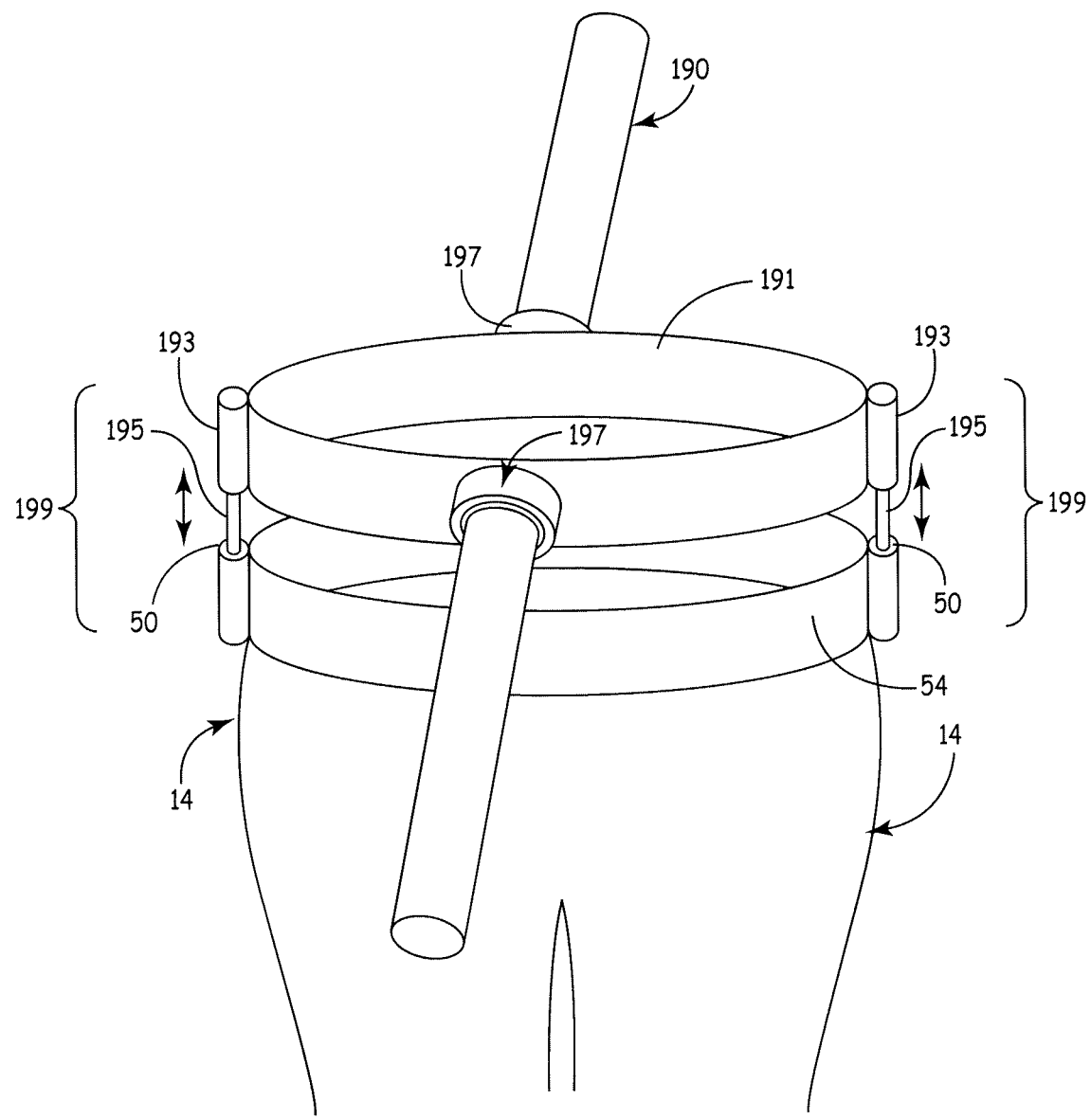
FIG. 23 is a partial perspective view of a constant-force adjustment mechanism for the stationary support frame structure of FIG. 22.
Figure 24:
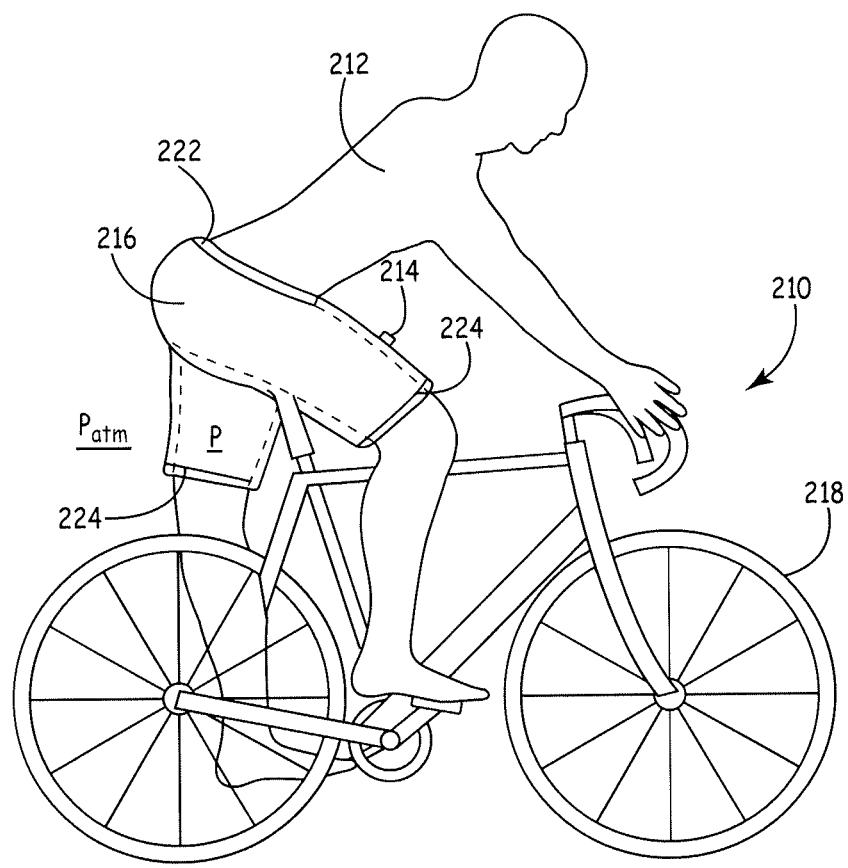
FIG. 24 is a perspective view of an assisted motion system of the present invention for bicycle riders.
Figure 25:
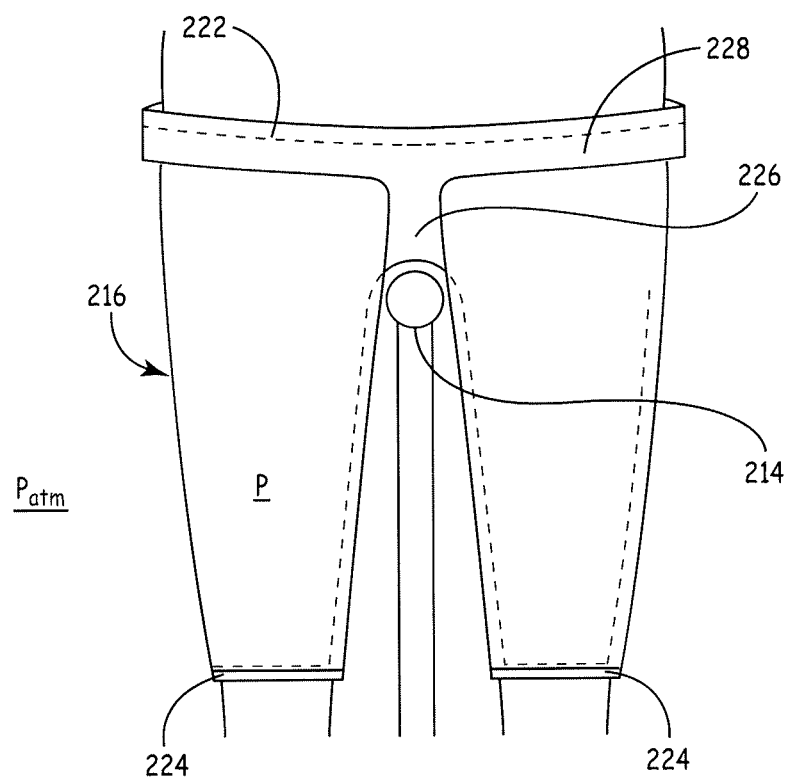
FIG. 25 is a front view of the support structure for the bicycle assisted motion system of FIG. 24.
Figure 26:
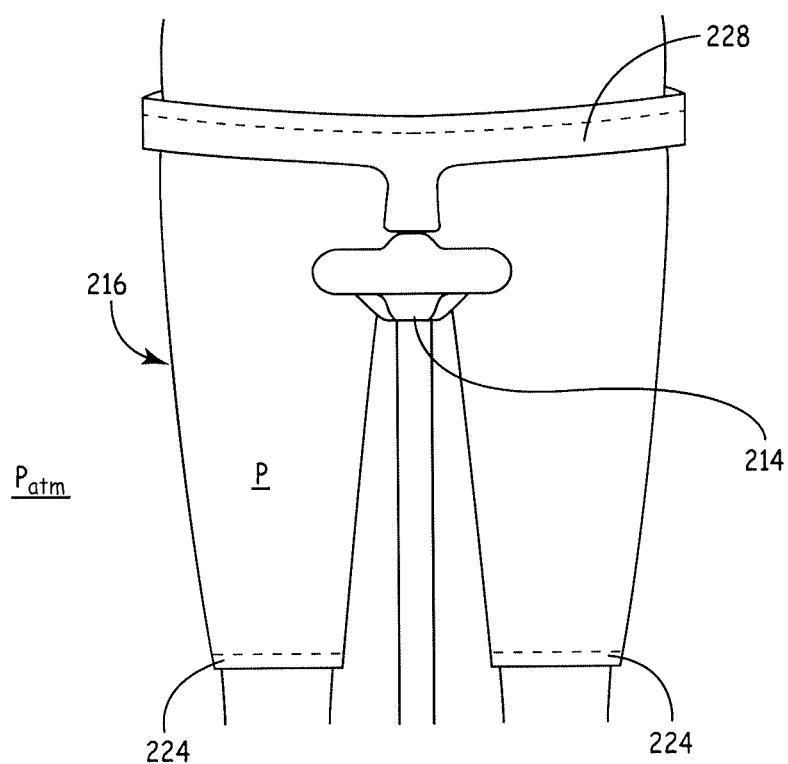
FIG. 26 is a back view of the support structure for the bicycle assisted motion system of FIG. 24.
Figure 27:
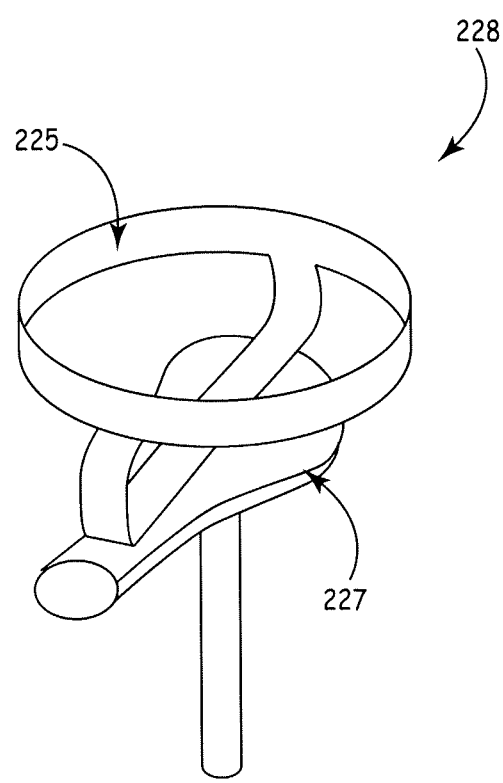
FIG. 27 is a perspective view of the support structure shown in FIGS. 24-26.

FIG. 22 shows another embodiment of the support structure consisting of a stationary supporting frame 180 positioned over a treadmill 182. The frame 180 provides support for the pressure suit 184 worn by the runner 186. Any of the aforementioned pressure suit embodiments may be utilized for this static support structure 180. For illustrative purposes, FIG. 22 depicts a pressure suit 184 that ends above the ankles. Conceptually, the only difference between this static support structure 180 and the aforementioned wheeled support structures 130 and 160 is that the reaction force that is subtracted from the runner's weight is offloaded from the runner to a rigid fixed structure, the treadmill frame, instead of a mobile structure.

This is accomplished by providing a set of sliding rods which support the runner and are arranged to allow for longitudinal and lateral motion. A rigid waist loop supporting member 188 wraps around the runner's body and connects to the pressure suit 184 at the waist. A horizontal longitudinal sliding rod 190 connects to each end of the frame and slides through the fittings 192. The sliding longitudinal rod allows for longitudinal movement of the runner in the front to back direction on the track 182. The fittings 192 are attached at the middle of each of two sliding horizontal lateral rods 194. These sliding lateral rods allow for lateral movement of the runner on the track in the side-to-side direction. The lateral sliding rods 194 slide through fittings 196 that are fixed atop constant-force pneumatic springs 198. Preferably, these springs provide a constant force to support the vertical downwards loads from the suit and sliding rods, and allow for vertical motion of the runner 186. In other embodiments, the springs may be constant-force mechanical springs, as is known in the art. The springs may also be mechanical or pneumatic springs that are not constant force. The springs are connected to vertical rigid members 200 that connect to the base of the treadmill.

In usage, the constant-force air cylinders are each set such that the total force equals the desired weight to be subtracted. Air cylinder actuators are available from Bimba Manufacturing Company of Monee, Ill. Prior to pressurizing the pants 184, the runner steps up on a small support about one foot above the surface of the treadmill, and clips into the hooks on the air cylinder apparatus. Once this is done, the pants 184 may be pressurized. By standing on a scale, the pressure may be set to subtract the desired weight. Alternatively, since the pants characteristics should be known a priori, a specific calculated pressure P applied to the pants 184 will yield a specific weight subtraction. The desired weight subtraction set via the pressure P, and the counter force supplied by the air cylinders 198 can be approximately matched. A control system can apply the correct calculated pressure to the constant force springs 198. During running, a runner could move vertically from 1 to 7 inches, typically 3 or 4 inches, vertically relative to the running surface. The function of the air cylinders 198 is to maintain a constant offloading of the reaction force dynamically, in response to this vertical displacement during running.

In lieu of the wheeled or static support structure discussed above for this invention that is separate from the pressurized suit, the supporting structure component may be directly incorporated into the pressure suit so that both the supporting frame and the pressure suit and body have the same movements. In this manner the invention provides for a wide range of movements and exercises over a variety of terrains.

Figure 28:
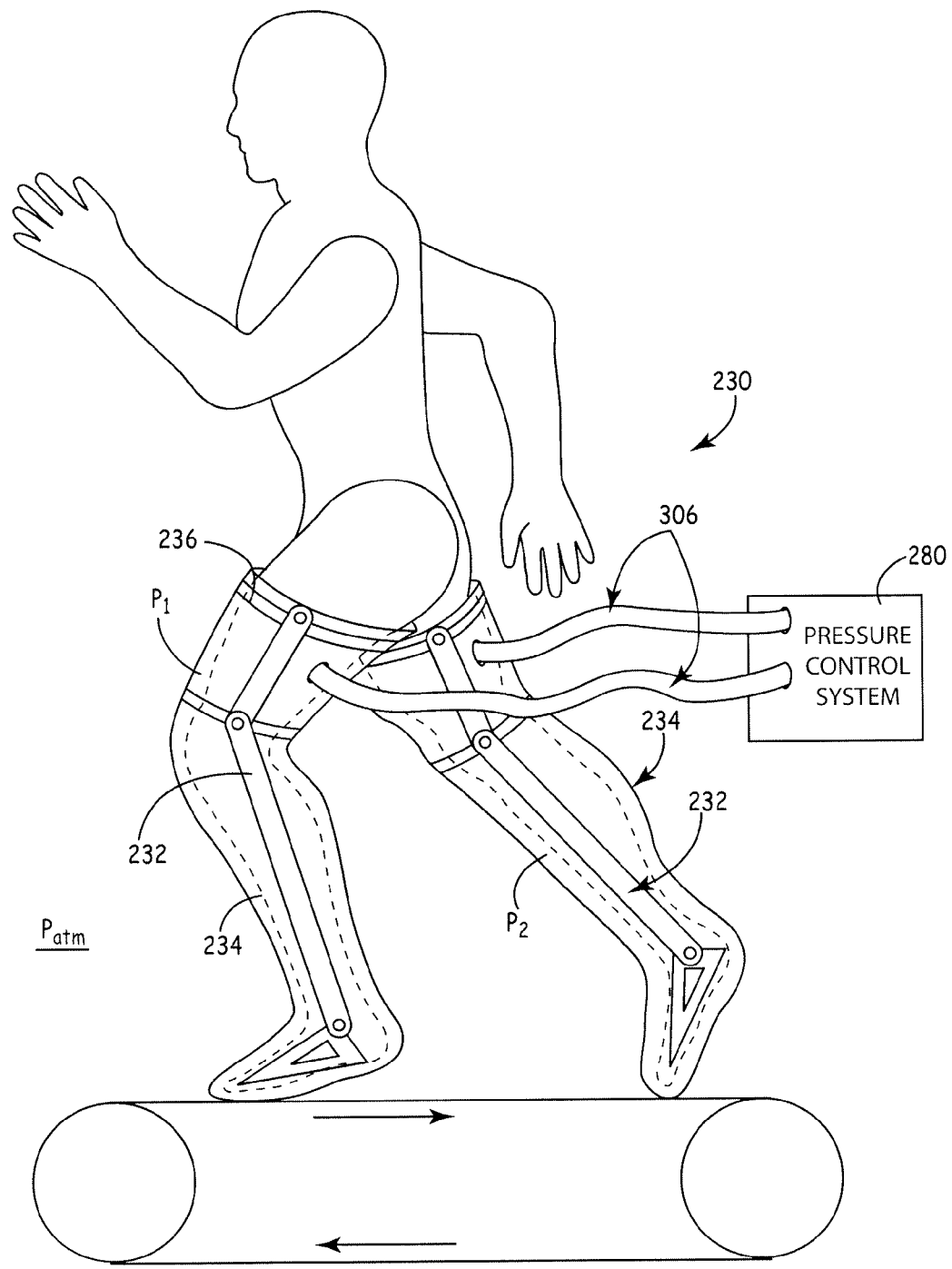
FIG. 28 is a perspective view of an external exoskeleton support structure for the body suit of the present invention.

As shown in the embodiment 230 of FIG. 28, the supporting frame is a rigid exoskeleton structure 232 made of lightweight rods and joints that is attached to the outside of the pressurized suit 234. The rigid frame and joints of the exoskeleton 232 provide the necessary support for the downward force of the pressurized suit 234. The downward force of the suit $F_d$ is equal to the upward force $F_u$ at the attachment point to the top of the exoskeleton. The exoskeleton has matching supports on the inside and the outside of the legs.

Figure 29:
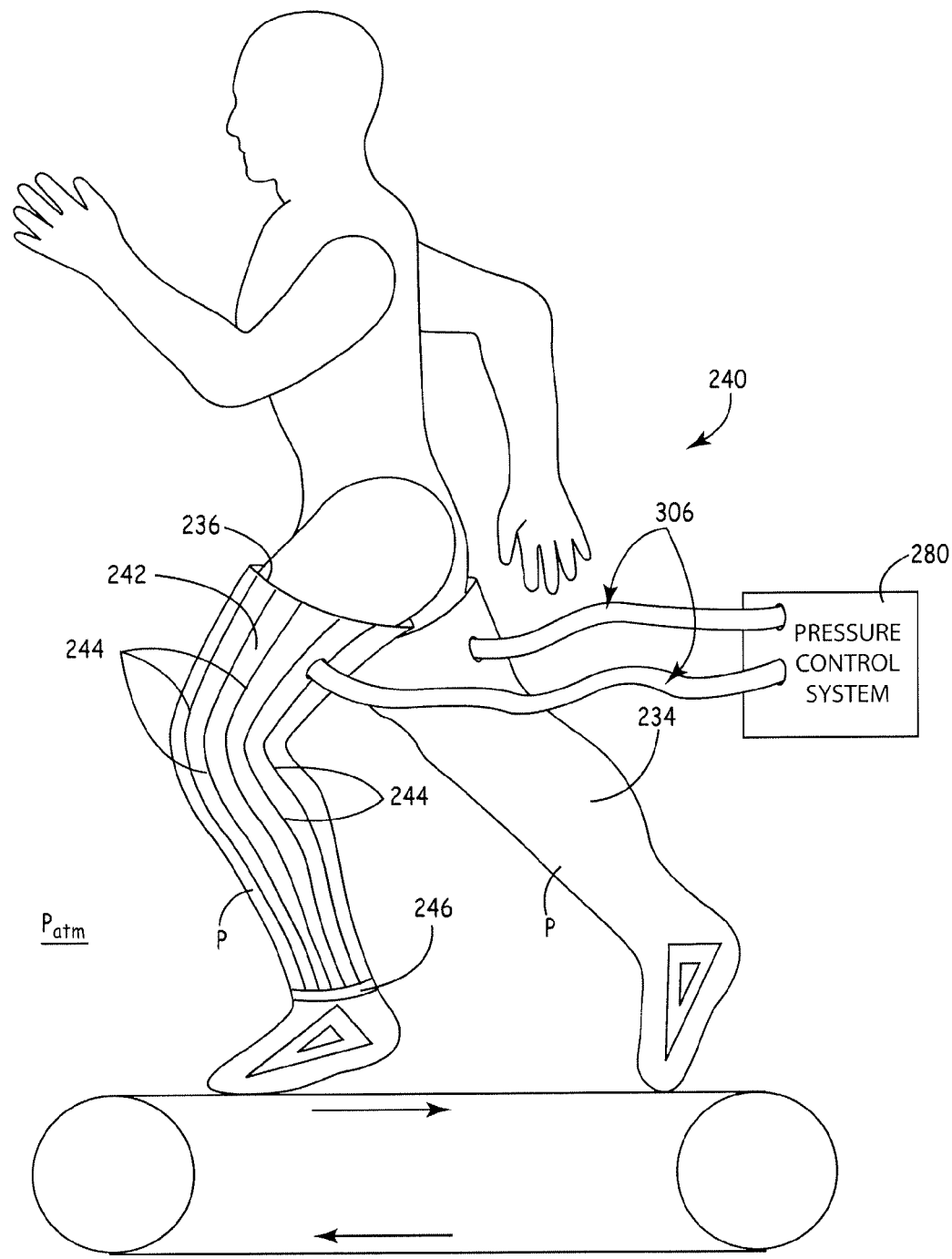
FIG. 29 is a perspective view of an internal exoskeleton support structure for the body suit of the present invention.

The embodiment 240 shown in FIG. 29 is the same as that shown in FIG. 28, with the exception that the rigid exoskeleton 242 is built into the fabric of the suit. The exoskeleton 242 comprises a number of relatively strong thin vertical rods 244 that have a flexible joint at the knee. The rods are integrated into the air-tight fabric that comprises the suit 234 as described earlier, and terminate uniformly at an ankle ring 246 that in turn conducts the force to the exterior of the boot structure and thus to the ground. Alternatively the rods 244 may be layered over the suit and suitably attached at a multitude of points. The rods generally follow the longitudinal lines of non-extension of the lower body and legs. The rods 244 are comprised of a suitable lightweight, but strong material such as aluminum or a composite material. The internal exoskeleton 242 supports the legs of the pressurized suit 234. It is depicted inside only one leg in FIG. 18 for ease of understanding.

Another type of supporting device for the assisted motion system 10 of the present invention utilizes the air pressure of the pressurized suit to support the runner. In this case, no supporting frame is required. The column of pressurized air contained in the leg units is capable of supporting a load equal to the differential pressure $\Delta P$ times the cross-sectional area of the leg unit $A_u$.

Figure 30:
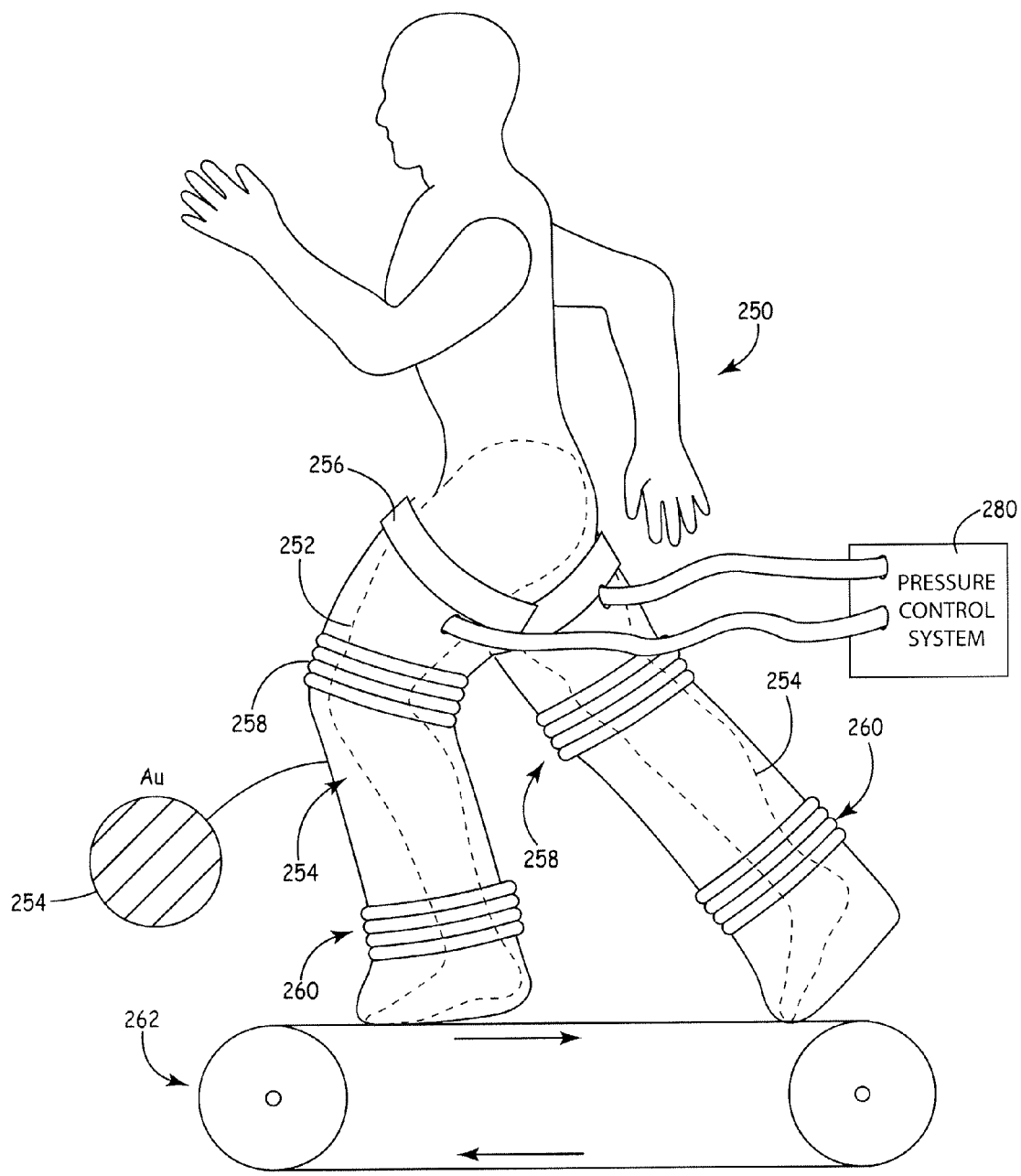
FIG. 30 is a perspective view of pressurized body suit units which provide the support structure for the body suit.
Figure 31:
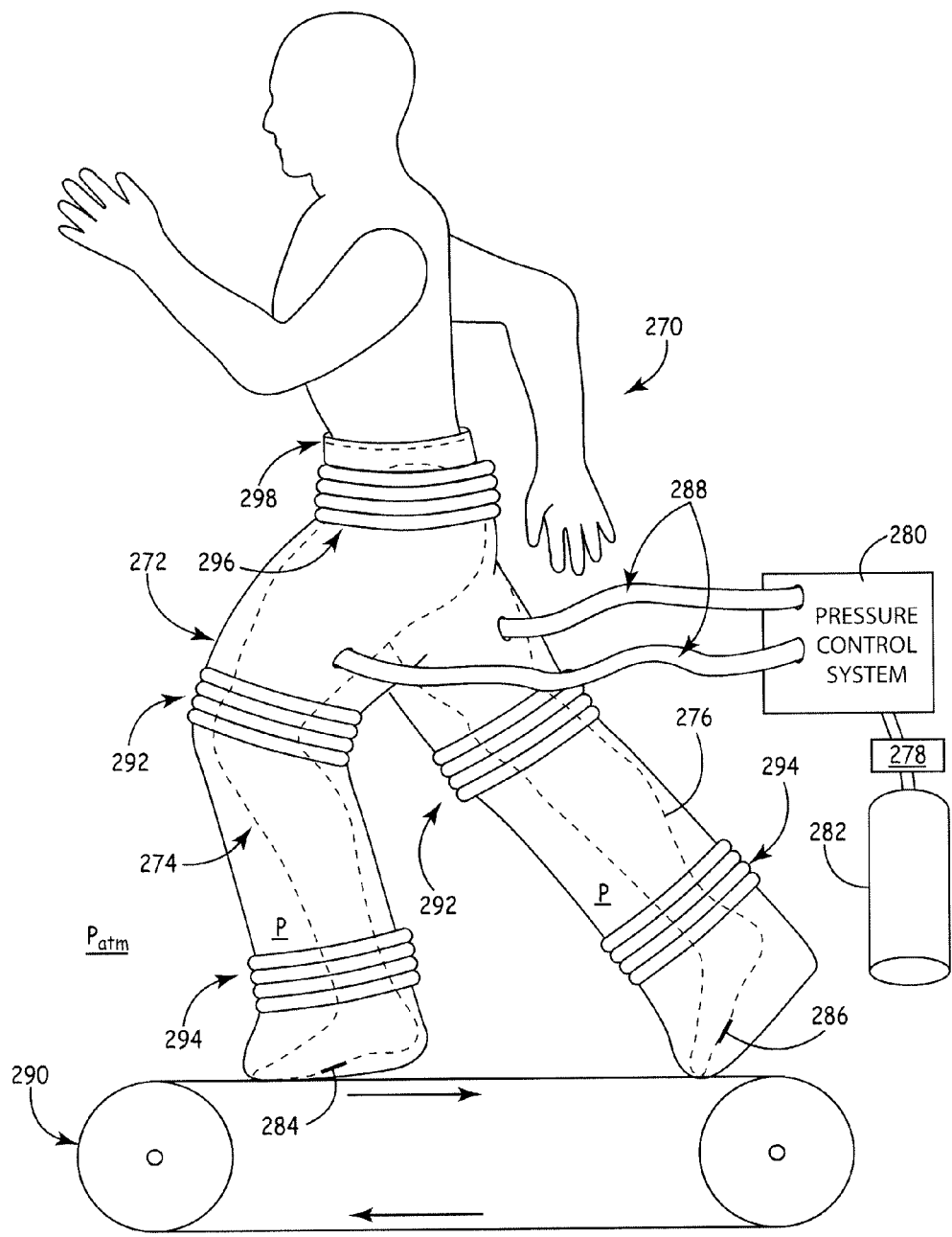
FIG. 31 is a perspective view of a loose-fitting body suit of the present invention featuring a cyclic gas pressurization/depressurization system for supporting the body suit.
Figure 32:
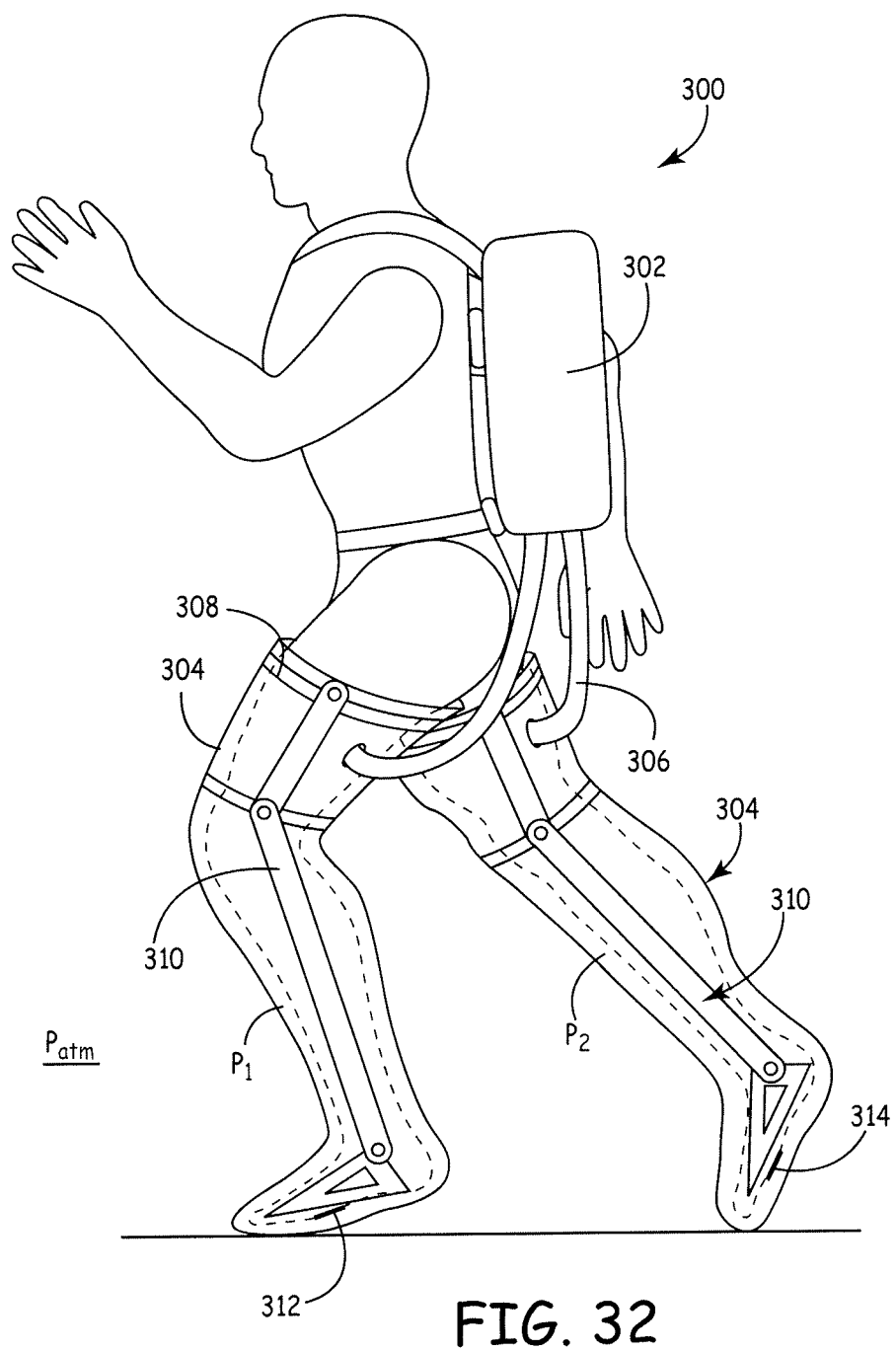
FIG. 32 is a perspective view of a portable cyclic gas pressurization/depressurization system for supporting the body suit also supported by an external exoskeleton system.
Figure 33:
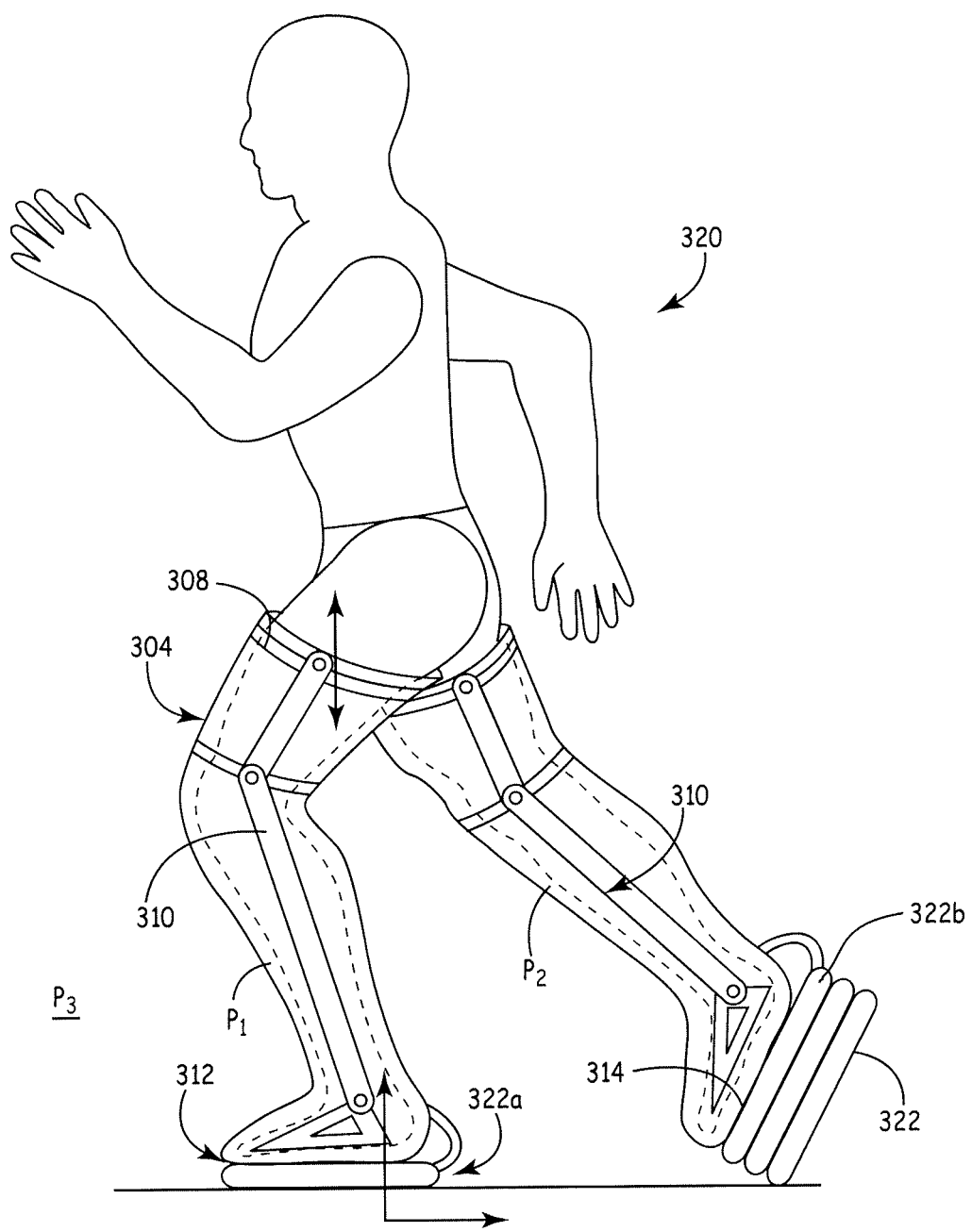
FIG. 33 is a perspective view of the portable cyclic gas pressurization/depressurization system for supporting separate pressurized body units also supported by an external exoskeleton system.

As shown in FIG. 30, in this embodiment 250 the body suit 252 consists of tubular units 254 around each leg. The leg units have an equivalent or slightly increasing cross-sectional area from the top to the bottom. This shape of the tubular units 254 results in no vertical downwards force being imparted on the exterior of the tube by the internal pressure of the unit. The units are sealed at the bottom around the foot. The units are sealed at the top against the thigh by seals 256, as described previously. The units are sized, so that the column of pressurized air can support the weight of the body that is supported by the internal differential pressure $\Delta P$. The load supported by each unit is equal to the cross-sectional area of the unit $A_u$ times the differential pressure $\Delta P$.

The positive pressure differential $\Delta P$ in the leg unit results in an upwards-directed resultant force $F_b$ on the body located at the centroid of the cross-sectional area $A_u$ of each leg unit. The total amount of this upwards force $F_b$ on the body from a leg unit is:

$$F_b = \Delta P \times A_u.$$

As discussed with respect to FIG. 30 for the loose-fitting suit embodiment of the pressurized suit, constant volume joints 258 at the knees and 260 at the ankles allow the pressurized leg units 254 to bend and move with the walking and running motion without the need for undue force. Loose fabric in these joints permit the volume to remain relatively constant during bending. A retaining means between the loops of fabric prevent the joint from expanding longitudinally when the tubular units 254 are pressurized. The person can conveniently exercise on a treadmill 262.

In another embodiment, the tubular units may be shaped into forms that enable the motion of the person wearing the suit 252, and provide for a more compact design. For example the tubular units may be elliptical with the longer axis aligned with the forwards-backwards axis of motion. The shape of the cross-sectional area can vary moving up and down the leg. The lower cross-sectional area can be shaped more like the lower leg and foot. The upper cross-sectional area can be shaped like the thigh. This provides for a streamlined form, which does not interfere with the running motion.

Alternatively, the tubular unit may have a separate outer pressurized chamber that provides the support. This chamber can have a higher pressure than required for providing support to the body to enable supporting a higher load with less of a cross-sectional area for the tubular unit.

The unit may also have separate smaller pressurized tubular units which support the load. Such an embodiment provides a more compact form closer fitting to the body.

For the suits described which provide exoskeletons as the supporting structure, the movement of various body movements can be further enhanced by using a powered exoskeleton, as is known in the art. A powered exoskeleton consists primarily of a skeleton-like framework worn by a person and a power supply that supplies at least part of the activation-energy for limb movement. Typically, a powered exoskeleton is attached at specific localized points of the body through mechanical means. These local mechanical pressure contact points on the body are deleterious. The use of differential pressure to support the body allows for the coupling of the exoskeleton to the body to be distributed over a large body surface.

The concept of supported differential pressure can be utilized to un-weight other areas of the body. For example, by creating a pressure differential between the narrower waist or lower pelvis of a seated person using a supported differential upper body pressure suit, the person's upper body weight can be unweighted. This could be used to reduce pressure on the lower back and spine for people with lower back pain, degenerative or ruptured disks, etc.

Figure 34:
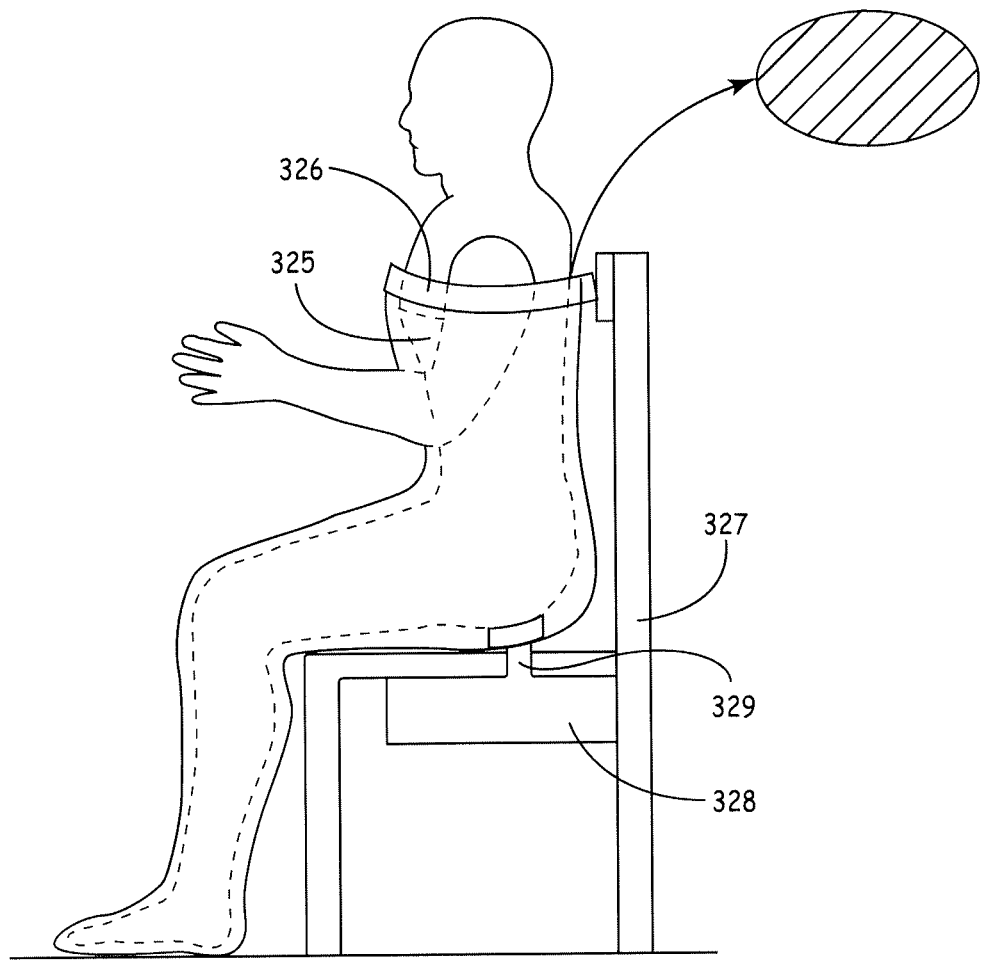
FIG. 34 is a perspective view of a body suit for the upper body to maintain its vertical posture.
Figure 35:
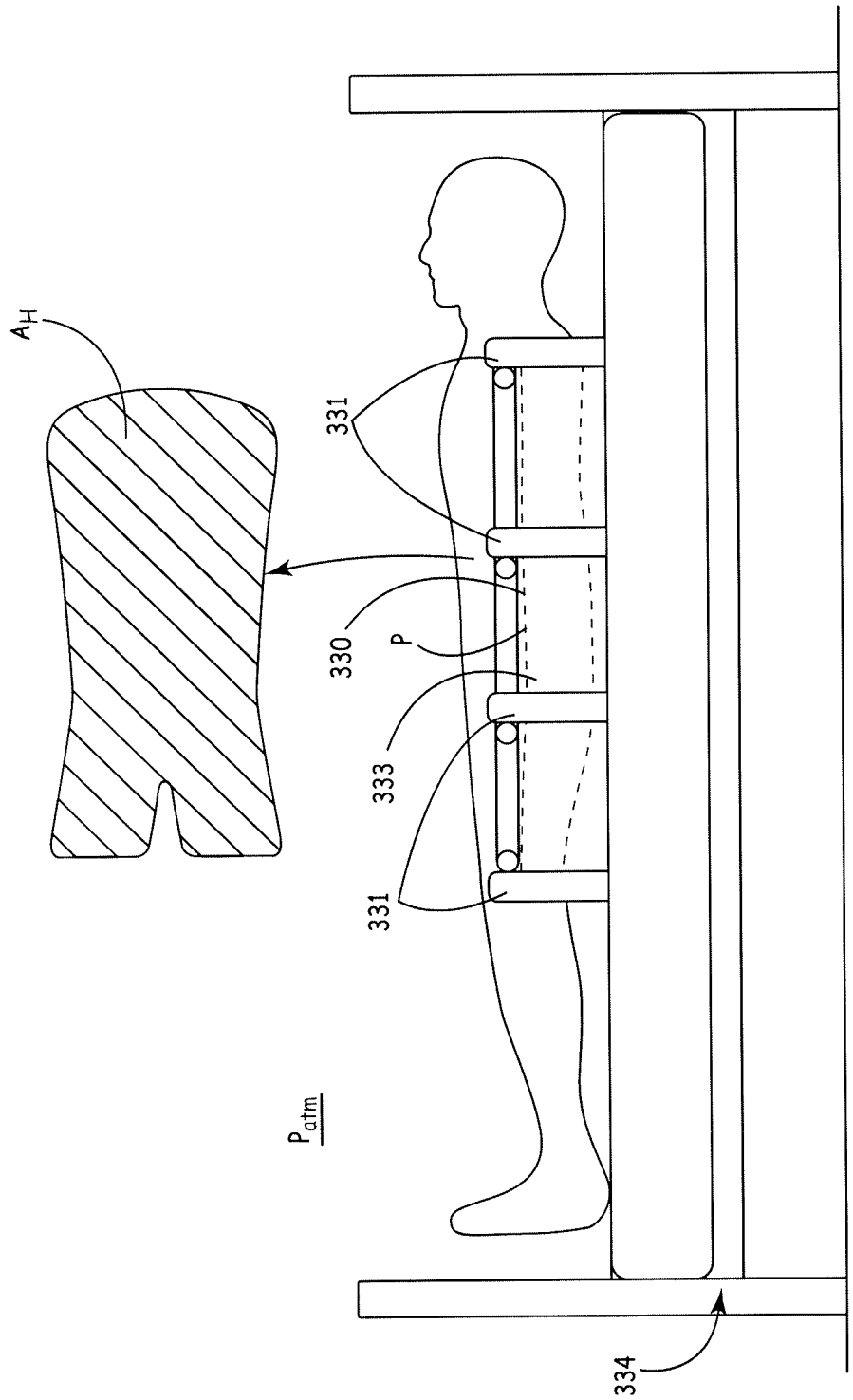
FIG. 35 is a perspective view of a body suit for the upper body to maintain its horizontal posture.
Figure 36:
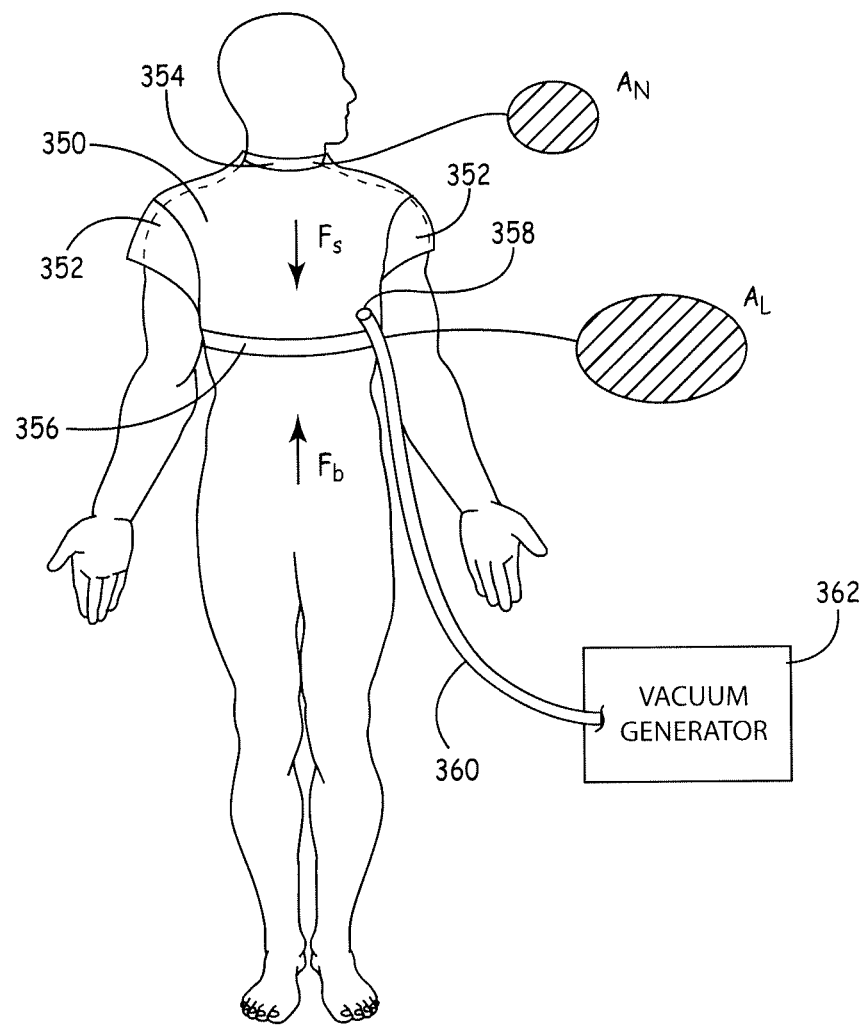
FIG. 36 is a perspective view of body suit vest for applying a negative (vacuum) pressure to the upper body.
Figure 37:
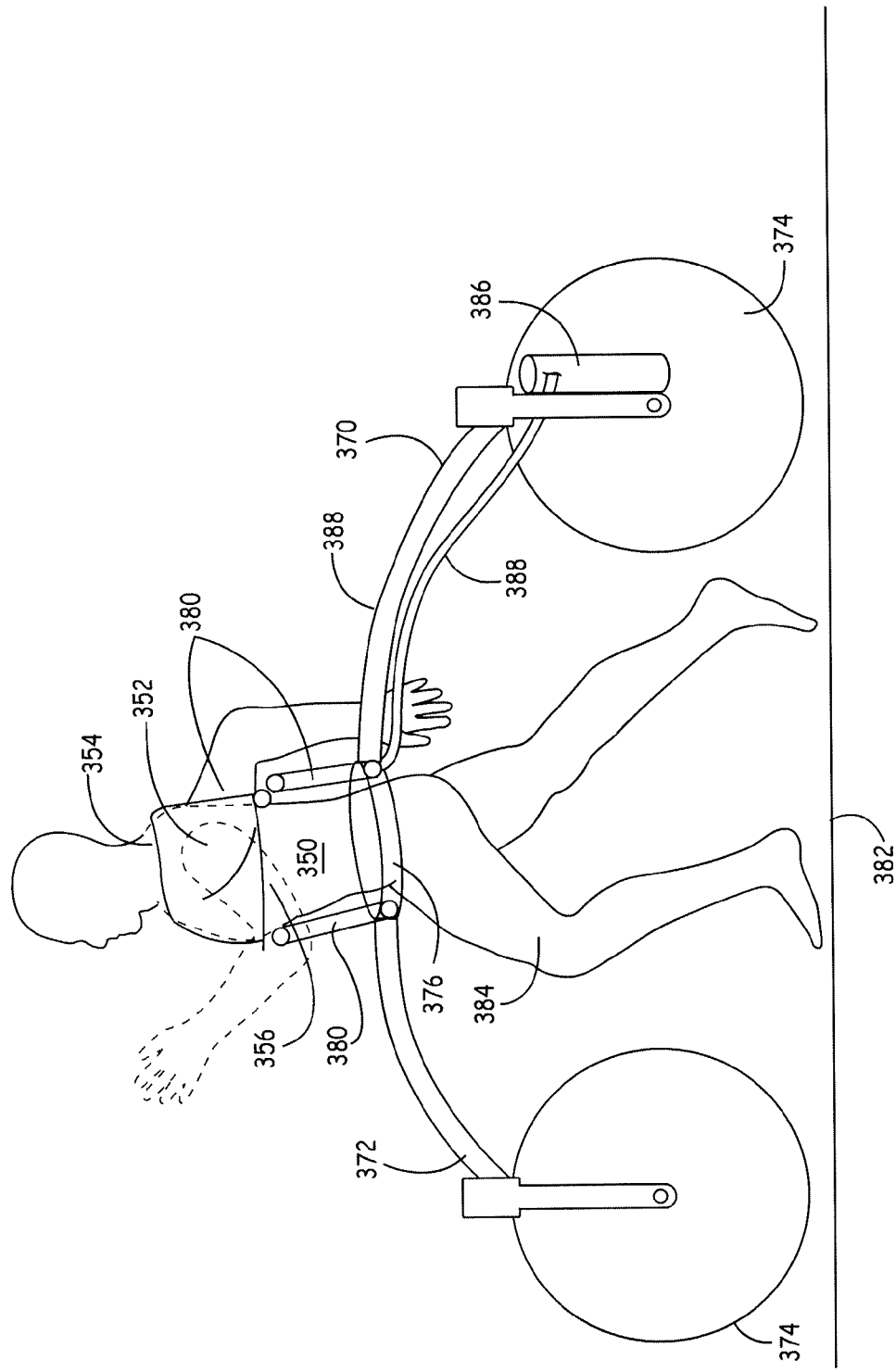
FIG. 37 is perspective view of the body suit vest of FIG. 36 with an external wheeled support frame.
Figures 38, 39:
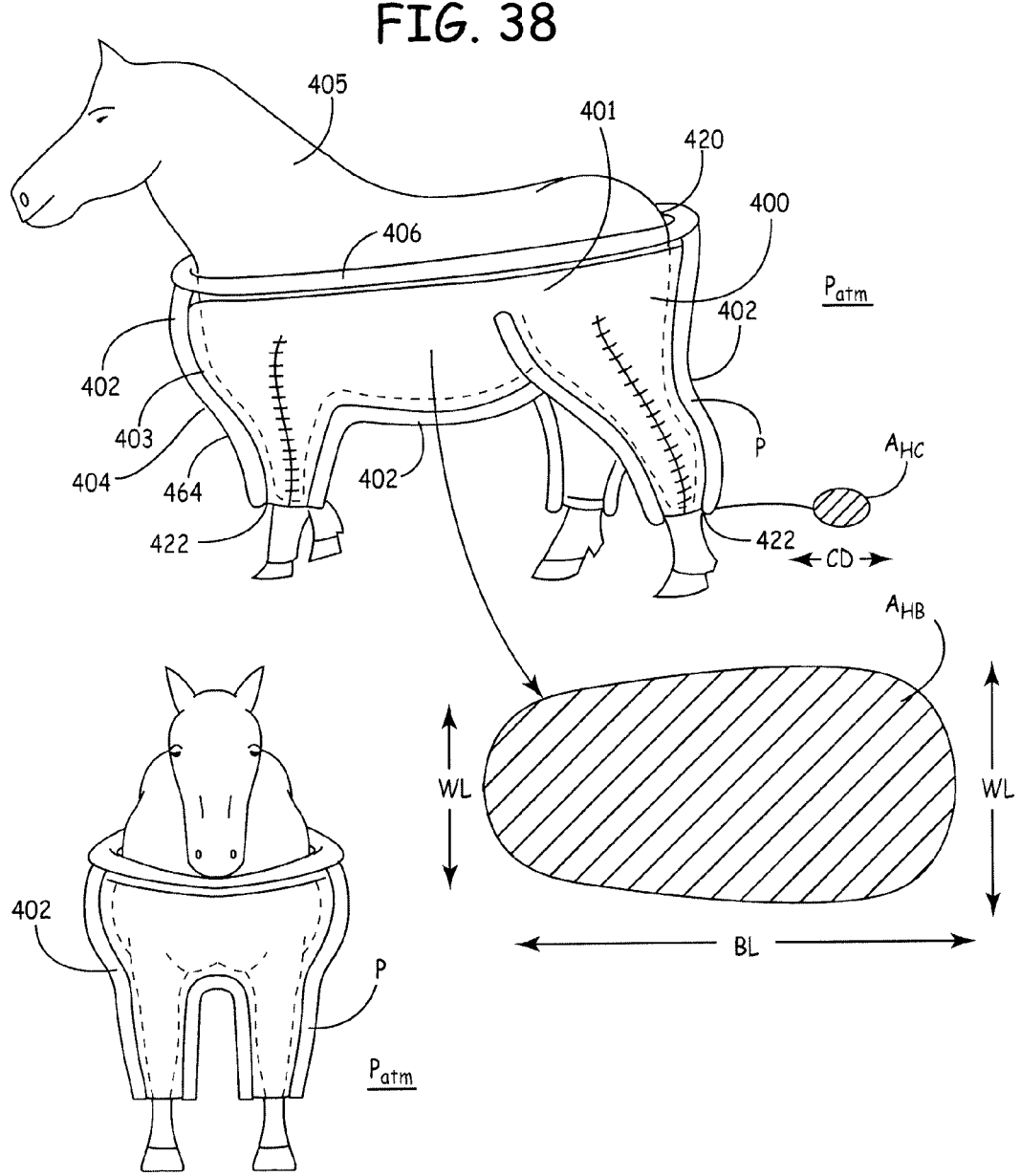
FIG. 38 is a perspective view of a body suit for a horse.
FIG. 39 is a front view of the body suit of FIG. 38.
Figure 40:
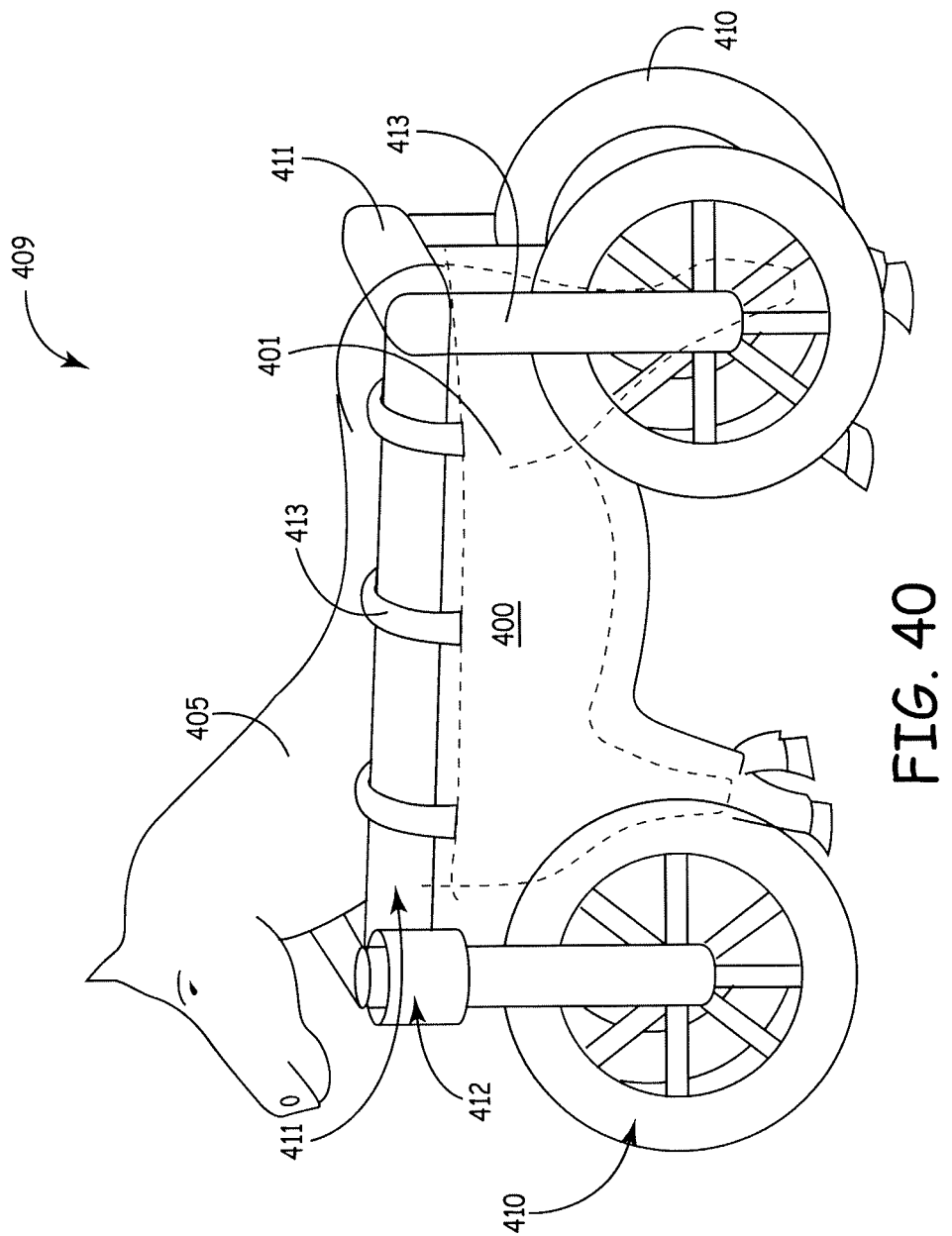
FIG. 40 is a perspective view of the horse body suit of FIGS. 38-39 with an external wheeled cart support frame.

An example of this suit is shown in FIG. 34. The differential pressurized suit 325 shown in FIG. 34 comprises a full-length suit which extend to the chest area just below the arms. This embodiment of the suit completely covers the feet, legs, and lower body. Alternatively, the suit may extend to the ankles, knees, or upper thigh. The suit is sealed at the chest. The seal may constitute any of the sealing methods previously discussed, including a neoprene band, an inflatable tube, or an inflatable bladder. The suit is connected to a rigid band 326. The band serves to attach the suit 14 to the supporting structure 327 which in this embodiment is a chair. The connection is such that the person may easily engage or disengage from the chair. The band 326 conforms to the generally elliptical shape of the chest cross-section. The band and connection to the supporting structure are sufficient to support the downward force of the pressurized suit. Air-tight zippers (not shown) assist entry into the full length pressure suit. The suit can connect and disconnect to connection valve 329 on the chair when the person sits down or gets up from the chair. The connection valve 329 is connected to a pressure control system 328 that can pressurize and depressurize the suit, as needed.

A challenge posed by the pressurized suit of the present invention is proper management of the balance between the downwards force of the suit and the upwards force applied by the previously described constant force adjustment mechanism, support structure, or other offloading means. In particular, the forces must be balanced when the suit is pressurized or depressurized. If the force developed by the downwards force of the suit and the counter force applied by the constant-force adjustment mechanism are not applied simultaneously, the result will be imbalance of the downwards force of the suit and the upwards force of the offloading means. Thus, if the air pressure is applied first, the unopposed downward force will drive the suit downwards. Conversely, if the upward counter tension force is applied first, then the suit will be pulled upwards. If however, the two forces are applied so as to continuously counter-balance each other, then the suit will remain in its correct position on the person's body.

A method for smoothly applying the pressure and the offloading counter force to the person wearing the pressurized suit will be described. The application to pressure pants is used for exemplary purposes only, for a similar system may be applied to the other embodiments of the invention, including the suit using negative differential pressure. The preferred method of an adjustable, but approximately constant-force spring will be described. Following that, a mechanism to create a set point for a control algorithm will be described.

As described above, it is important over small vertical displacements in the range of a typical runner (nominally 3 inches) that the counter force is maintained approximately constantly. A variation of no more than five pounds of force over three inches is preferred. This is readily accomplished with stretch (bungee) cord material of approximately four feet in length, with a spring constant of 10 pounds per foot. Note that two cords are preferably used: one on the left side and the other on the right side of the person. Thus a 40 pound maximum force on each cord will yield an 80 pound offloading maximum. To achieve 40 pounds on each side, the stretch cord will be stretched to twice its length, or four feet of displacement Note that the 3 inch (0.25 feet) vertical displacement of the person during running will cause 2.5 pounds of force loss on each cord at the peak height, for a total of 5 pounds, which meets the preferred minimum variation.

Figure 41:
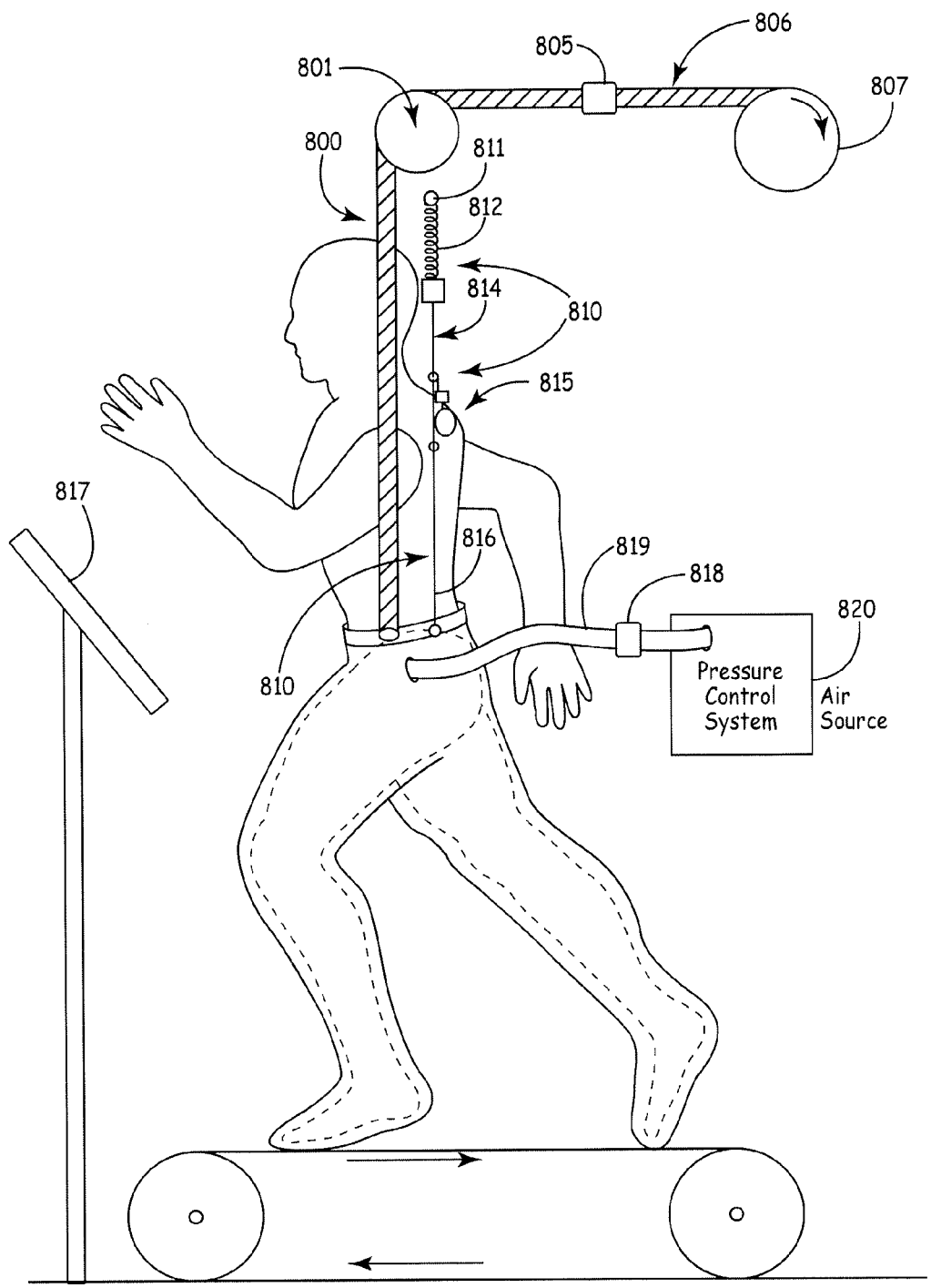
FIG. 41 is a perspective view of an elastic suspension system of the present invention.

In FIG. 41, a pressurized pants implementation is shown depicting the stretch cord connected to the runner's left side. The right side cord is omitted for the sake of clarity. The cord 700 clips onto the pants on one end, and it goes up over a pulley 701 mounted above the person over the treadmill apparatus. At the end of stretch cord 700 is an electronic load cell 705 capable of measuring the desired tension for 0 to 50 pounds, and on the other side of the load cell 705 is a non-extensible cable 706 of about four feet in length, but wrapped around a windup pulley 707. The windup pulley 707 is motor driven with a stepper or servo motor under system microprocessor control.

In parallel with the primary stretch cord 700 is a secondary cord 710 whose purpose is essentially for measurement and control. Cord 710 terminates at a fixed location 711 near pulley 701, and its initial section is a short spring 712 with a spring constant of one pound per foot, followed by an inline control load cell 713, a non-extensible cord section 714, and a hand-operated ratcheting pulley 715 mechanism. The lower end of 715 terminates in a non-extensible rope 716 that attaches to the pants.

The input controller keypad and display 717 contains a microprocessor. The microprocessor receives digitally converted inputs from the load cells 705 and 713 and the pants pressure sensor 718. The microprocessor, in addition to standard I/O functionality for the treadmill, also controls the pants pressurizing valve and a counter tensioning windup motor.

At startup, the individual when ready begins with a START command to the input control pad 717. After standard checks to ensure that inputs are being received from the load cells 705 and 713 and pressure sensor 717, the system instructs the user to tension ratcheting pulley 715 until the 1 pound set point (plus/minus a suitable tolerance) is attained. When attained, a READY status is reported on the display, and the user stops manually tensioning. The primary tension cable 700 is tensioned via actuating the windup pulley 707 until a slight decrease in the control load cell is detected, and then it is paused at this setting. The user then enters on the keypad 717 a target body weight to be offloaded by the system. At this point, the air flow is initiated to generate pressure within the suit and the measurement from load cell 713 is monitored in the control software. As soon as load cell 713 registers a force increase, incremental tension is applied by turning windup pulley 707 again to maintain the set point on the control load cell 713 at one pound. Subsequently an increment of air flow may be applied through air inlet hose 719, followed by incremental counter tension by actuating windup pulley 707 so as to maintain the one-pound set point on the control load cell. In the simplest embodiment, this back and forth iteration may proceed until the desired target weight is achieved on load cell 705, or the maximum system allowed pressure is reached as reported by pressure sensor 718.

More sophisticated control algorithms may also be used for purposes of this elastic suspension system of the present invention, such as a proportional-integral-derivative (PID). The key aspect is that the control parameter as reported by load cell 713 is increased by the air pressure system, whereas it is decreased by the counter tension mechanism, and the control algorithm operates on both systems to maintain the desired set point of the control parameter. When the user begins running, the system may not need to monitor and perform further adjustments. However, by monitoring the cyclic peak values reported by load cell 713, on-going adjustments may be made to maintain the desired set point.

Another method for pressurizing the pants and applying the counter force incrementally may be performed as follows, again referring to FIG. 41. This method does not rely upon secondary load cell 713, or an associated secondary cable and tensioning device. Rather, it relies upon making incremental and alternating steps of pressure and counter tension. The user begins by entering on keypad 717 a target weight to be offloaded by the system. At this point, the air flow is initiated to generate pressure within the pants, and the measurement from load cell 705 is monitored in the control software. The pressurized air is allowed to flow into the pants until load cell 705 registers a small suitable increment, nominally one pound. Then pressurized air flow is stopped, and the counter tensioning is applied by turning windup pulley 707 until an additional pound is registered on load cell 705 (now two pounds total). Note that while the initial force created by the air pressure will have driven the pants down the body by a small increment, the identical force magnitude in the opposite direction created by the counter tensioning device will return the pants to their starting position. Next, pressurized air flow is initiated again, and the load cell 705 is monitored until another pound increment is registered on load cell 705 (now 3 pounds), the air is shut off and again counter tensioning is applied to match that increment with another one pound (now 4 pounds total on load cell 705). This iterative process may be performed rapidly and repeated until the target weight offloading is achieved as registered on load cell 705.

While these embodiments of the elastic suspension system have been depicted with respect to a stationary treadmill located indoors where the control unit can be mounted above the person exercising on the treadmill, it is important to appreciate that portable systems employing the electromechanical principles of this invention can be used as well. For example, a similar system could be mounted to a bicycle frame to manage the countervailing pressure and support forces applied to the pressurized suit worn by the bicyclist. It is also important to appreciate that this elastic suspension system is not essential to use of the pressurized suit of the present invention.

Figure 42:
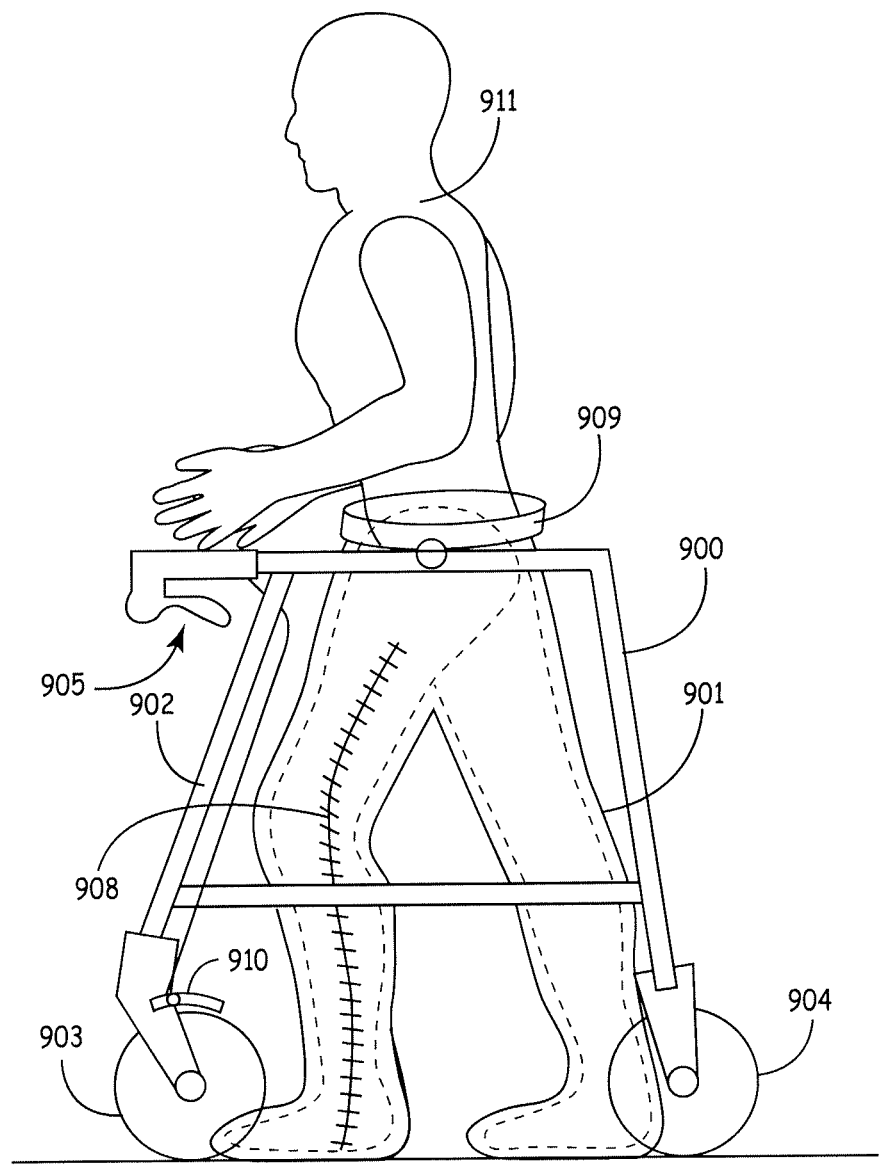
FIG. 42 is a perspective view of a mobile walker support structure used with the pressurized suit invention.

A further use for a mobile pressurized suit is as a support aid that can be used to assist the mobility of elderly or physically-impaired people undergoing rehabilitation, particularly those recuperating from leg or back injuries. The four-wheeled cart-like support structure 900 of FIG. 42 is utilized as a wheeled walker, commonly called a "Rollator." The above-described wheeled walker is also advantageous for those impaired persons with limited or no use of their hands and arms. When the pressure suit of the present invention 901 is worn by such a person, the support aid provides the necessary support for that person instead of him having to resort to his arms and hands leaning on a conventional walker.

The support aid's frame 902 and front wheels 903 and rear wheels 904 are designed and sized so that the mobile unit has the functionality of standard wheeled walkers. The front wheels turn and pivot to allow for easy turning. All four wheels may also turn and pivot. Typically the wheels 903 and 904 are at least seven inches in diameter—preferably eight inches—to ensure better reliability. A three-wheeled walker may also be utilized. Moreover, to enhance the safety, convenience, and durability of a wheeled walking aid and its parts, the wheeled support aid may utilize tubular seats, back seats, and baskets with spacers and cushions.

The wheeled support aid can be incorporated with hand-operated brake levers 905 and brakes 910. The brakes on the wheeled support aid may constitute locking brakes to allow the person to stand while supported in a stationary position. Other means of braking may be provided for those with limited use of their arms and hands. The wheeled support aid can be designed to enable greater range for rotating the body from side to side to enable the person in the wheeled support aid to turn from side to side amd stand facing one side or the other, or even the back. It may also have a seat that will allow for resting. The wheeled support aid will have adjustable height. The wheeled support aid may also be designed with a folding mechanism for compact storage.

The wheeled support aid can feature hand supports for assisting the entry and exit from the support aid. The wheeled support aid can be constructed from light-weight materials such as aluminum or composites. The pressure-assisted wheeled support aid may preferably use tubular seats, back seats and baskets with spacers and cushions. The wheeled support aid can be equipped with a source of pressurized air to control pressurization of the suit, and means for balancing the downwards force of the suit automatically as the pressure is adjusted.

The impaired person 911 wears a pressurized suit 907 that attaches to the frame of the walker at attachment points 907. The various attachment methods previously described may be utilized. The previously described constant-force adjustment mechanisms may also be incorporated. For walking applications, there is minimal up and down vertical motion of the walker compared with a running motion, so less overall adjustment and force balancing is needed for this embodiment. Various embodiments of the pressurized suit 901 described earlier can be utilized with this wheeled support aid. The suit can be customized for easy entry and exit by physically impaired persons. In particular the pressure suit can have extra long zippers 908 and an easy entry supporting ring which makes the suit easy to put on for a physically impaired person.

In addition to injury rehabilitation and cardio training, the pressurized suit of the present invention can also be used with beneficial results by a person looking to lose weight. In order to burn fat through physical exercise the medical community advises that the person's heart rate needs to be maintained within a specified range, usually lower than the heart rage for cardio training. Many people significantly overshoot this heart rate range for fat burning, resulting in a failure to lose desired amounts of weight. This disappointment often causes people to quit their exercises because of their difficult or unpleasant nature, and rely instead upon extreme diets.

The pressurized suit of the present invention, when properly used, enables the person to reach an elevated level of physical exercise with a significantly reduced heart rate. This should make it easier for that person to maintain her heart rate within the prescribed range for fat burning, and enhance the likelihood of achieving her weight reduction goal.

Figure 41B:
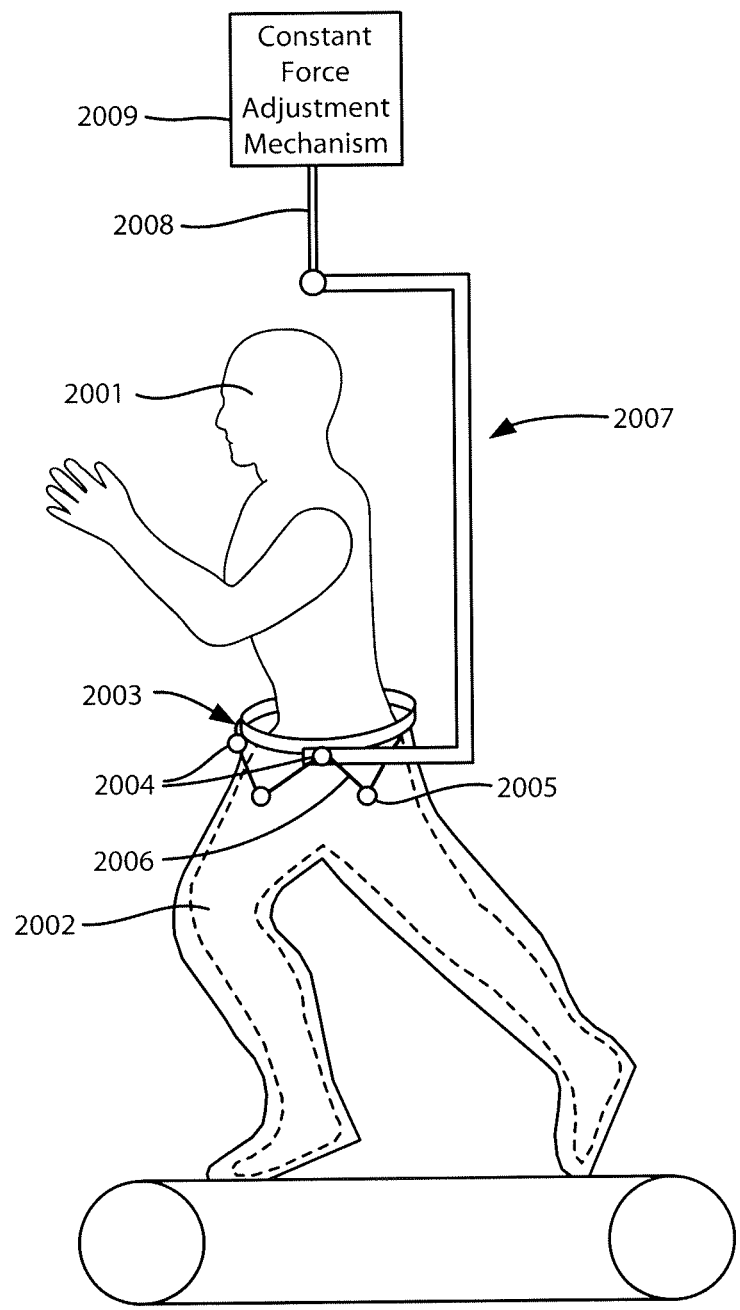
FIG. 41b is a perspective view of the body weight support device of the present invention.

FIG. 41*b* shows a body weight support device for a person (2001) walking or running on a treadmill. The person (2001) wears a lower body suit (2002). Preferably the suit may be a differential pressure suit as previously described in this application. Alternatively, the suit may be a non-pressurized suit, or a harness. A rigid band (2003) encircles the lower body at approximately the waist. Pulleys (2004) are connected to the bend at intervals around the band. Another set of pulleys (2005) is connected to a lower body suit at intervals. A cord (2006) runs through the pulleys on the band and the pulleys on the suit. The cord alternates passing through a pulley on the band and a pulley on the suit. The ends of the cord are connected together so that it forms a continuous loop around the waist through all the pulleys. The cord and pulleys thus connect and transfer mechanical load from the suit to the rigid band. A suspension mechanism (2007), attaches to the band (2003) at its lower end (2002) and attaches to a cable (2008) at its upper end. The cable (2007) is connected to a constant force adjustment mechanism (2009) as previously described in this Application.

Figure 42B:
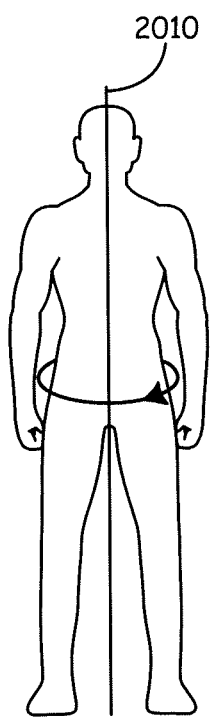
FIG. 42b is a schematic showing the superior-inferior axis of rotation for a human body.
Figure 43:
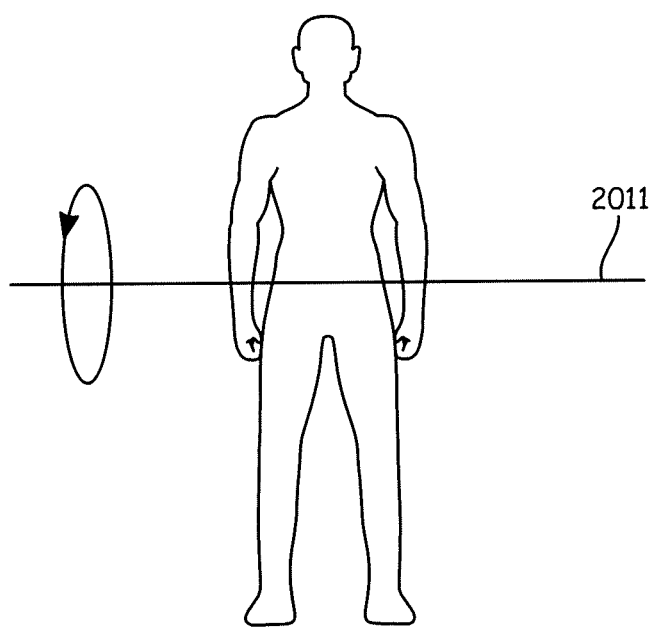
FIG. 43 is a schematic showing the medio-lateral axis of rotation for a human body.
Figure 44:
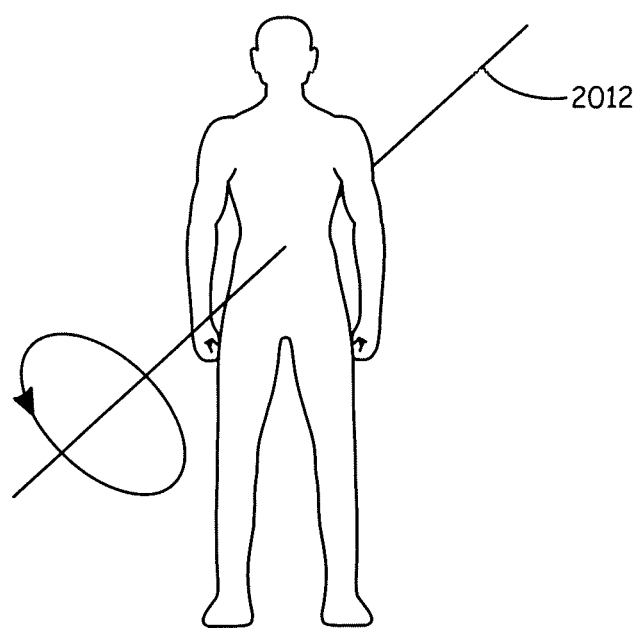
FIG. 44 is a schematic showing the anteroposterior axis of rotation for a human body.
Figure 45:
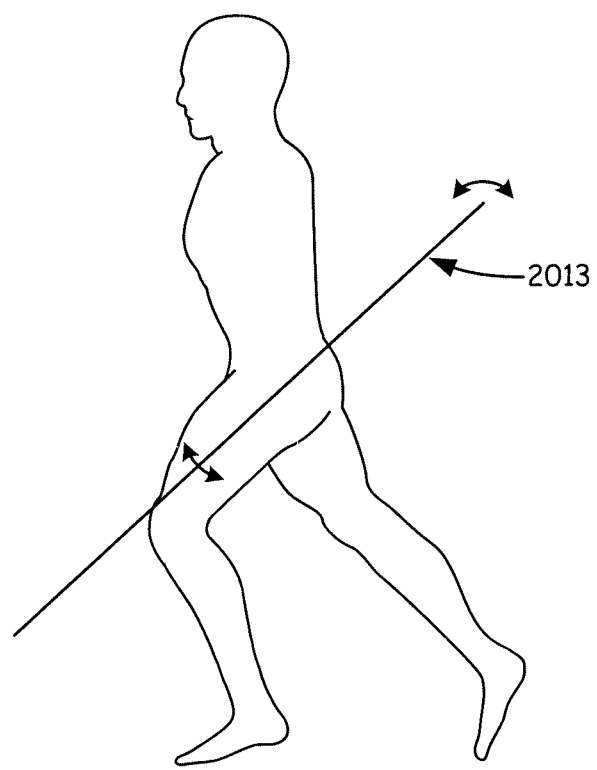
FIG. 45 is a schematic showing the medio-lateral axis of rotation through the hip joints for a human body.

The invention provides body weight support in a way that does not restrict one's natural body movements that occur while walking or running. Specifically the invention is an improved system for a body weight support device for connecting a person's body to the weight off-loading components of the device (referred here to a constant force adjustment mechanism) so as not to restrict natural body movements. During walking or running gait the body moves and rotates about various axes of the body. First, the superior-inferior axis (i.e. vertical axis) (2010) is shown in FIG. 42*b*. A person's hips and lower body rotates back and forth about this axis when walking or running as the leg and hips are moved forward at the start of a gait cycle and pulled backwards at the end of the cycle. Second, the medio-lateral (i.e. side to side) axis (2011) is shown in FIG. 43. A person's body rotates about this axis as the person leans forward from a stationary standing position to run or walk, the degree of lean or rotation depending on the persons running style and speed. Third, the anteroposterior axis (i.e. front to back) axis (2012) is shown in FIG. 44. During running or walking the hips and lower body move up and down about this axis. Fourth, the legs rotate back and forth about a medio-lateral axis through the hip joints as shown in FIG. 45. A body weight support device must apply a substantial force to the body to support up to a high percentage of total body weight without having this force restrict natural body movements and rotations. The present invention provides a means for supporting body weight without restricting body movement and rotation about these four axes of rotation.

Figure 46:
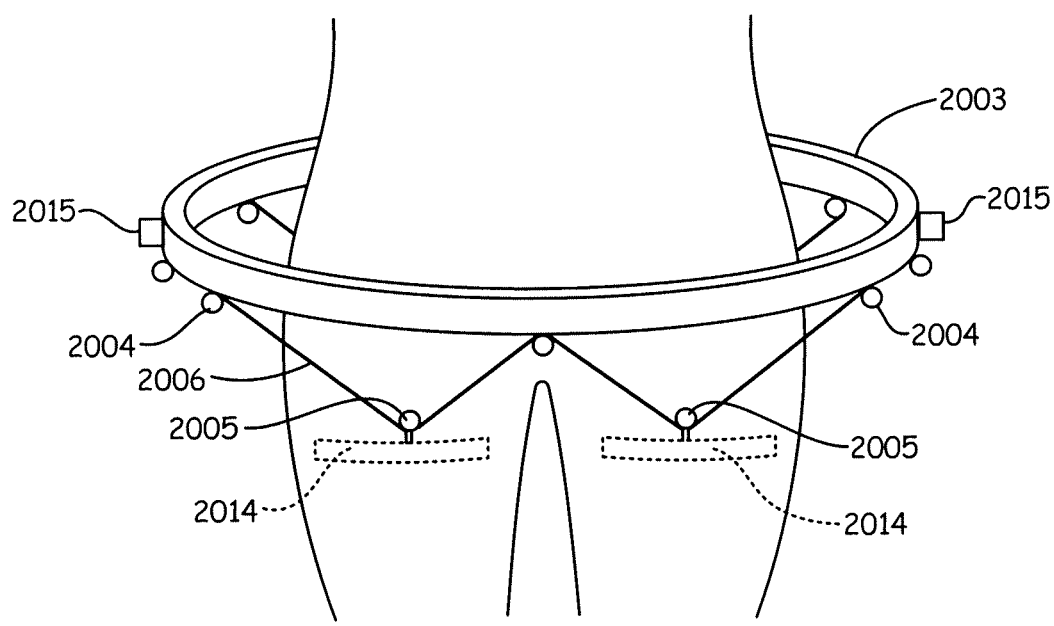
FIG. 46 is a perspective view of the pulley attachment between the body suit and the band of the body weight support device.

The attachment between the body suit and the band is shown in detail in FIG. 46. A rigid band (2003) positioned about the waist of a person at approximately at the waist level. The band is substantially rigid in the vertical direction to support the body weight that is offloaded. In a preferred embodiment the band is a curved rigid aluminum strip 1 inch wide and ⅛ inch thick. The band may also be constructed to flexible in the horizontal plane so as to be compliant and flexible around the waist, while rigid in the vertical direction to support the weight offloaded. Such a band can be constructed of multiple thin strips to provide flexibility. In one embodiment the band is constructed from 3 stainless steel strips 1 inch wide and ¹⁄₃₂ Inch thick that are bound together. Pulleys (2004) are attached to the band at spaced intervals. Another group of pulleys (2005) are attached to a suit at spaced intervals. In a preferred embodiment a rigid supporting bar (2014) is sewn into a sleeve in the suit and the pulley is attached to it to provide for an even distribution of stress across the fabric of the suit. A cord (2006) runs through the pulleys alternating between the pulleys on the body suit and the pulleys on the band. The ends of the cord are joined so that it forms a continuous loop around the body and through the pulleys. In a preferred embodiment the vertical distance between band and the pulleys attached to the suit is approximately 4 inches, however it may be more or less than this. The attachment pegs on the sides (2015) provide a means for connecting the band to a supporting mechanism.

Figure 47:
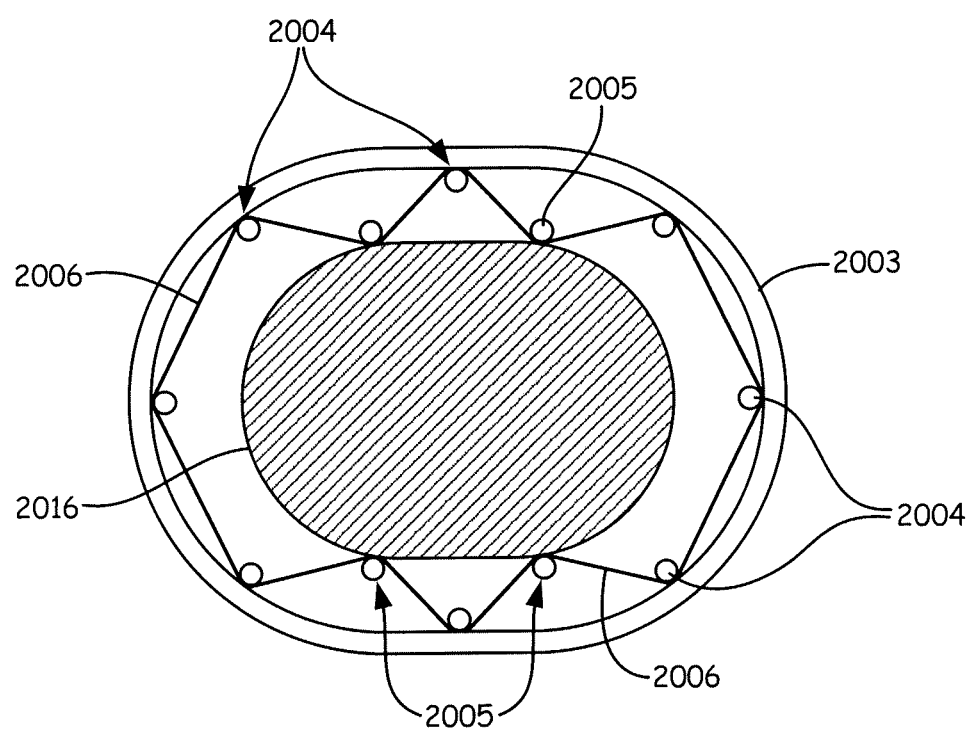
FIG. 47 is a top down cross-sectional view of the band and pulley attachment system of FIG. 46.

FIG. 47 shows a top down cross sectional view of the band (2003) and pulley attachment system. The cross-section of the body at the waist (2016) has a roughly oval shape. In a preferred embodiment the band is approximately oval in shape. In a preferred embodiment the band is a continuous loop. It may also be hinged and fixed with a clasp to allow for easier doffing and donning. Pulleys (2004) are attached to the band at spaced intervals. In a preferred embodiment eight pulleys are attached to the band. In other embodiments 4, 6, 8, 10 or 12 pulleys are attached. Another group of pulleys (2005) are attached to a suit at spaced intervals. Each pulley attached to the lower body suit is positioned at approximately a midpoint between the pulleys on either side of it on the band. Each pulley attached to the body suit (2005) is positioned to be at the middle between the pulleys on the band on either side of it (2004). The cord (2006) may also pass through several band pulleys in a row to maintain clearances of the cord and pulleys and the body during body movements. The cord may be comprised of either a low stretch material such as nylon or elastic material such as stretch cord.

Figure 48:
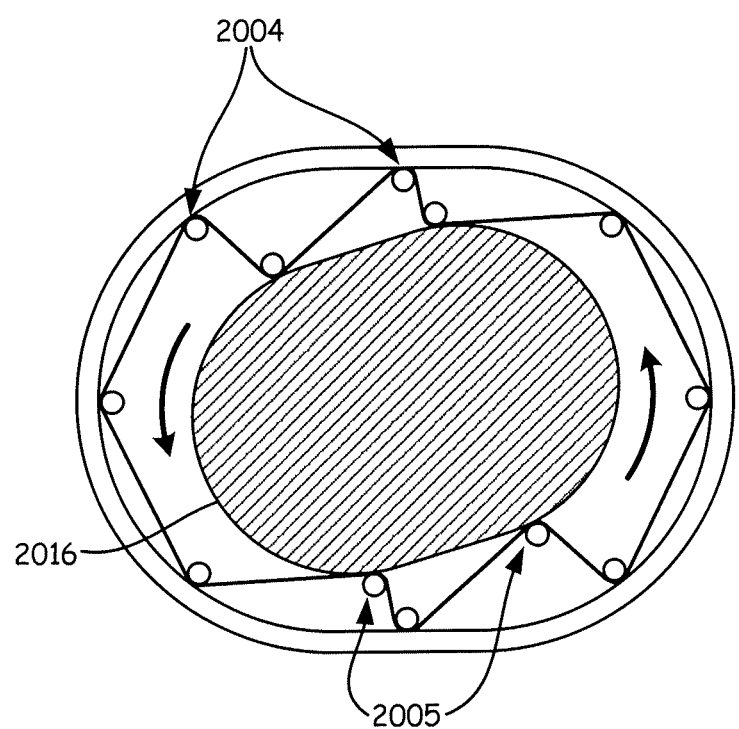
FIG. 48 is a top down cross-sectional view of the band and pulley attachment system of FIG. 46 with the person's lower body and hips rotated.

FIG. 48 shows a top view of the band and pulley attachment system when the lower body and hips have rotated counter-clockwise and the band has remained stationary. When the hips and lower body rotate as part of a normal running or walking the pulleys on the body suit move along the connecting cord so that their positions change relative to the pulleys on the band. As shown in FIG. 48 as the body has rotated counter-clockwise each pulley on the body suit (2005) has moved along the cord to a new position so that it is closer to the pulley (2004) on the band in the direction of rotation and further from the pulley (2004) on the band that it is away from the direction of rotation.

Figure 49:
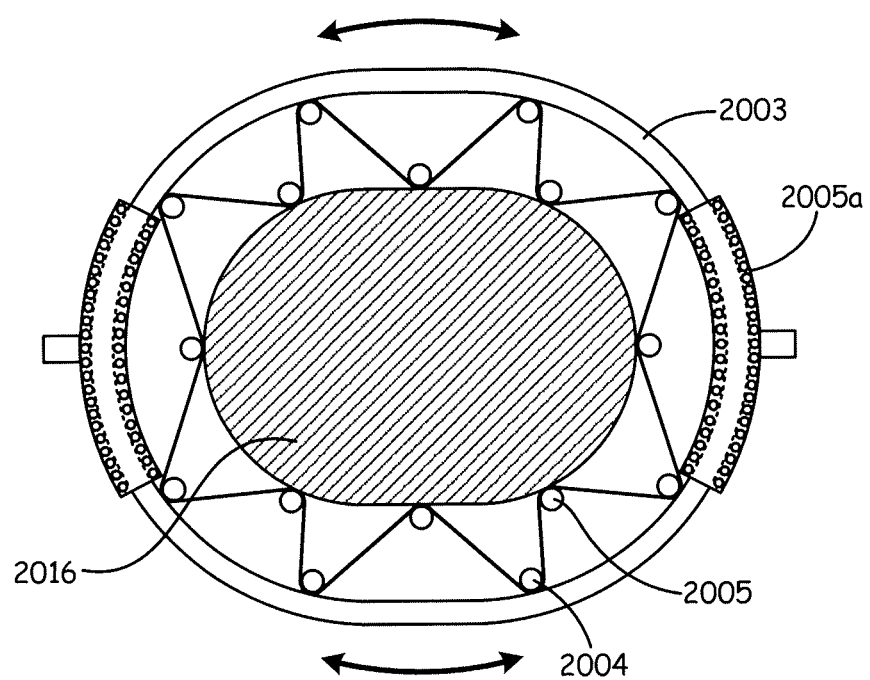
FIG. 49 is a top down cross-sectional view of the band and pulley attachment system of FIG. 46 having curved linear bearings.

FIG. 49 shows a top view of an embodiment of band and pulley attachment system in which curved linear bearings (2005a) are incorporated at the attachment points at the end. The band in this embodiment is circular in shape. The band is constructed with grooves that match with the curved linear bearing (2005a). This design allows for free rotation of the band about the superior-inferior axis (i.e. vertical axis) of the person. Other mechanisms that provide for rotary motion such as curved linear rails might also be utilized. Eight pulley's (2004) are attached to the band at spaced intervals. The pulleys are attached at the bottom of the band so as to not interfere with bearings. The housing for the curved linear bearings goes over the top of the band. Another group of eight of pulleys (2004) are attached to a suit at spaced intervals. Other numbers of pulleys may also be used such as 4 or 6 or 10 or 12.

Figure 50:
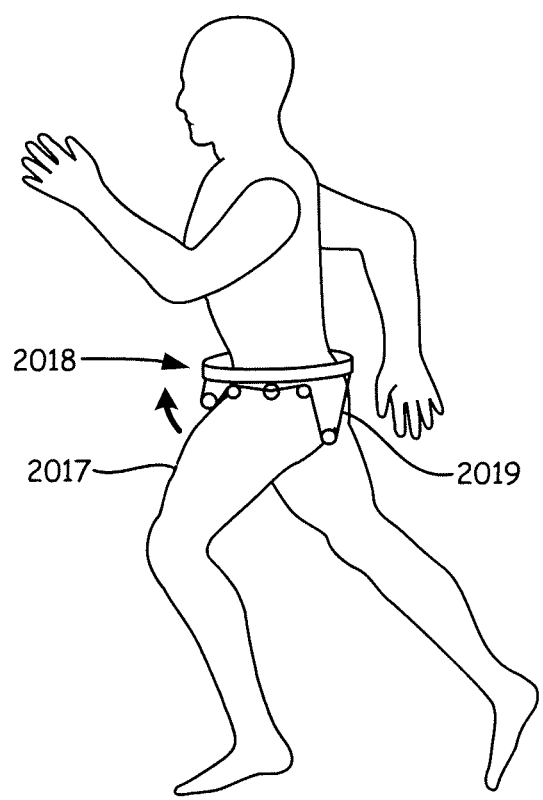
FIGS. 50 and 51 are perspective views showing the adjustment of the band and pulley attachment system to the motion of the person's leg about the hip during the running stride.
Figure 51:
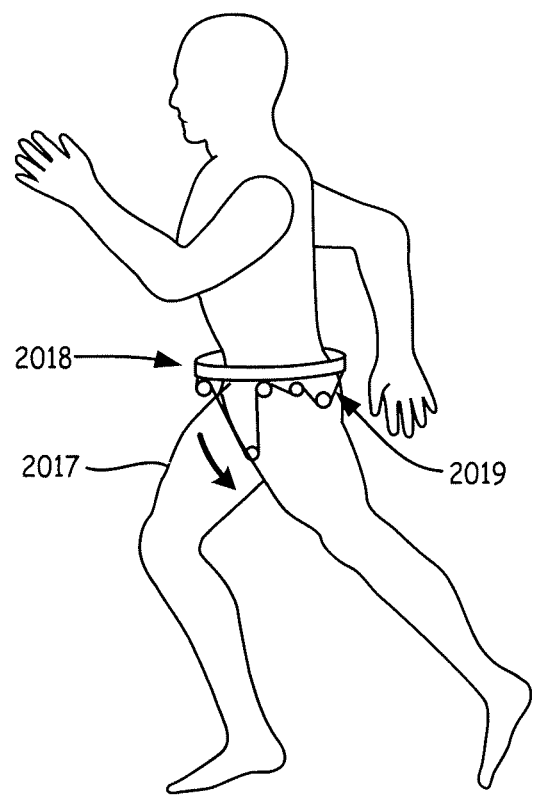

FIGS. 50 and 51 show the adjustments of the system to the motion of the leg about the hip during a running stride. During a walking running gait cycle the legs swing back and forth about a medio lateral axis through the hip joints as shown previously in FIG. 45. FIG. 50 shows the start of a gait cycle as the left leg is placed forward. The lengths of the cords connecting the band pulleys to the suit pulleys are denoted as left-front-cord-lengths (2018) and left-rear-cord lengths (2019). As the left leg is placed forward at the beginning of the stride the left-front-cord-lengths shorten and the left-back-cord-lengths lengthen. FIG. 51 shows the change in cord lengths of the cords connecting to the left leg as the leg has moved backward. As the left leg is moves backwards at the end of the stride the left-front-cord-lengths lengthen and the left-back-cord-lengths shorten. The tension in the cord remains the same throughout the gait cycle so that the system provides body weight support without constraining the back and forth movement of the legs about the hips.

Figure 52:
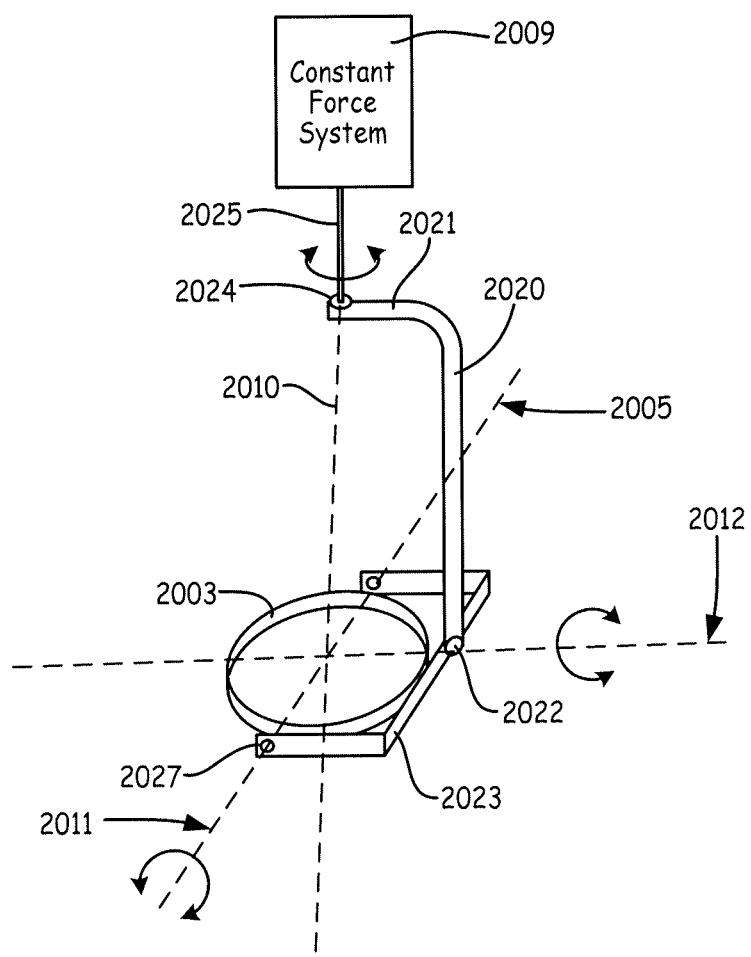
FIG. 52 is a perspective view showing the components of one embodiment of the suspension apparatus of the body weight support device.

In addition to band and pulley system the present invention can include a second suspension apparatus for providing freedom of movement of the body about the various axes of rotation with body weight support. FIG. 52 shows the components of one embodiment of suspension apparatus (2005) which connects the rigid waist band to the counter force system (2007). A rigid bar (2020) generally in the shape of an inverted L is connected to a cable (2025) that is connected to a counter-force adjustment system (2009). The connection between the cable and bar is made with bearing (2024) to allow for rotation. A C-shaped horizontal support bar (2023) is attached to the vertical bar (2020) at a pivot bearing (2022). The rigid waist band (2003) is attached to the c-shaped horizontal support bar at pivot points (2027) on each side. The attachment mechanism can be either a manually opened and closed latch or automatic coupling latch such that the band is easily attached or detached from the c-shaped horizontal support bar. The latch can be such that the pivot features of the attachment are maintained.

In other embodiments, as will be described subsequently the rigid band is attached directly to a constant-force adjustment system. In other embodiments the cord (2006) is made of an elastic material such as a stretch cord. The cord itself becomes the constant force adjustment system. The length and tension of the elastic cord may be adjusted to provide various amounts of force. In a preferred embodiment the tension in the elastic cord is adjusted by raising or lowering the height of the band in relation to the person's body. As the height of the band is increased the tension in the elastic cord increases and the amount of body weight that is supported increases. The elastic band provides a relatively constant force within the range of vertical up and down movement of a person walking or running.

The above described suspension apparatus the present invention provides for unrestricted movement of a person about the various axes rotation of the body. In use the upper end of the bar (2021) and the cable (2017) are aligned with the superior-inferior (i.e. vertical) axis (2010) of the person. The cable and bar (2016) are free to rotate about this axis as the person's body rotates. This allows for unrestricted body and hip rotation about the superior-inferior (i.e. vertical) axis (2010) of the person. The pivot attachment point between the vertical L-shaped support bar (2020) and the horizontal c-shaped support bar (2023) allows the c-shaped support bar (2021) to pivot about the anteroposterior (front to beck) axis (2012) of the person. This allows for unrestricted back and forth rotation about the anteroposterior (front to back) axis (2012) of the person. The pivot bearing attachment (2027) between the horizontal c-shaped support bar (2023) and the band (2003) allows the band (2003) to pivot about the medio-lateral (i.e. side-to-side) axis (2011) of the person in the device which allows for unrestricted rotation of the person. In summary the suspension mechanism (2005) provides a means for supporting body weight without restricting body movement and rotation about the superior-inferior, anteroposterior and medio-lateral axes of rotation. Thus both the band pulley system and the suspension mechanism provide for unrestricted movement of the body during walking and running. They both provide a means for enabling unrestricted body movement in a body weight support device.

Figure 53:
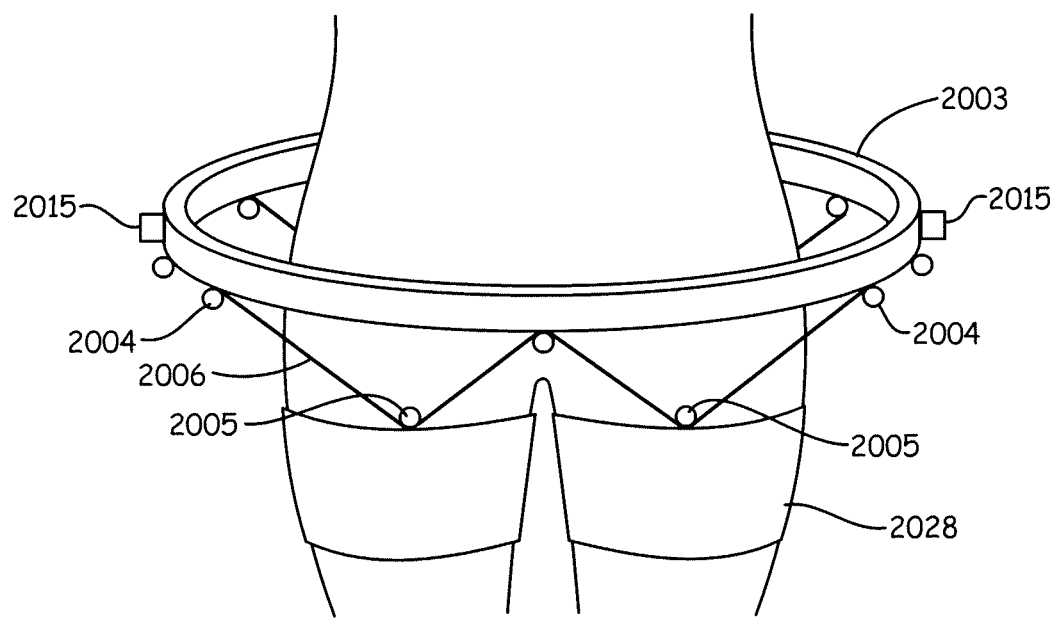
FIG. 53 is a perspective view of an alternative embodiment of the body weight support device featuring a leg harness.

An alternative to pressure suit unweighting is shown in FIG. 53. This embodiment shows the rigid band body weight support device in which the device is connected harness (2028) that is attached to the person's legs. A suitable harness is constructed from nylon webbing. Velcro closures and nylon straps and buckles allow the harness to be adjusted to fit different body sizes. The harness may have padding and rigid or semi rigid areas to provide additional comfort. The rigid band and pulley and system are the same as previously described and shown in FIG. 46. In this embodiment the pulleys (2005) are attached to a harness at spaced intervals. Pulleys (2004) are attached to the rigid band (2003) at spaced intervals. A cord (2006) runs through the pulleys. The device provides for unrestricted body movements along all body axes of rotation as previously described improving on existing harness systems.

In another embodiment the rigid band and pulley system is used with a mobile device such as a walker as a support aid that can be used to assist the mobility of elderly or physically-impaired people undergoing rehabilitation, particularly those recuperating from leg or back injuries. A mobile walker to provide body weight support using differential pressure suit is previously described in this application. Another use of the rigid band and pulley system on a mobile device is to provide stability for walking. If a person becomes unstable or loses balance the pulleys and band inherently provide a counter force as the person tilts from vertical. The pulleys and band make it difficult or even impossible to fall. Falls are a major source of injury and death to the elderly and disabled population. The above-described wheeled walker is also advantageous for those impaired persons with limited or no use of their hands and arms because it does not require the use of their hands and arms for support as is necessary with a traditional walker.

The support aid provides the necessary support and stability for that person instead of him having to resort to his arms and hands leaning on a conventional walker. The support aid may also be used to provide body weight support while both walking and running. It is an improved system for rehabilitating a skeletal joint injury or training for injury prevention, athletic performance, or fat reduction, or assisting the mobility of the physically disabled.

Figure 54:
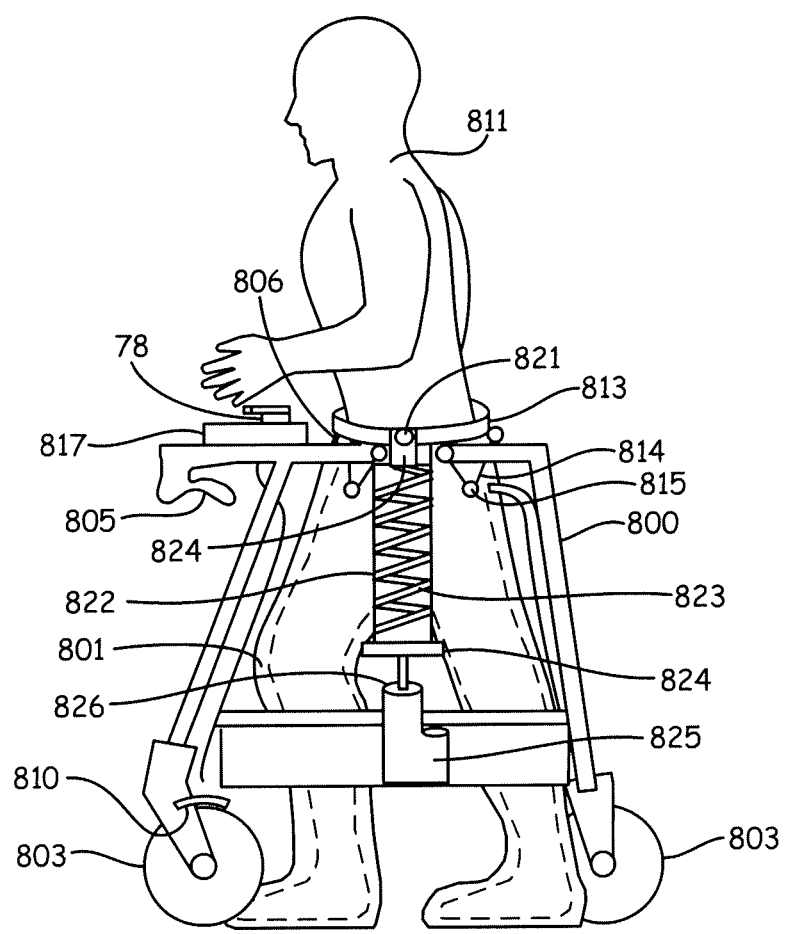
FIG. 54 is a perspective view of the rigid band and pulley system used to provide body weight support to a person on a powered four-wheeled support structure.

FIG. 54 shows an embodiment of the rigid band and pulley system used to provide body weight support on a powered four-wheeled support structure 800 of FIG. 54 is utilized as a wheeled walker, commonly called a "Rollator." A support aid utilizes a pressure suit, a powered air pressure source, and a powered constant force adjustment mechanism. Various embodiments of the pressurized suit 801 described earlier can be utilized with this wheeled support aid. The suit can be customized for easy entry and exit by physically impaired persons. A rigid band (813) encircles the lower body at approximately the waist. Pulleys (806) are connected to the band at intervals around the band. Other similar pulleys (815) are connected to a lower body suit at intervals. A cord (6) runs through the pulleys on the band and the pulleys on the suit. The cord alternates passing through a pulley on the band and a pulley on the suit. The ends of the cord are connected together so that it forms a continuous loop around the waist through all the pulleys. The cord and pulleys thus connect the suit to the rigid band. The band is connected to a constant-force adjusting mechanism (822) on each side of the support device. The band is attached to the constant force adjustment mechanism using an attachment latch. The attachment latch can be either a manually opened and closed latch or automatic coupling latch such that the band is easily attached or detached from the c-shaped horizontal support bar. The latch can be such that the band may rotate or pivot about the attachment point.

A constant-force adjustment mechanism 822 is attached to each side of the wheeled support aid. The constant force adjustment mechanism control system and user interface may be similar to the constant force adjustment mechanism previously described in this application. In the embodiment described herein compression springs 823 are utilized to provide the constant force. Other mechanisms that provide a relatively constant force such as constant force air springs might also be utilized in place of the compression springs.

The preferred method of an adjustable compression spring will be described. It is important over small vertical displacements in the range of a typical walker (nominally 1-3 inches) that the counter force is maintained without great variability. Thus a spring constant of only a few pounds per inch is used such that force when the spring is compressed changes only modestly when the individual rises slightly during walking.

In FIG. 54, a mobile support aid utilizing the band and pulley system and pressurized pants is shown depicting the compression springs connected to the person's left side. At the end of compression spring (823) is an electronic load cell (824) capable of measuring the desired compression from 0 to 100 pounds. Mounted on the bottom side of the compression spring is a gear motor (825) and displacement shaft (826). The motor has a displacement encoder that is fed to the system microcontroller, along with the load cell information. In this embodiment the user selects two parameters from the input box (817) rotary dials (818): desired unweighting level in pounds and a setting that relates to the cross sectional area of the individual. In the preferred embodiment of the input dial, this dial is labeled a 'comfort' setting, and individual users select a value that they determine in practice gives them a balance between the net downward force supplied by the pants air pressure, and the upward force on the pants supplied by the counter-tensioning system. A higher 'comfort' number will yield a higher pressure for a given un-weighting value, and would be necessary for thinner individuals. Conversely, a lower 'comfort' number would yield lower pressure for a given un-weighting value and would be needed for larger individuals. These comfort numbers 1-16 are simply mapped into cross-sectional area values in the control software, such that the following equation is maintained: $Wu = P*A$, where $Wu$ is the desired unweighting value, P is the air pressure, and A is the cross sectional area derived from the comfort dial setting. With $Wu$ and A effectively chosen by the user, the appropriate pressure P to support the un-weighting value is solved for.

Upon startup, the unweighting is not realized all at once, but can only happen as fast as the pants become pressurized, which in the described system requires on the order of 10 to 20 seconds. The counter-tensioning value, supplied by engaging the gear motor to begin compressing the compression springs, is developed at a rate such that the above equation is maintained dynamically, within a 5 pound limit. In the preferred control algorithm during build up to a target unweighting value, the load cells and pants pressure are read every 50 milliseconds, and if the above equation, due to increasing pressure can support a further increment of unweighting, the gear motor is engaged for a short increment. Air flow continues until the desired target air pressure is reached, and every few milliseconds further force is applied to the springs such that when the air pressure target is reached, the counter-tensioning value is simultaneously reached. The same lock step algorithm is engaged if the un-weighting set value is changed, or dropped to zero.

A further enhancing mechanism particularly for disabled individuals desiring to walk in the system is power assisted wheels. A phenomenon when one is greatly unweighted by the disclosed walker system, is that one has less 'leaning' ability to nudge the walker into motion, simply because one effectively weighs less. Normal individuals can easily overcome this by pushing with their arms and legs, but the addition of power-assisted wheels are a useful enhancement for frail or rehabilitating individuals. The mechanism is realized by an electric motor and clutch on each of the front two wheels that supply a significant fraction of the force necessary to overcome friction and roll the walker. The motor need not run full time but is engaged with a hand switch on the walker to conserve battery power. This also serves as an optional braking mechanism, in that if the engagement switch is released, the wheels may brake. The clutch mechanism allows users to exceed or overdrive the force supplied by the motor to the extent that they are capable of exceeding the very minimal startup speed supplied by the wheel motors.

Figure 55:
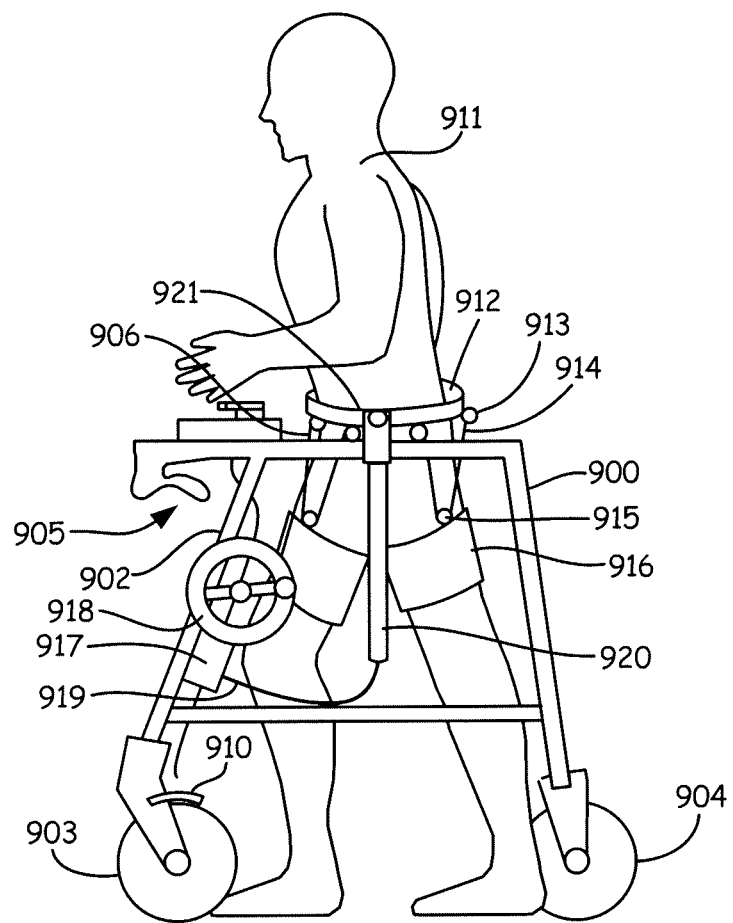
FIG. 55 is a perspective view of the rigid band and pulley system used to provide body weight support to a person on a non-powered, manually-operated four-wheeled support structure.

FIG. 55 shows an embodiment of the rigid band and pulley system used to provide body weight support on a non-powered manually operated four-wheeled support structure (900) is utilized as a wheeled walker, commonly called a "Rollator." A harness (916) is utilized in this embodiment. In other embodiments a pressurized or non-pressurized suit may be utilized. The harness consists of bands (916) on the legs of the person (911) and is constructed as described previously. The rigid band and pulley system (906) attaches to a harness (916) on the legs of the person (916). This particular embodiment of a wheeled support aid does not require a powered source for pressurized air or a powered constant force adjustment mechanism.

Some advantages of a non-powered mobile support aid are to provide stability and body weight support are lighter weight, ease of use and lower cost. In this embodiment an elastic cord (914) that runs through the pulleys attached to the band and harness is utilized as a constant force adjustment system. The tension in the cord is manually adjusted by raising or lowering the rigid bend. Hydraulic cylinders 920 are attached to each side of the wheeled support aid. The rod end of the hydraulic cylinder is attached to the band by an attachment latch. The attachment latch can be either a manually opened and closed latch or automatic coupling latch such that the band is easily attached or detached from the c-shaped horizontal support bar. The latch can be such that the bend may rotate or pivot about the attachment point. The band is raised or lowered by turning a crank (918) that operated a hydraulic pump (917). The pump is connected to the hydraulic cylinder by a hydraulic line (919). Other mechanical means of raising and lowering the band might also be utilized in other embodiments. The tension in the band might also be adjusted by lengthening or shorting the elastic cord which runs through the pulleys. The ends of the elastic cord may be connected to each other by a means which allows for easy adjustment. The walker may also be utilized in a mode without a constant-force adjustment mechanism by utilizing a non-elastic cord.

Both the powered and non-powered mobile support aids that utilize the band and pulley suspension system can utilize a pressurized suit, a non-pressurized suit or a harness. The powered mobile support aid's frame 802 and front wheels 803 and rear wheels 804 are designed and sized so that the mobile unit has the functionality of standard wheeled walkers. Similarly the non-powered mobile support aid's frame 902 and front wheels 903 and rear wheels 904 are designed and sized so that the mobile unit has the functionality of standard wheeled walkers. The front wheels turn and pivot to allow for easy turning. All four wheels may also turn and pivot. Typically the wheels 903 and 904 are at least seven inches in diameter—preferably eight inches—to ensure better reliability. Various numbers of and configurations of wheels may also be utilized including configurations with three, five, six or more as in known in the art. The wheels may be combinations of fixed or pivot wheels and may be of different sizes and configurations as is known in the art. The number, size, type and configuration of wheels provides for various handling, maneuverability and stability characteristics required for various therapeutic uses. Moreover, to enhance the safety, convenience, and durability of a wheeled walking aid and its parts, the wheeled support aid may utilize tubular seats, back seats, and baskets with spacers and cushions.

The powered wheeled support aid can be incorporated with hand-operated brake levers (805) and brakes (810). Similarly the non-powered wheeled support aid can be incorporated with hand-operated brake levers (905) and brakes (910). The brakes on the wheeled support aid may constitute locking brakes to allow the person to stand while supported in a stationary position. Other means of braking may be provided for those with limited use of their arms and hands. The wheeled support aid can be designed to enable greater range for rotating the body from side to side to enable the person in the wheeled support aid to turn from side to side and stand facing one side or the other, or even the back. It may also have a seat that will allow for resting. The wheeled support aid will have adjustable height. The wheeled support aid may also be designed with a folding mechanism for compact storage.

The wheeled support aid can feature hand supports for assisting the entry and exit from the support aid. The wheeled support aid can be constructed from light-weight materials such as aluminum or composites. The wheeled support aid may preferably use tubular seats, back seats and baskets with spacers and cushions.

Figure 56:
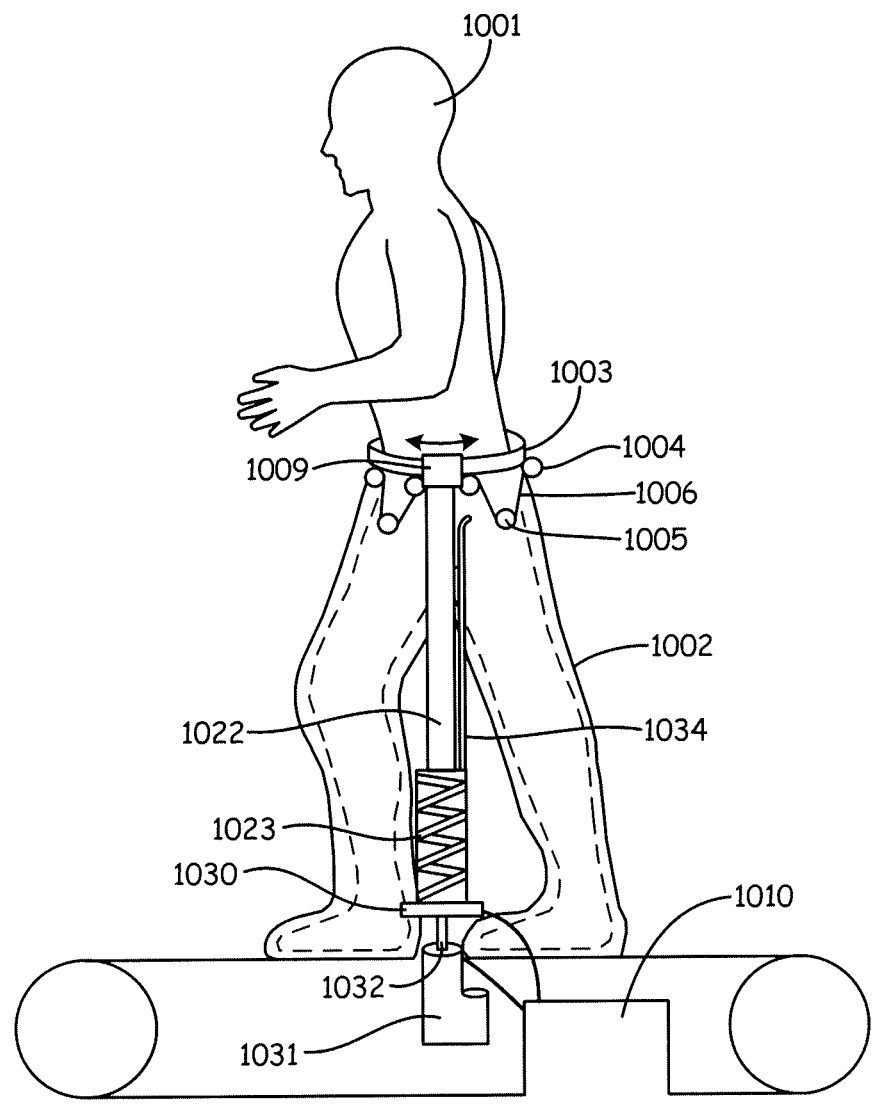
FIG. 56 is a perspective view of the rigid band and pulley system used to provide body weight support to a person on a treadmill with a constant-force adjustment mechanism extending from the treadmill.

FIG. 56 shows a body weight support device for a person (1001) walking or running on a treadmill wherein the constant force adjustment mechanism supports the person from the base of a treadmill rather than overhead. Supporting from the base provides advantages over supporting from overhead. It provides for a low profile, lower cost frame that is particularly suitable for home use. The person (1001) wears a lower body suit (1002). Preferably the suit may be a differential pressure suit as previously described in this application. Alternatively, the suit may be a non-pressurized suit, or a harness. A rigid band (1003) encircles the lower body at approximately the waist. Pulleys (1004) are connected to the band at intervals around the band. Another set of pulleys (1005) is connected to a lower body suit at intervals. A cord (1006) runs through the pulleys on the band and the pulleys on the suit. The cord alternates passing through a pulley on the band and a pulley on the suit. The ends of the cord are connected together so that it forms a continuous loop around the waist through the all pulleys. The cord and pulleys thus connect the suit to the rigid band. The band incorporates a curved linear bearing (1009) for enabling rotary motion of the band at the attachment point to provide additional freedom of rotation as described previously. A constant force adjustment mechanism (1022), attaches to the curved linear bearing (1009).

The constant-force adjustment mechanism (1022) is attached at each side of the treadmill. The constant force adjustment mechanism control system and user interface similar to the constant force adjustment mechanism previously described in this application. In the embodiment described herein compression springs (1023) are utilized to provide the constant force. Other mechanisms that provide a relatively constant force such as constant force air springs might also be utilized in place of the compression springs. At the end of compression spring (1023) is an electronic load cell (1030) capable of measuring the desired compression from 0 to 100 pounds. Mounted on the bottom side of the compression spring is a gear motor (1031) and displacement shaft (1032). The motor has a displacement encoder that is fed to the system microcontroller, along with the load cell information. In this embodiment the user would select two parameters from a control panel (not shown) mounted on the treadmill's control panel: first the desired un-weighting level in pounds and a second a setting that relates to the cross sectional area of the individual. The enclosure (1010) contains an air pressure source, air regulator and microcontroller running control software. A cable 1033 connects the load cell to the enclosure. An air hose (1034) delivers pressurized air to the suit. The software is programmed to deliver a specified air pressure to support unweighting, as well as a control signal to the motors (1031) to displace the compression springs (1023) to a specified level as measured by the load cell (1030). An air line (1011) connects the air pressure source to the pants. The constant force control mechanism is the same as described previously for the powered mobile device.

Figure 57:
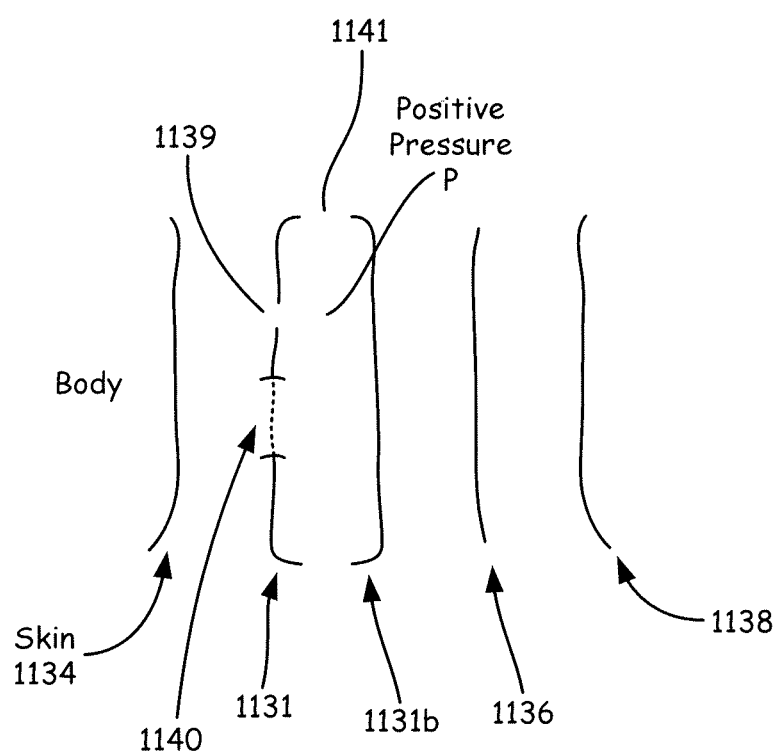
FIG. 57 is a schematic view of the layers of the close-fitting differential pressure body suit.

An improved embodiment of the close fitting differential pressure suit is described below. A construction of the layers of embodiment is shown in FIG. 57. An air-tight inner bladder 1141 maintains the positive pressure P condition inside the suit against the person's body skin 1134. The bladder consists of two layers, an inner layer 1131 and an outer layer 1131*b*. The fabric for the bladder may be formed from any pressure-tight material that is also sufficiently flexible to afford mobility by the person. Preferably the fabric consists of a material that is air impermeable and moisture vapor permeable. An example bladder fabric is TC92 a 4-way stretch polyurethane coated fabric available from Dartex coatings 22 Steel Street, PO Box 70 RI. This both allows the bladder to maintain a positive air pressure P and allows moisture vapor from sweat to permeate through the material to keep the runner 1 The bladder may also be constructed to have holes 1139 that are permeable to air on the inner side next to the skin. The bladder may also be constructed to have sections of another material 1140 that are permeable to air on the inner side next to the skin. This allows for air to circulate between the bladder and the skin. A continuous supply of pressurized air can be supplied from a pressure source and pressure control system as described in this application. The pressure system can be sized to provide the required amount of air flow to maintain cooling. Outer layers 1136 and 118 of the differential pressurized suit 14 composition prevent the suit from expanding due to the force applied by positive pressure P, while maintaining the shape of the suit to fit closely to the body. The bladder section may be the same size as the outer constrain layers.

Figure 58:
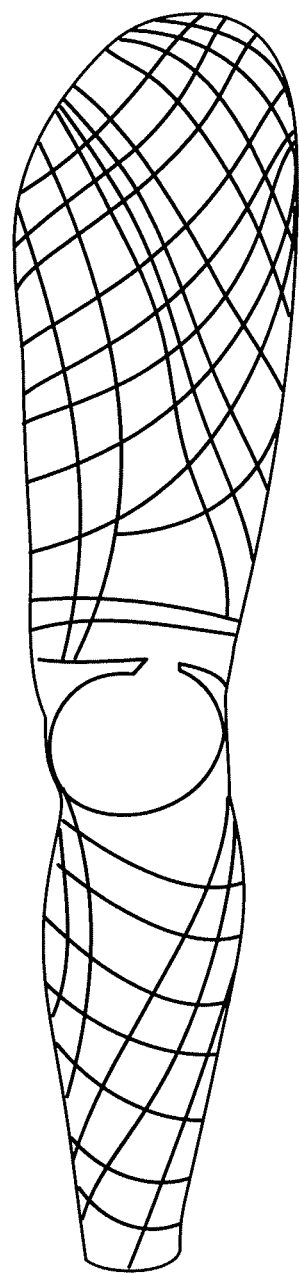
FIG. 58 is a view of a bladder in the body suit.

A pattern for a bladder is shown in FIG. 58. The bladder can be sized to the same size as the outer constraining layers 1136 and 1138 or it may be sized to be smaller than the outer constraining layers. The bladder can be sized to extend various lengths up the waist so that positive pressure is applied only in sections that the bladder extends to beneath the constraining layers. The bladder can extend just to the hips, or just to approximately the pelvic area, or all the way to the waist. The bladder may be patterned so that it conforms to zippers incorporated into the suit. The bladder may be constructed from identical sections of fabric one section forms an inner layer 1131 and one section forms the outer layer 113*b* or the bladder. The bladder may be constructed by sewing the sections together with a heat sealing film at the seams. One heat seal film is Bemis 3218 adhesive film available from Bemis 100 Ayer Rd—Shirley, Mass. 01464 USA.

The fabric for these first and second outer layers 1136 and 1138 should be composed two way stretch fabric. two way stretch fabric. This type of fabric is constructed to mostly be non-extending along one axis, and elastic or extensible along a second axis perpendicular to the first axis. Exemplary two way stretch materials include, without limitation, nylon-Lycra that can be knit or braided, or a monofilament like nylon or Dacron.

The fabric can be more specifically oriented so that its non-extending axis follows lines on the body in which the skin does not stretch or extend during bending or other movement. These lines are known within the industry as "lines-of-non-extension." The concept of lines of non-extension is described in a published technical report: THE USE OF LINES OF NONEXTENSION TO IMPROVE MOBILITY IN FULL-PRESSURE SUITS, ARTHUR S. IBEIALL, RAND DEVELOPMENT CORPORATION, AMRL-TR-64-118. AMRL-TR-64-118. Lines-of-non-extension are directions on the skin of the body in which the skin does not stretch or extend. A picture from the report which maps the lines of non-extension on a mannequin is shown in FIG. 58. There are two sets of lines-of-non-extension on the lower body. One set runs roughly perpendicular to the longitudinal axis of the body, the second set runs roughly parallel to the longitudinal axis of the body.

The constructions of the two outside layers 1136 and 1138 are such that the stretch and non-stretch directions of the fabric are mapped into the lines-of-non-extension as best as possible. This is accomplished by constructing the suit of multiple sections of 2 way stretch fabric in a pattern which maps the direction of the fabric to the lines of non-extension. 2-way stretch fabrics are available from Schoeller Textile USA Seattle Wash.

Figure 59:
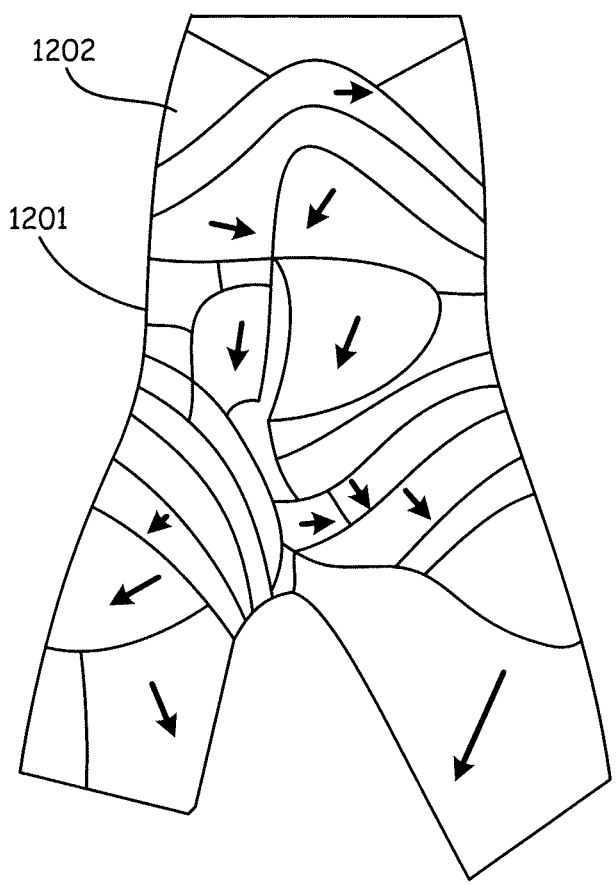
FIG. 59 is a view of a pattern for the first outer layer of the body suit.

A pattern 1201 for the first outer layer 1136 is shown in FIG. 59. The arrows indicate the direction of stretch. The individual sections of fabric are indicated by the sections, for example 1202, shown in the pattern. Lines indicate where seams are sewn between the pieces. The individual layers are sewn together at the seams and the outer edges are sewn together to form a suit. The same method is applied to the outer layer 1138. The first outer layer 1136, second outer layer 1138, and sealed bladder are sewn together to form a single lower body suit. Zippers may be incorporated in the design to facilitate donning and doffing of the suit. In particular zippers may be incorporated from crotch area (to the waist) and at the calves as in common in pants and close fitting tights designs. Generally, the first outer layer 1136 serves to prevent the suit from expending circumferentially under pressure inside the suit.

The suit also incorporates sections of 4-way stretch fabric as necessary in areas that require stretch in both directions. Where appropriate in sections of the body which do not flex, such as the thigh area or lower calves, cloth, mesh, or net material that is non-extendible along both axes may be used.

Figure 60:
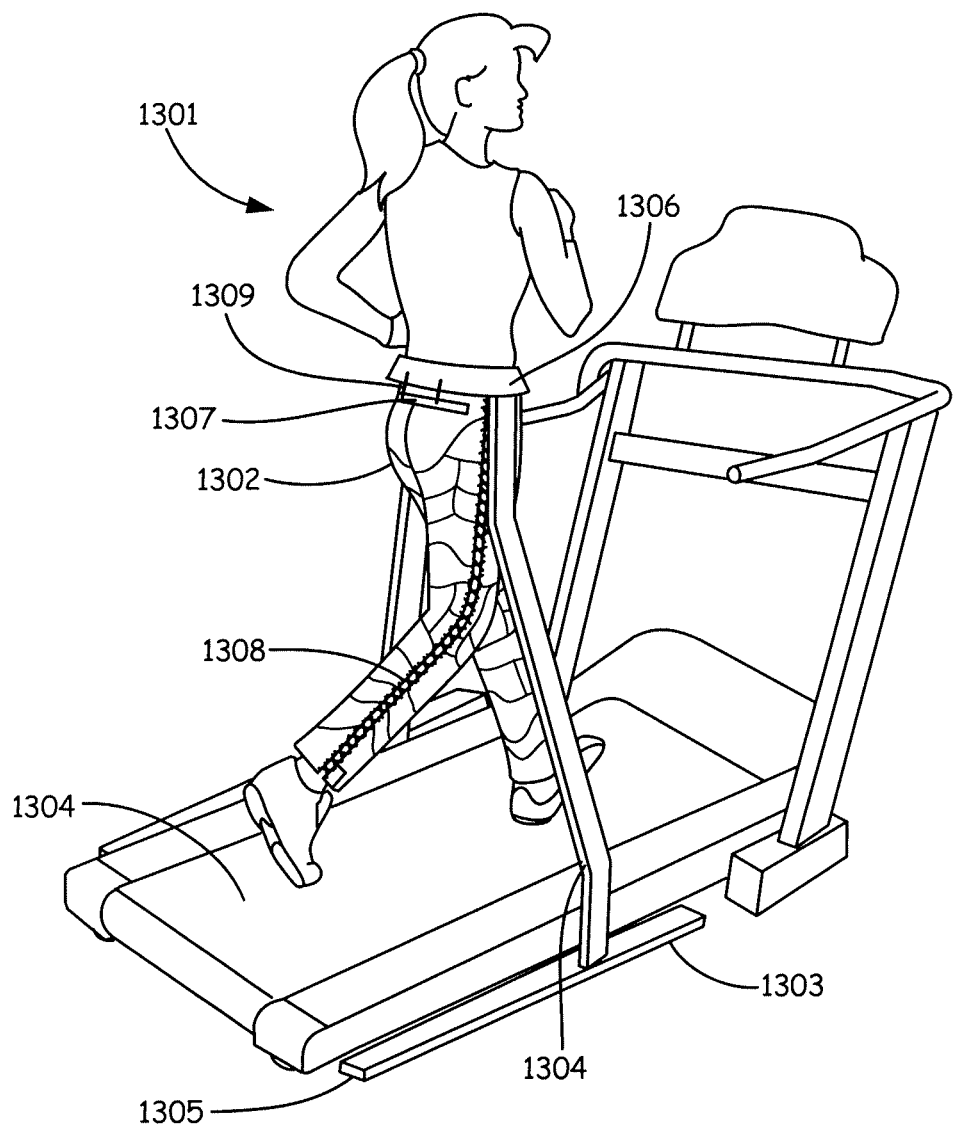
FIG. 60 is a perspective view of a runner on a treadmill-based body weight support device wearing a two-way stretch fabric body suit.

A drawing of a runner 1301 using a body weight support system 1303 on a treadmill 1303 wearing the differential pressure suit 1302 described in this embodiment is shown in FIG. 60. The body weight system support system 1303 includes a supporting frame 1304, a base 1305, a rigid band 1306, and means for attaching the band to the suit 1307. A feature of this design for the body weight support system with a stationary frame has a much lower profile than the overhead support system described previously. This makes this design particularly suitable for in home use. This design of body weight support system can also incorporate the band and pulley system, and the constant force adjustment systems described earlier and shown in FIG. 54. In particular the constant force adjustment system and pressurization system described for the mobile support aid may be incorporated into a frame system similar to this which is mounted on the floor and having a frame that extends to the waist. The suit may also be used in conjunction with the other stationary frame and mobile systems described in this application.

The differential pressure suit on the runner 1301 shown in FIG. 60 shows the suit constructed of sections of 2-way stretch fabric as described previously. The suit 1302 is attached to the rigid band by attachment cords 1309. Suitable rigid support stays 1307 are sewn into the suit to evenly distribute the load from the pressurized suit. Alternatively sections of fabric or a system of suspension cords may be utilized to attach the suit to the frame.

The suit 1302 shown in FIG. 60 has a lacing system 1308. The lacing system facilitates closely fitting the suit to various body shapes and sizes. The lacing system has unique features that enable it to work for long lengths including the length of the entire suit. The lacing system consists of low friction components. Nylon coated boot hooks are used. L friction high strength cords are utilized. Exemplary line is Laser Pro Gold 300 lb test line available from The Kite Shop at.thekiteshoppe.com. Military spec "Nato Hooks" are utilized for the hooks.

While the suit is described as having multiple layers of fabric including air impermeable and two way stretch fabrics orientated and located as described the functions of these various layers can be combined into fewer layers of fabric so that at a minimum the suit is comprised of a single layer of fabric with the functionality of the layers combined. For instance 2-way stretch fabrics that are air impermeable and or water vapor permeable can be utilized to both contain pressurized air and constrain the suit. Or two or more layers of fabric can be laminated together so that the fabric consists of a single layer with the functionality of the individual layers.

Example 1

Mobile Support Device

A rigid band is constructed from curved rigid aluminum strip 1 inch wide and ⅛ inch thick. The band is oval in shape. Pulleys we attached to the band as follows. Two pulleys are attached at the front and back mid-points of the band, two pulleys are attached at the midpoints at the side in the configuration shown in FIG. 47. On each side two more a pulley is attached frontwards on the band from the midpoint pulley and another pulley is attached rearwards. To attach the pulleys to the pants rigid supporting bars are constructed of ⅛" thick ¾" wide aluminum bars are inserted into sleeves sewn into the pants as shown in FIG. 46. A cord made from a low stretch material run alternatively through band pulleys and the suit pulleys and tied in a knot. The cord is adjusted so that the pants pulleys are 4 inches below the waist. One half inch diameter pegs are bolted to the band at the midpoint on each side to serve as attachment pegs to the horizontal C-shaped section of the suspension apparatus. A shaped horizontal component of the suspension apparatus is formed from aluminum stock as shown in FIG. 52 number 23. The radius of curvature is the same as that of the band. One half inch wide slots are milled at the attachment point (27). The band is attached to the C-shaped horizontal component by fitting the pegs of the band into the slots. A delrin block is machined to slide over the slot and hold the peg of band in place.

An L-shaped vertical component of the suspension apparatus is formed from 1 inch diameter, aluminum tubing, FIG. 52 number 20. A bearing is fitted to the bottom of the L-shaped vertical component shown in FIG. 52 number 28. A rotating bearing is fitted at the top FIG. 52 number 24, which is attached to cable. The cable attaches to a constant force adjustment system as previously described in this application.

Example 2

Powered Mobile Support Device

A mobile 'walker' device has been constructed using the concepts illustrated in FIG. 54. A standard commercially available rollator frame was used as a mechanical base. Compression springs (Century Spring) that yield about 50 pounds for 6 inches of compression were used, one on each side as per the FIG. 54. Gear motors that displace the springs were used. The pressure pants, bend and pulley attachment mechanism as described in Example 1 were employed identically in this design, except that the band is pushed up with the compression spring mechanism, instead of pulled up or tensioned with the over-hanging suspensions system. A 24 lead acid battery source is used to power a portable air pump (Thomas), an air regulator (Bellofram), the gear motor, load cell and pressure sensors, and an electronics PLC controller (Galil Inc).

The above specifications and drawings provide a complete description of the structure and operation of the assisted motion system 10 under the present invention. However, the invention is capable of use in various other combinations, modifications, embodiments, and environments without departing from the spirit and scope of the invention. Therefore, the description is not intended to limit the invention to the particular form disclosed, and the invention resides in the claim and hereinafter appended.

We claim:

1. A system for assisting the motion of or supporting a body of a mammal having a body weight during a treatment procedure, said system comprising:
   (a) a pressure-tight suit adapted to being worn over all or a portion of one or more of the mammal's body parts consisting of a torso, leg, or arm, the pressure-tight suit having at least one opening adapted to be positioned around the mammal's torso, leg, arm, or neck for accommodation by the pressure-tight suit of the body parts;
   (b) each opening of the pressure-tight suit having connected adjacent thereto a pressure-tight seal for operative engagement of a body part surface of the mammal;
   (c) inlet means in the suit for introduction of at least one source of a positive pressure or vacuum to an interior of the suit between the mammal body and the suit to create a differential pressure condition therein between the positive pressure or vacuum condition inside the suit, and a pressure condition existing outside the suit;
   (d) a rigid band adapted to be positioned at least partially around the mammal's torso and operatively connected to the suit by means of at least one cord and pulley assembly;
   (e) support means separate from the suit operatively connected to the rigid waist band by attachment means for counteracting a downwards force applied to the suit when it is placed under the differential pressure condition;
   (f) wherein the differential pressure condition is adapted to exert an upwards force upon the body part to offload a portion of the weight of the body to the support means, while the cord and pulley assembly provides the mammal greater lateral and rotational freedom of movement with respect to the support means.

2. The assisted motion system of claim 1, wherein the cord and pulley assembly is adapted to accommodate body rotation about at least one of the axes of the body selected from the group consisting of a superior-inferior axis, a medio-lateral axis through the waist, an anteroposterior axis passing through the waist, and a medio-lateral axis through the hips.

3. The assisted motion system of claim 1, wherein the cord of the as least one cord and pulley assembly is a continuous loop.

4. The assisted motion system of claim 1, wherein the cord of the at least one cord and pulley assembly is not a continuous loop.

5. The assisted motion system of claim 1, wherein the band is flexible in the horizontal plane and rigid in the vertical plane.

6. The assisted motion system of claim 1, wherein two, four, six, eight, twelve, or more pulleys are attached to the band by means of the cord.

7. The assisted motion system of claim 1, wherein the cord comprises a non-elastic material.

8. The assisted motion system of claim 1, wherein the cord comprises an elastic material.

9. The assisted motion system of claim 1 further comprising a mechanism adapted to accommodate rotation of the band about the superior-inferior axis of the body.

10. The assisted motion system of claim 9, wherein the mechanism comprises a curved linear bearing or a curved linear rail.

11. The assisted motion system of claim 1 further comprising a mechanism adapted to accommodate rotation of the band about a medio-lateral axis through the waist.

12. The assisted motion system of claim 1, wherein the support means separate from the suit comprises an overhead structure and the attachment means comprises an actuated cable attached to the overhead structure.

13. The assisted motion system of claim 12 further comprising an L-shaped bracket interconnected between the cable and the band, so that the cable does not interfere with the movements of the mammal.

14. The assisted motion system of claim 1, wherein the support means separate from the suit comprises a mobile apparatus comprising at least two wheels.

15. The assisted motion system of claim 1, wherein the support means separate from the suit comprises a wheeled cart or walker device, and the attachment means comprises a bracket or strap that pivots with respect to the band.

16. The assisted motion system of claim 1, wherein the support means separate from the suit comprises a stationary frame for supporting a body part of the mammal, and the attachment means comprises a bracket or strap that pivots with respect to the band.

17. The assisted motion system of claim 1, wherein the support means separate from the suit comprises a vertical post extending upwardly from a treadmill, stair-master, orbital trainer, cross-country ski trainer, or other exercise apparatus, and the attachment means comprises a bracket or strap that pivots with respect to the band.

18. The assisted motion system of claim 1, wherein the support means separate from the suit further comprises means for providing a constant force tension applied to support the vertical downwards force from a portion of the body weight that is offloaded.

19. The assisted motion system of claim 18, wherein the means for providing the constant force tension comprises at least one air cylinder, mechanical spring, or air spring.

20. The assisted motion system of claim 18, wherein the means for providing the constant force tension comprises an elastic cable.

21. The assisted motion system of claim 18, wherein the cord of the cord and pulley system comprises an elastic material, and the means for providing a constant force tension comprises the elastic cord of the cord and pulley system.

22. The assisted motion system of claim 18, wherein the means for providing the constant force tension comprises an adjustment mechanism for adjusting the level of constant force provided.

23. The assisted motion system of claim 18, wherein the means for providing the constant force tension is powered or manually operated.

24. The assisted motion system of claim 18, wherein the means for providing the constant force tension comprises a load cell and a control system.

25. The assisted motion system of claim 1, wherein the attachment means for connecting the rigid waist band to the separate support means comprises a latch.

26. The assisted motion system of claim 1, wherein the treatment procedure comprises exercise or training, rehabilitation of an injury or to assist mobility, reducing weight on a muscle skeletal structure of the mammal, maintaining proper posture of a muscle skeletal structure of the mammal, treatment for neurological or balance disorders, ambulation, or assisting mobility for the physically disabled.

27. The assisted motion system of claim 1, wherein the mammal to which the suit or harness is adapted is a human.

28. A method for assisting the motion of or supporting a body of a mammal having a body weight during a treatment procedure, said method comprising:
(a) providing a pressure-tight suit adapted to being worn over all or a portion of one or more of the mammal's body parts consisting of a torso, leg, or arm, the pressure-tight suit having at least one opening around the mammal's torso, leg, arm, or neck for accommodation by the pressure-tight suit of the body parts, each opening of the pressure-tight suit having connected adjacent thereto a pressure-tight seal for operative engagement of a body part surface of the mammal, and inlet means in the suit for introduction of at least one source of a positive pressure or vacuum to an interior of the suit between the mammal body and the suit to create a differential pressure condition therein between the positive pressure or vacuum condition inside the suit, and a pressure condition existing outside the suit;
(b) providing a band situated at least partially around the mammal's torso and operatively connected to the suit;
(c) providing support means separate from the suit operatively connected to the band for counteracting a downwards force applied to the suit when it is placed under the differential pressure condition;
(d) applying an upwards external mechanical force to the band to support the vertical downwards force from a portion of the body weight that is offloaded;
(e) introducing a measure of the source of positive pressure or vacuum pressure into the pressure-tight suit
(f) measuring the increase in pressure introduced into the suit;
(g) incrementally adjusting the upwards force applied to the band to maintain a balance of the upwards force with the downwards force exerted by the pressurized suit as the pressure condition is changed within the suit;
(h) wherein the differential pressure condition exerts an upwards force upon the body part to offload a portion of the weight of the body to the support means, and the incrementally adjusted upwards force counteracts downwards force applied to the suit when it is placed under the differential pressure condition.

29. The method of claim 28, wherein the upwards external mechanical force is applied to the band by means of an incrementally adjusted pulley applying upwards force to a cable attached to the support means in the form of an overhead structure, wherein the cable and pulley assembly accommodates vertical movement of the mammal.

30. The method of claim 28 further comprising at least one cord and pulley assembly for attaching the band to the pressure-tight suit to provide further lateral and rotational freedom of movement to the mammal wearing the pressure-tight suit.

31. The method of claim 28 further comprising a user interface and control system for controlling the introduction of positive pressure or vacuum pressure into the pressure-tight suit, and incrementally adjusting the upwards external mechanical force applied to the band.

32. The method of claim 28 further comprising a means for maintaining a balance between the upwards external mechanical force applied to the band and the downwards force applied to the suit when it is placed under the differential pressure condition within plus or minus 1%, 2%, 3%, 5% or 10%.

33. The method of claim 28 further comprising a means to adjust or maintain a difference between net downward force supplied by the pants air pressure and to the upward force on the pants supplied by the counter-tensioning system.

34. A system for assisting the motion of or supporting a body of a mammal having a body weight during a treatment procedure, said system comprising:
(a) a suit or harness made from flexible fabric adapted to being worn over all or a portion of one or more of the mammal's body parts consisting of a torso or leg, the suit or harness having at least one opening adapted to be positioned around the mammal's torso, leg, arm, or neck for accommodation by the suit or harness of the body parts;
(b) a rigid band adapted to be positioned at least partially around the mammal's torso and operatively connected to the suit or harness by means of at least one cord and pulley assembly;
(c) support means separate from the suit or harness operatively connected to the rigid band by attachment means, the support means further having lift means for providing upwards force to the rigid band to offload a portion of the body weight of the mammal;
(d) wherein the lift means exerts an upwards force upon the rigid band and is adapted to exert an upwards force upon the body part accommodated by the suit or harness to offload a portion of the weight of the body to the support means, while the cord and pulley assembly provides the mammal greater lateral and rotational freedom of movement.

35. The assisted motion system of claim 34 further comprising rigid stays incorporated into the suit or harness, such stays being connected to the cord and pulley assembly.

36. The assisted motion system of claim 34, wherein the cord and pulley assembly adapted to be positioned to accommodate body rotation about at least one of the axes of the body selected from the group consisting of a superior-inferior axis, a medio-lateral axis through the waist, an anteroposterior axis passing through the waist, and a medio-lateral axis through the hips.

37. The assisted motion system of claim 34, wherein the cord of the as least one cord and pulley assembly is a continuous loop.

38. The assisted motion system of claim 34, wherein the cord of the at least one cord and pulley assembly is not a continuous loop.

39. The assisted motion system of claim 34, wherein the band is flexible in the horizontal plane and rigid in the vertical plane.

40. The assisted motion system of claim 34, wherein two, four, six, eight, twelve, or more pulleys are attached to the band by means of the cord.

41. The assisted motion system of claim 34, wherein the cord comprises a non-elastic material.

42. The assisted motion system of claim 34, wherein the cord comprises an elastic material.

43. The assisted motion system of claim 34 further comprising a mechanism adapted to accommodate rotation of the band about the superior-inferior axis of the body.

44. The assisted motion system of claim 43, wherein the mechanism comprises a curved linear bearing or a curved linear rail.

45. The assisted motion system of claim 34 further comprising a mechanism adapted to accommodate rotation of the band about a medio-lateral axis through the waist.

46. The assisted motion system of claim 34, wherein the support means separate from the suit comprises an overhead structure and the lift means comprises an actuated cable attached to the overhead structure.

47. The assisted motion system of claim 46 further comprising an L-shaped bracket interconnected between the cable and the band, so that the cable does not interfere with the movements of the mammal.

48. The assisted motion system of claim 34, wherein the support means separate from the suit comprises a mobile apparatus comprising at least two wheels.

49. The assisted motion system of claim 34, wherein the support means separate from the suit comprises a wheel adapted to be positioned substantially ahead of the mammal, and a wheel adapted to be positioned substantially behind the mammal.

50. The assisted motion system of claim 34, wherein the support means separate from the suit comprises a wheeled cart or walker device, or a treadmill, stair-master, orbital trainer, cross-country ski trainer, or other exercise apparatus.

51. The assisted motion system of claim 34, wherein the lift means comprises a hydraulic cylinder, air cylinder, or linear actuator attached to the support means.

52. The assisted motion system of claim 34, wherein the support means separate from the suit further comprises means for providing a constant force tension applied to support the vertical downwards force from a portion of the body weight that is offloaded, and adjust that tension to accommodate the vertical movement of the mammal's body.

53. The assisted motion system of claim 52, wherein the means for providing the constant force tension comprises at least one air cylinder, mechanical spring, or air spring.

54. The assisted motion system of claim 53, wherein the means for providing the constant force tension comprises an elastic cable.

55. The assisted motion system of claim 52, wherein the cord of the cord and pulley system comprises an elastic material, and the means for providing a constant force tension comprises the elastic cord of the cord and pulley system.

56. The assisted motion system of claim 52, wherein the means for providing the constant force tension comprises an adjustment mechanism for adjusting the level of constant force provided.

57. The assisted motion system of claim 52, wherein the means for providing the constant force tension is powered or manually operated.

58. The assisted motion system of claim 52, wherein the means for providing the constant force tension comprises a load cell and a control system.

59. The assisted motion system of claim 34, wherein the attachment means for connecting the rigid waist band to the separate support means comprises a latch.

60. The assisted motion system of claim 34, wherein the treatment procedure comprises exercise or training, rehabilitation of an injury or to assist mobility, reducing weight on a muscle skeletal structure of the mammal, maintaining proper posture of a muscle skeletal structure of the mammal, treatment for neurological or balance disorders, ambulation, or assisting mobility for the physically disabled.

61. The assisted motion system of claim 34, wherein the mammal to which the suit or harness is adapted is a human.

62. A system for assisting the motion of or supporting a body of a mammal having a body weight during a treatment procedure, said system comprising:
   (a) a suit made from flexible fabric adapted to being worn over all or a portion of one or more of the mammal's body parts consisting of a torso or leg, the suit having at least one opening adapted to be positioned around the mammal's torso, leg, arm, or a neck for accommodation by the suit of the body parts;
   (b) a rigid band adapted to be positioned at least partially around the mammal's torso and operatively connected to the suit;
   (c) support means separate from the suit operatively connected to the rigid band by attachment means;
   (d) lift means for providing vertically upwards force to the rigid band or upon the body part accommodated by the suit to offload a portion of the body weight of the mammal to the separate support means;
   (e) wherein the suit comprises at least a first layer and a second layer wherein each layer is comprised of material that is non-extensible along a first axis, and extensible along a second axis not parallel to its first axis;
   (f) wherein:
      (i) the non-extensible axis of the first layer of the suit is adapted to be oriented relative to the body part to approximately be aligned in parallel to the line of skin non-extension of the body part;
      (ii) the non-extensible axis of the second layer is oriented relative to the body part to approximately be aligned perpendicular to the line of skin non-extension of the body part; and
      (iii) the first layer and the second layer of the suit are free to stretch and move along the extensible second axis as the body part is moved;
   (g) wherein the lift means exerts an upwards force upon the rigid band or is adapted to exert an upwards force upon the body part accommodated by the suit to offload a portion of the weight of the body to the separate support means.

63. The assisted motion system of claim 62, wherein the support means separate from the suit comprises an overhead structure and the lift means comprises an actuated cable attached to the overhead structure.

64. The assisted motion system of claim 62, wherein the support means separate from the suit comprises a wheeled cart or walker device, or a treadmill, stair-master, orbital trainer, cross-country ski trainer, or other exercise apparatus.

65. The assisted motion system of claim 62, wherein the lift means comprises a hydraulic cylinder, air cylinder, or linear actuator attached to the support means.

66. The assisted motion system of claim 62, wherein the suit comprises a pressure-tight suit made from flexible fabric with each opening of the pressure-tight suit having connected adjacent thereto a pressure-tight seal adapted for operative engagement with a body part surface of the mammal, and inlet means in the suit for introduction of at least one source of a positive pressure to an interior of the suit between the mammal body and the suit to create a differential pressure condition therein between the positive pressure condition inside the suit, and a pressure condition existing outside the suit, and the lift means comprises the differential pressure condition being adapted to exert an upwards force upon the body part to offload a portion of the weight of the body to the support means.

67. The assisted motion system of claim 62, wherein the first layer comprises at least two pieces of fabric secured to each other in a side-by-side pattern, so that for each piece of fabric, the piece is adapted to cover an area of the body part and the non-extensible axis of that fabric piece is adapted to be approximately in parallel alignment with one of the lines of skin non-extension of the area of the body part covered by the fabric piece.

68. The assisted motion system of claim 67, wherein the second layer comprises at least two pieces of fabric secured to each other in a side-by-side pattern, so that for each piece of fabric, the piece is adapted to cover an area of the body part and the non-extensible axis of that fabric piece is adapted to be approximately in parallel alignment with one of the lines of skin non-extension for the area of the body part covered by the fabric piece.

69. The assisted motion system of claim 68, wherein:
   (a) the non-extensible axis of each fabric piece of the first layer is adapted to be approximately in parallel alignment with a first set of the lines of skin non-extension of the area of the body part covered by the fabric piece; and
   (b) the non-extensible axis of each fabric piece of the second layer is adapted to be approximately in parallel alignment with a second set of the lines of skin non-extension of the area of the body part covered by the fabric piece.

70. The assisted motion system of claim 62 further comprising at least one cord and pulley assembly operatively connecting the rigid band to the suit, wherein the cord and pulley assembly is adapted to provide the mammal greater lateral and rotational freedom of movement with respect to the support means, while the support means is adapted to accommodate vertical movement of the mammal.

71. A suit made from flexible fabric adapted to being worn over all or a portion of one or more of a mammal's body parts consisting of a torso, leg, or an arm, the suit having at least one opening adapted to be positioned around the mammal's torso, leg, arm, or a neck for accommodation by the flexible fabric of the body parts, the body part having at least one line of skin non-extension when it is moved, the suit comprising:
   (a) at least a first layer and a second layer made from fabric formed from a yarn or thread of elastic material, wherein the fabric of each layer is non-extensible along a first axis, and extensible along a second axis not parallel to its first axis;
   (b) wherein the non-extensible axis of the first layer of the suit is adapted to be oriented relative to the body part to approximately be aligned in parallel to the line of skin non-extension of the body part;
   (c) wherein the non-extensible axis of the second layer is adapted to be oriented relative to the body part to approximately be aligned perpendicular to the line of skin non-extension of the body part; and
   (d) wherein the first layer and the second layer of the suit are free to stretch and move along the extensible second axis as the body part is moved.

72. The suit of claim 71, wherein the first layer comprises at least two pieces of fabric secured to each other in a side-by-side pattern, so that for each piece of fabric, the piece is adapted to cover an area of the body part and the non-extensible axis of that fabric piece is adapted to be approximately in parallel alignment with one of the lines of skin non-extension of the area of the body part covered by the fabric piece.

73. The suit of claim 72, wherein the second layer comprises at least two pieces of fabric secured to each other in a side-by-side pattern, so that for each piece of fabric, the piece is adapted to cover an area of the body part and the non-extensible axis of that fabric piece is adapted to be approximately in parallel alignment with one of the lines of skin non-extension for the area of the body part covered by the fabric piece.

74. The suit of claim 73, wherein:
   (a) the non-extensible axis of each fabric piece of the first layer is adapted to be approximately in parallel alignment with a first set of the lines of skin non-extension of the area of the body part covered by the fabric piece; and
   (b) the non-extensible axis of each fabric piece of the second layer is adapted to be approximately in parallel alignment with a second set of the lines of skin non-extension of the area of the body part covered by the fabric piece.

75. The suit of claim 71 further comprising at least one lacing system to accommodate fitting the suit to the body part.

76. The suit of claim 75, wherein the components of the lacing system comprise low friction materials.

77. The suit of claim 71, wherein the suit comprises a pressure-tight suit made from flexible fabric with each opening of the pressure-tight suit having connected adjacent thereto a pressure-tight seal for operative engagement of a body part surface of the mammal, and inlet means in the suit for introduction of at least one source of a positive pressure or vacuum to an interior of the suit between the mammal body and the suit to create a differential pressure condition therein between the positive pressure or vacuum condition inside the suit, and a pressure condition existing outside the suit.

78. The suit of claim 77 further comprising means within the pressure-tight suit for regulating an air temperature or humidity condition within the suit.

79. The suit of claim 77, wherein pressure-tight seal comprises an air bladder.

80. The suit of claim 77 further comprising a bladder attached to an interior of the pressure-tight suit adapted to be positioned between the suit and the body part, wherein the positive pressure introduced into the interior of the suit is contained within the bladder.

81. The suit of claim 80, wherein the bladder has air holes or sections of air-permeable material on the inner side of the bladder adapted to face the body.

82. The suit of claim 81, wherein the bladder comprises a four-way stretch material.

83. The suit of claim 81, wherein at least one cord and pulley assembly is operatively connected to the suit.

84. The suit of claim 71, wherein the at least one layer comprises an inner vent layer, air pressure resistant layer, air impermeable and moisture vapor permeable layer.

\* \* \* \* \*